(12) United States Patent
Kilkenny et al.

(10) Patent No.: US 7,741,263 B2
(45) Date of Patent: *Jun. 22, 2010

(54) CLEANING COMPOSITION

(75) Inventors: Andrew Kilkenny, Pleasanton, CA (US); Elias A. Shaheen, San Ramon, CA (US); Robert L. Blum, Clayton, CA (US); Shuman Mitra, Dublin, CA (US); Malcolm De Leo, Castro Valley, CA (US); Shona L. Nelson, Livermore, CA (US)

(73) Assignee: The Clorox Company, Oakland, CA (US)

( * ) Notice: Subject to any disclaimer, the term of this patent is extended or adjusted under 35 U.S.C. 154(b) by 757 days.

This patent is subject to a terminal disclaimer.

(21) Appl. No.: 11/001,335

(22) Filed: Dec. 1, 2004

(65) Prior Publication Data
US 2006/0009369 A1 Jan. 12, 2006

Related U.S. Application Data

(63) Continuation-in-part of application No. 09/939,383, filed on Aug. 24, 2001, now abandoned, and a continuation-in-part of application No. 09/939,179, filed on Aug. 24, 2001, which is a continuation-in-part of application No. 09/737,641, filed on Dec. 14, 2000.

(51) Int. Cl.
*C11D 1/75* (2006.01)
*C11D 1/62* (2006.01)
*C11D 3/28* (2006.01)
*C11D 3/44* (2006.01)

(52) U.S. Cl. .............. 510/384; 510/433; 510/438; 510/470; 510/500; 510/503; 510/504; 510/505; 510/506; 134/42; 422/28

(58) Field of Classification Search .............. 510/384, 510/433, 438, 470, 500, 503, 504, 505, 506; 134/42; 422/28
See application file for complete search history.

(56) References Cited

U.S. PATENT DOCUMENTS

| | | | |
|---|---|---|---|
| 3,965,026 A | 6/1976 | Lancz | |
| 4,265,772 A | 5/1981 | Jones | |
| 4,455,250 A | 6/1984 | Frazier | |
| 4,540,505 A | 9/1985 | Frazier | |
| 4,597,887 A | 7/1986 | Colodney | |
| 4,615,937 A | 10/1986 | Bouchette | |
| 4,666,621 A | 5/1987 | Clark et al. | |
| 4,725,489 A | 2/1988 | Jones et al. | |
| 4,748,158 A | 5/1988 | Biermann et al. | |
| 4,781,974 A | 11/1988 | Bouchette et al. | |
| 4,895,667 A | 1/1990 | Fox et al. | |
| 4,895,669 A | 1/1990 | Choy et al. | |
| 4,923,685 A | 5/1990 | Wuelknitz et al. | |
| 5,037,647 A | 8/1991 | Chowhan et al. | |
| 5,141,803 A | 8/1992 | Pregozen | |
| 5,252,245 A | 10/1993 | Garabedian, Jr. et al. | |
| 5,284,875 A | 2/1994 | Martin | |
| 5,322,856 A | 6/1994 | Martin | |
| 5,330,675 A | 7/1994 | Kroner et al. | |
| 5,403,505 A | 4/1995 | Hachmann et al. | |
| 5,405,878 A | 4/1995 | Ellis et al. | |
| 5,421,898 A | 6/1995 | Cavanagh | |
| 5,437,807 A | 8/1995 | Garabedian, Jr. et al. | |
| 5,454,984 A | 10/1995 | Graubart et al. | |
| 5,468,423 A | 11/1995 | Garabedian, Jr. et al. | |
| 5,520,920 A | 5/1996 | Castillo | |
| 5,522,942 A | 6/1996 | Graubart et al. | |
| 5,523,024 A | 6/1996 | Garabedian, Jr. et al. | |
| 5,529,713 A | 6/1996 | Gauthier-Fournier | |
| 5,536,494 A | 7/1996 | Park | |
| 5,540,864 A | 7/1996 | Michael | |
| 5,576,284 A | 11/1996 | van Buskirk et al. | |
| 5,719,113 A | 2/1998 | Fendler et al. | |
| 5,728,667 A | 3/1998 | Richter | |
| 5,739,168 A | 4/1998 | Hioki et al. | |
| 5,762,948 A | 6/1998 | Blackburn et al. | |
| 5,814,591 A | 9/1998 | Mills et al. | |
| 5,817,615 A | 10/1998 | Garabedian, Jr. et al. | |
| 5,851,981 A | 12/1998 | Choy et al. | |
| 5,908,707 A | 6/1999 | Cabell et al. | |
| 5,925,681 A | 7/1999 | Crisanti et al. | |
| 5,929,016 A | 7/1999 | Harrison | |
| 5,962,399 A | 10/1999 | Wulff et al. | |
| 6,004,916 A | 12/1999 | Mills et al. | |
| 6,013,615 A | 1/2000 | Zhou et al. | |
| 6,017,561 A | 1/2000 | Zhou et al. | |
| 6,017,869 A | 1/2000 | Lu et al. | |
| 6,022,841 A | 2/2000 | Lu et al. | |
| 6,045,817 A | 4/2000 | Ananthapadmanabhan et al. | |

(Continued)

FOREIGN PATENT DOCUMENTS

| | | |
|---|---|---|
| EP | 580838 | 10/1993 |
| EP | 606712 | 7/1994 |
| EP | 647706 | 4/1995 |
| EP | 691397 | 1/1996 |
| EP | 815189 | 12/1996 |
| EP | 937125 | 10/1999 |
| WO | WO 93/16162 | 8/1993 |
| WO | WO 96/14835 | 5/1996 |
| WO | WO 96/30473 | 10/1996 |

(Continued)

*Primary Examiner*—Gregory R Del Cotto
(74) *Attorney, Agent, or Firm*—Erin Collins; Brian E. Turung

(57) ABSTRACT

An improved cleaning composition and method adapted to clean a variety of hard surfaces. The improved cleaning composition and method includes the use of a cationic biocide that includes biguanide compounds and/or quats.

37 Claims, 3 Drawing Sheets

U.S. PATENT DOCUMENTS

| | | | |
|---|---|---|---|
| 6,066,674 | A | 5/2000 | Hioki et al. |
| 6,080,387 | A | 6/2000 | Zhou et al. |
| 6,083,517 | A | 7/2000 | Ananthapadmanabhan et al. |
| 6,090,771 | A | 7/2000 | Burt et al. |
| 6,096,701 | A | 8/2000 | Mondin et al. |
| 6,114,298 | A | 9/2000 | Petri et al. |
| 6,126,931 | A | 10/2000 | Sawan et al. |
| 6,136,770 | A | 10/2000 | Cheung et al. |
| 6,184,195 | B1 | 2/2001 | Cheung et al. |
| 6,211,124 | B1 | 4/2001 | Omerod, IV |
| 6,255,270 | B1 | 7/2001 | Barger et al. |
| 6,258,368 | B1 | 7/2001 | Beerse |
| 6,294,186 | B1 | 9/2001 | Beerse et al. |
| 6,340,663 | B1 | 1/2002 | Deleo et al. |
| 6,353,022 | B1 | 3/2002 | Schneider et al. |
| 6,451,333 | B1 | 9/2002 | Beerse et al. |
| 6,559,116 | B1 | 5/2003 | Godfroid et al. |
| 6,613,728 | B1 | 9/2003 | Sirianni |
| 6,667,290 | B2 | 12/2003 | Svendsen |
| 6,825,158 | B2 * | 11/2004 | Mitra et al. ............... 510/295 |
| 6,844,308 | B1 | 1/2005 | Dastbaz |
| 6,936,580 | B2 | 8/2005 | Sherry |
| 6,951,834 | B2 * | 10/2005 | Mitra et al. ............... 510/295 |
| 2002/0031486 | A1 | 3/2002 | Lunsman |
| 2002/0137631 | A1 | 9/2002 | Falder |
| 2003/0147826 | A1 | 8/2003 | Anthony |
| 2004/0194800 | A1 | 10/2004 | Chang |
| 2005/0054257 | A1 | 3/2005 | Barnabas |
| 2005/0113277 | A1 | 5/2005 | Sherry |
| 2005/0121054 | A1 | 6/2005 | Barnabas |
| 2005/0133174 | A1 | 6/2005 | Gorley |
| 2005/0148260 | A1 | 7/2005 | Kopacz |
| 2005/0202991 | A1 | 9/2005 | Dominicis |

FOREIGN PATENT DOCUMENTS

| | | |
|---|---|---|
| WO | WO 97/40814 | 11/1997 |
| WO | WO 98/03713 | 1/1998 |
| WO | WO 98/16606 | 4/1998 |
| WO | WO 98/44791 | 10/1998 |
| WO | WO 98/55570 | 10/1998 |
| WO | WO 98/55569 | 12/1998 |
| WO | WO 99/58631 | 11/1999 |
| WO | WO 99/60852 | 12/1999 |
| WO | WO 0000026 | 1/2000 |
| WO | WO 00/09642 | 2/2000 |
| WO | WO 0063337 | 10/2000 |
| WO | WO 01/23510 A2 | 4/2001 |
| WO | WO 01/23511 A1 | 4/2001 |

* cited by examiner

CLEANING COMPOSITION

The present invention is a continuation-in-part of U.S. patent application Ser. No. 09/939,383 filed Aug. 24, 2001 now abandoned entitled "Bactericidal Cleaning Wipe," and is incorporated herein by reference. The present invention is also a continuation-in-part of co-pending U.S. patent application Ser. No. 09/939,179 filed Aug. 24, 2001 entitled "Bactericidal Cleaning Wipe," which in turn is a continuation-in-part of co-pending U.S. patent application Ser. No. 09/737,641 filed Dec. 14, 2000 entitled "Bactericidal Cleaning Wipe." U.S. patent application Ser. No. 09/939,179 filed Aug. 24, 2001 and Ser. No. 09/737,641 filed Dec. 14, 2000 are incorporated herein by reference.

The present invention relates to an improved cleaning composition that includes a cationic biocide. The cleaning composition can be used alone, in combination with one or more other cleaning compositions, and/or in combination towel, cloth, rag, sponge, mop, squeegee, and the like.

BACKGROUND OF THE INVENTION

Many types of cleaning compositions have been developed to clean various types of products and/or surfaces. Some of these cleaning compositions included one or more compounds to disinfect, sanitize, and/or sterilize the product and/or surface. Acids and alcohols have been traditionally added to cleaning solutions as the principal biocide of the cleaning solution. The present invention relates to an improved cleaning composition having that includes at least one cationic biocides such as, but not limited to, biguanide compounds and/or quaternary ammonium salts ("quats") as the anti-microbial active. The cleaning composition can include other traditional anti-microbial actives such as, but not limited to, one or more acids and/or alcohols. The cleaning composition is envisioned as being used in a wide variety of applications. As can be appreciated, the additives in the cleaning composition that are used in combination with the cationic biocide as the anti-microbial active may vary depending on the particular application of the cleaning composition.

Cleaning wipes are a relatively recent concept that has gained wide public acceptance, especially in the area of infant care products. Infant care wipes commonly include inverse emulsions (i.e. water-in-liquid). Cleaning wipes have also included waxes to polish and clean furniture and/or other metal, plastic and/or wood surfaces. Cleaning wipes have further included soaps and/or detergents to clean an individual's hands, countertops, floors, appliances, and/or the like. Cleaning wipes have also included ammonia to clean glass surfaces. Alcohol and various other biocides have been included on cleaning wipes to disinfect a variety of surfaces.

One type of biocide that has been used in cleaning wipes is quats. Liquid cleaners applied to cleaning wipes typically include relatively large amounts of quat. These cleaning wipes are typically used on hard surfaces such as floors, countertops, glass surfaces, sinks, toilets, appliances, and/or the like. Although quats are excellent biocides, quats can cause skin irritation when used in too high of concentrations. In addition, only about 50% of the quat is released from the wipe when the wipe is applied to a surface, thus added quat is included in the liquid cleaner to ensure that the desired amount of quat transfers to the cleaned surface. Other biocides such as biguanide compounds also have a low release rate from the wipe. Since the quat and/or biguanide compound is typically one of the higher cost components of the cleaner, the larger quat and/or biguanide concentrations used in the liquid cleaner translates into higher product costs. There have been various attempts to develop liquid cleaners having improved quat release from the cleaning wipes. Some cleaning formulations use a high weight percentage of isopropyl alcohol to promote quat release from the cleaning wipe. It has been observed that isopropyl alcohol in amounts of over about 12% can improve the quat release from the wipe. The use of isopropyl alcohol is also beneficial in that the alcohol has its own antimicrobial properties and cost substantially less than quats. Although the use of isopropyl alcohol in the cleaning formulation improves quat release from the wipe, a substantial amount of quat still remains on the cleaning wipe after use. In addition, local, state and/or federal governments have begun to promulgate regulations on the amount of isopropyl alcohol that can be used in cleaners. Indeed, in California, regulations have been proposed to regulate the use of cleaners containing over 4-5 weight percent isopropyl alcohol. As a result, cleaners having high concentrations of isopropyl alcohol may be less preferred.

Quats also tend to leave residues and/or cause streaking after being applied to various surfaces. The residue and streaking problems are of great concern to consumers since the visual appearance of the cleaned surface functions as a visual indicator of the effectiveness of the cleaner. Consumers also judge the cleaning effectiveness of the cleaner by touching the cleaned surface. Sticky surfaces typically indicate to the consumer that the surface has not been effectively cleaned. Cleaning formulations that tend to leave residues and/or cause streaking tend to produce a less shiny, thus a visually perceived less clean surface, and further tend to leave a sticky surface. This is especially true with mop and wet wipe applications, where such compositions are left to dry on the surface without rinsing. As a result, the consumer perceives that the cleaned surface has not be effectively cleaned irrespective of the fact the surface may have been properly cleaned and disinfected. Liquid cleaners having a high quat content are also subject to various local, state and/or federal regulations due to the toxicity of the quat in high concentrations.

Various types of biocides are also used to disinfect, sanitize, and/or sterilize tools and/or equipment. Such biocides are commonly used in the medical field. Biocides such as quats and biguanide compounds have typically not been used because of their cost. Typically alcohols are used as the disinfectant. However, the use of alcohol has come under more federal, state and local regulation, thus interest in the use of other biocides has gained interest in recent years.

Biocides are also used to disinfect, sanitize, and/or sterilize areas that have been exposed to infectious biological agents (e.g. anthrax, small pox). Presently, biocides such as quats and biguanide compounds have not been used for such applications.

In view of the present state of the art of cleaning compositions, there is a demand for an improved cleaning composition that can be used in a variety of applications to disinfect, sanitize, and/or sterilize surfaces without leaving undesired residues and/or streaking on the cleaned surface, without one or more components overly absorbing and/or adsorbing into the cleaned surface, and/or which cleaning composition is cost effective to use.

SUMMARY OF THE INVENTION

The present invention is related to an improved cleaning composition that includes a cationic biocide. The improved cleaning composition is generally a liquid cleaner; however, the improved cleaning composition may be in an aerosol, solid or semi-solid form. The improved cleaning composition can be used by itself or combined with other cleaning formulations. The improved cleaning composition can be loaded onto an absorbent and/or absorbent material, and/or can be used separately from an absorbent and/or absorbent material. The absorbent and/or absorbent material includes, but is not limited to, cleaning wipes, cloths, sponges (e.g., cellulose, synthetic, etc.), paper towels, napkins, rags, mop heads, cleaning pads, towels, brooms, other absorbent cleaning tools, and/or the like. In one embodiment of the present invention, the improved cleaning composition is applied to a surface to be cleaned prior to exposing the improved cleaning composition to an absorbent and/or adsorbent material. In such applications, the improved cleaning composition is not pre-loaded onto an absorbent and/or adsorbent material, but instead is applied by the user to a surface to be cleaned and then wiped up by the absorbent and/or adsorbent material. As can be appreciated, the absorbent and/or adsorbent material can include some improved cleaning composition prior to wiping the surface on which the improved cleaning composition is pre-applied. In another and/or alternative embodiment of the present invention, the improved cleaning composition is pre-applied to the absorbent and/or absorbent material for ease of use by the consumer. The improved cleaning composition can be packaged to be used alone or in combination with other cleaners and/or absorbent or adsorbent materials. The improved cleaning composition is typically formulated to clean hard surfaces such as, but not limited to, counter tops; however, the improved cleaning composition has much broader applications and be used as a clean glass cleaner; appliance cleaner; floor cleaner; rug cleaner; area disinfect, sanitizer, and/or sterilizer; and/or the like. As used herein, the term "hard surfaces" includes, but is not limited to, bathroom surfaces (e.g., floor, tub, shower, mirror, toilet, bidet, bathroom fixtures, etc.), kitchen surfaces (e.g., counter tops, stove, oven, range, sink, refrigerator, microwave, appliances, tables, chairs, cabinets, drawers, floors, etc.), furniture surfaces (e.g., tables, chairs, sofas, love seats, benches, beds, stools, armoires, chests, dressers, display cabinets, clocks, buffet, shades, shutters, entertainment centers, arm rails, lamps, banisters, libraries, cabinets, desks, doors, shelves, couches, beds, carts, pianos, statues and other art, mirrors, racks, fans, light fixtures, pool table, ping pong table, soccer table, card table, etc.), statues, windows, window ledges, tools, utility devices (e.g., telephones, radios, t.v., stereo equipment, CD and DVD players, analog and digital sound devices, palm computers, laptop computers, desktop and tower computers, computer monitors, etc.), automobiles (e.g., interior and exterior surfaces), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. The improved cleaning composition can also be used in a variety of industrial and institutional applications. As used herein, the terms "industrial" and "institutional" shall mean the fields of use which include, but are not limited to, contract (e.g., professional) cleaning and disinfecting, retail facilities cleaning and disinfecting, industrial/manufacturing facilities cleaning and disinfecting, office cleaning and disinfecting services, hotel/restaurant/entertainment cleaning and disinfecting, health care (e.g., hospitals, urgent care facilities, clinics, nursing homes, medical/dental offices, laboratories) facilities cleaning and disinfecting, educational facilities cleaning and disinfecting, recreational (e.g., arenas, coliseums, resorts, halls, stadiums, cruise lines, arcades, convention centers, museums, theaters, clubs, family entertainment complexes (e.g., indoor and/or outdoor), marinas, parks) facilities cleaning and disinfecting, food service facilities cleaning and disinfecting, governmental facilities cleaning and disinfecting, public transportation facilities (e.g., airports, airlines, cabs, buses, trains, subways, boats, ports, and their associated properties) cleaning and disinfecting. The improved cleaning composition can be in concentrated form or unconcentrated form (e.g., ready to use form). When the improved cleaning composition is not first impregnated on an absorbent or adsorbent material, the improved cleaning composition can be dispensed and/or sprayed as liquid from a container, as an aerosol from an aerosol container, or as a crystal, powder, paste, or otherwise semi-solid or solid form from a container. The improved cleaning composition can be used as a disinfectant, sanitizer, and/or sterilizer. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." As used herein, the term "sterilize" shall mean the substantially complete elimination or destruction of all forms of microbial life and which is authorized under the applicable regulatory laws to make legal claims as a "Sterilant" or to have sterilizing properties or qualities.

In one aspect of the present invention, the absorbent and/or absorbent material can be at least partially impregnated with the improved cleaning composition. When the improved cleaning composition is at least partially loaded or impregnated onto the absorbent and/or absorbent material, the improved cleaning composition is formulated to have a viscosity that allows such loading. Typically, the viscosity of the improved cleaning composition is less than about 1000 centipoise ("cps") when the improved cleaning composition is at least partially loaded or impregnated onto an absorbent and/or absorbent material. The viscosity of the improved cleaning composition can be greater than 1000 cps when the improved cleaning composition is used separately from an absorbent and/or absorbent material, and/or is not to be preloaded onto an absorbent and/or absorbent material.

In another and/or alternative aspect of the present invention, the cleaning wipe onto which the improved cleaning composition is loaded at least partially includes an absorbent and/or adsorbent material. In one embodiment, the cleaning wipe includes, but is not limited to, a woven and/or a nonwoven material. In one aspect of this embodiment, the nonwoven material includes, but is not limited to, nonwoven, fibrous sheet materials. In another and/or alternative aspect of this embodiment, the nonwoven material includes, but is not limited to, meltblown, coform, air-laid, spun bond, wet laid, bonded-carded web materials, and/or hydroentangled (also known as spunlaced) materials. In still another and/or alternative aspect of this embodiment, the woven material includes, but is not limited to, cotton fibers, cotton/nylon blends and/or other textiles. In another and/or alternative embodiment, the cleaning wipe includes a sponge and/or sponge-like material. In one aspect of this embodiment, the sponge and/or sponge-like material includes, but is not limited to, regenerated cellulose and/or polyurethane foams. In still another and/or alternative embodiment, the cleaning wipe includes, but is not limited to, wood pulp, a blend of wood pulp, and/or synthetic fibers. In one aspect of this embodiment, the synthetic fibers include, but are not limited to, polyester, rayon, nylon, polypropylene, polyethylene, and/or cellulose polymers. In still another and/or alternative embodiment, the cleaning wipe includes a binder. In yet another and/or alternative embodiment, the absorbent and/or adsorbent material is part of a single or multiple layer cleaning pad. The cleaning pad can be used individually and/or in combination with a mop and/or other cleaning device. In one aspect of this embodiment, the cleaning pad has an absorbent capacity, when measured under a confining pressure of about 0.09 psi after about 20 minutes, of at least about 1 g deionized water per gram of the cleaning pad, typically at least about 5 g deionized water per gram of the cleaning pad, and more typically at least about 10 g deionized water per gram of the cleaning pad. In another and/or alternative aspect of this embodiment, the cleaning pad can have a total fluid capacity (of deionized water) of at least about 100 g; however, pads having a total fluid capacity of less than about 100 g are within the scope of the invention even though such cleaning pads are typically not as well suited for cleaning large areas. In still another and/or alternative aspect of this embodiment, there can be an absorbent layer on and/or in the cleaning pad which serves to retain fluid and soil absorbed by the cleaning pad during use. The absorbent layer typically includes at least one layer, and typically comprises multiple layers which are designed to provide the cleaning pad with multiple planar surfaces. In still yet another and/or alternative embodiment, cleaning wipe or cleaning pad can include a superabsorbent material. As used herein, the term "superabsorbent material" means any absorbent material having a g/g capacity for water of at least about 15 g/g, when measured under a confining pressure of about 0.3 psi. Representative superabsorbent materials include, but are not limited to, water insoluble, water-swellable superabsorbent gelling polymers. The superabsorbent gelling polymers useful in the present invention can have a size, shape and/or morphology varying over a wide range. These polymers can be in the form of particles that do not have a large ratio of greatest dimension to smallest dimension (e.g., granules, flakes, pulverulents, inter-particle aggregates, interparticle crosslinked aggregates, and the like), and/or the polymers can be in the form of fibers, sheets, films, foams, laminates, and the like. The use of superabsorbent gelling polymers in fibrous form provides the benefit of providing enhanced retention of the superabsorbent material, relative to particles, during the cleaning process. Superabsorbent gelling polymers useful in the present invention include, but are not limited to, a variety of water-insoluble, but water-swellable polymers capable of absorbing large quantities of fluids. Such polymeric materials are also commonly referred to as "hydrocolloids", and can include, but are not limited to, polysaccharides such as carboxymethyl starch, carboxymethyl cellulose, and/or hydroxypropyl cellulose; nonionic types such as polyvinyl alcohol, and/or polyvinyl ethers; cationic types such as polyvinyl pyridine, polyvinyl morpholine, N,-dimethylaminoethyl and/or N,-diethylaminopropyl acrylates and/or methacrylates, and/or the respective quaternary salts thereof. In one aspect of this embodiment, the superabsorbent gelling polymers typically include carboxyl groups. These polymers include, but are not limited to, hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and/or slightly network crosslinked polymers of partially neutralized polyacrylic acid. These polymers can be used either solely or in the form of a mixture of two or more different polymers. In another and/or alternative aspect of this embodiment, the polymer materials used in making the superabsorbent gelling polymers typically are slightly network crosslinked polymers of partially neutralized polyacrylic acids and starch derivatives thereof. One nonlimiting example is hydrogel-forming absorbent polymers that comprise from about 50 to about 95%, typically about 75%, neutralized, slightly network crosslinked, polyacrylic acid. In still another and/or alternative aspect of this embodiment, the superabsorbent material can be or include polymeric, hydrophilic absorbent foams that are obtained by polymerizing a high internal phase water-in-oil emulsion (commonly referred to as HIPEs). These foams are readily tailored to provide varying physical properties (e.g., pore size, capillary suction, density, etc.) that affect fluid handling ability. As such, these materials are particularly useful, either alone or in combination with other such foams and/or with fibrous structures, in providing the overall capacity required by superabsorbent material. In still yet another and/or alternative aspect of this embodiment, the absorbent layer comprises at least about 5% by weight of the absorbent layer, typically at least about 15%, more typically at least about 20%, still more typically at least about 25%. In a further embodiment, the cleaning wipe or cleaning pad can include chemically stiffened cellulosic fibers. As used herein, the term "chemically stiffened cellulosic fibers" means cellulosic fibers that have been stiffened by chemical means to increase the stiffness of the fibers under dry and/or aqueous conditions. Such means can include, but is not limited to, the addition of a chemical stiffening agent that coats and/or impregnates the fibers. Such means can also and/or alternatively include the stiffening of the fibers by altering the chemical structure (e.g., crosslinking polymer chains). In one aspect of this embodiment, where the fibers are at least partially used as the absorbent and/or adsorbent layer (or a constituent component thereof), the fibers can be combined with a thermoplastic material. Upon melting, at least a portion of this thermoplastic material can migrate to the intersections of the fibers, typically due to interfiber capillary gradients. These intersections can become bond sites for the thermoplastic material. When cooled, the thermoplastic materials at these intersections solidify to form the bond sites that can hold the matrix and/or web of fibers together in each of the respective layers. This can be beneficial in providing additional overall integrity to the cleaning pad or cleaning wipe. Thermoplastic materials useful in the present invention can be in any of a variety of forms including, but are not limited to, particulates and/or fibers. Suitable thermoplastic materials can be made from any then-noplastic polymer that can be melted at temperatures that will not extensively damage the fibers that comprise the primary web or matrix of each layer. Generally, the melting point of the thermoplastic material will be less than about 190° C., and typically between about 75° C. and about 175° C.; however, other temperature ranges can be used. In any event, the melting point of the thermoplastic material should be no lower than the temperature at which the thermally bonded absorbent structures, when used in the cleaning pads or cleaning wipes, are likely to be stored. In still a further and/or alternative embodiment of the present invention, the cleaning wipes and/or pads can have an attachment layer that allows the wipe and/or pad to be connected to an implement's handle or the support head of various implements. The attachment layer is used in those embodiments where the absorbent and/or adsorbent layer is not suitable for attaching the wipe and/or pad to the support head of the handle. The attachment layer can also function as a mechanism to inhibit or prevent fluid flow through the top surface (e.g., the handle-contacting surface) of the cleaning wipe and/or pad, and/or can provide enhanced integrity of the wipe and/or pad. In one aspect of this embodiment, the attachment layer can consist of a mono-layer or a multi-layer structure. In another and/or alternative aspect of this embodiment, the attachment layer can comprise a surface which is capable of being mechanically attached to the handle's support head by use of a hook and loop system. In one specific design, the attachment layer can comprise at least one surface which is mechanically attachable to hooks that are affixed to the bottom surface of the handle's support head. In a further and/or alternative embodiment, the liquid loading capacity of the cleaning wipe or pad is sufficient to retain the desired amount of improved cleaning composition on the cleaning wipe or pad. In one aspect of this embodiment, the liquid loading capacity of the cleaning wipe or pad is at least about 10% of the dry weight of the cleaning wipe or pad. In another and/or alternative aspect of this embodiment, the liquid loading capacity of the cleaning wipe or pad is about 50%-1000% of the dry weight of the cleaning wipe or pad. This loading capacity is expressed as loading ½ to 10 times the weight (or, more accurately, the mass) of the dry cleaning wipe or pad. In still another and/or alternative aspect of this embodiment, the liquid loading capacity of the cleaning wipe or pad is about 200%-800% of the dry weight of the cleaning wipe or pad. In yet another and/or alternative aspect of this embodiment, the liquid loading capacity of the cleaning wipe or pad is about 250%-500% of the dry weight of the cleaning wipe or pad. In still yet another and/or alternative aspect of this embodiment, the liquid loading capacity of the cleaning wipe or pad is about 300%-450% of the dry weight of the cleaning wipe or pad. In still a further and/or alternative embodiment, the improved cleaning composition is impregnated, dosed, loaded, metered, and/or otherwise dispensed onto the cleaning wipe or pad. The loading of the cleaning wipe or pad can be accomplished in several ways including, but not limited to, treating each individual wipe or pad with a discrete amount of improved cleaning composition, mass treating a continuous web of cleaning wipes with the improved cleaning composition, soaking the entire web of cleaning wipes in the improved cleaning composition, spraying the improved cleaning composition in a stationary or moving web of cleaning wipes, and/or impregnating a stack of individually cut and sized cleaning wipes or pad in a container and/or a dispenser. In yet a further and/or alternative embodiment, the cleaning wipe or pad has a density of about 0.01-1,000 grams per square meter (referred to as "basis weight"). In one aspect of this embodiment, the cleaning wipe or pad has a density of about 25-120 grams/m$^2$. In still yet a further and/or alternative embodiment, the cleaning wipe or pad is produced as a sheet or web which is cut, die-cut or otherwise sized into the desired appropriate shape and size. In another and/or alternative embodiment, the cleaning wipe or pad has a wet tensile strength of at least about 25-250 Newton/m. In one aspect of this embodiment, the cleaning wipe or pad has a wet tensile strength of about 25-250 Newton/m. In another and/or alternative aspect of this embodiment, the cleaning wipe or pad has a wet tensile strength of about 75-170 Newton/m. Manufacturers of cleaning wipes that can be used in the present invention include, but are not limited to, Kimberly-Clark, E.I. Du Pont de Nemours and Company, Dexter, American Nonwovens, James River, BBA Nonwoven, and PGI. Specific, nonlimiting examples of cleaning wipes from these manufacturers are disclosed in Bouchette et al., U.S. Pat. Nos. 4,781,974 and 4,615,937; Clark et al, U.S. Pat. No. 4,666,621; Amundson et al., WO 98/03713; Cabell et al., U.S. Pat. No. 5,908,707; Mackey et al., WO 97/40814; Mackey et al., WO 96/14835; and Moore, EP 750063, all of which are incorporated herein by reference.

In another and/or alternative aspect of the present invention, the cleaning wipe or pad can be individually sealed with a heat-sealable and/or glueable thermoplastic overwrap such as, but not limited to, polyethylene, Mylar and the like. In one embodiment, the cleaning wipes or pads are packaged as numerous, individual sheets or pads which are at least partially, impregnated with the improved cleaning composition of the present invention. In another and/or alternative embodiment, the cleaning wipes are at least partially formed as a continuous web during the manufacturing process and loaded into a dispenser such as, but not limited to, a canister with a closure or a tub with closure. The closure is at least partially used to seal the loaded cleaning wipes from the external environment and/or prevent premature volatilization of the components of the improved cleaning composition. In one aspect of this embodiment, the dispenser includes a plastic such as, but not limited to, high density polyethylene, polypropylene, polycarbonate, polyethylene pterethalate (PET), polyvinyl chloride (PVC), and/or other rigid plastic. In another aspect and/or alternative of this embodiment, the continuous web of cleaning wipes is at least partially threaded through an opening in the top of the dispenser. In still another and/or alternative aspect of this embodiment, the dispenser includes a severing arrangement to cut at least a portion of the cleaning wipe after being at least partially removed from the dispenser. The severing arrangement can include, but is not limited to, a knife blade, serrated edge, and/or the like. In still yet another and/or alternative aspect of this embodiment, the continuous web of cleaning wipes can be scored, folded, segmented, and/or partially cut into uniform and/or non-uniform sizes, and/or lengths. In a further and/or alternative aspect of this embodiment, the cleaning wipes can be interleaved so that the removal of one cleaning wipe advances the next in the opening of the dispenser.

In yet another and/or alternative aspect of the present invention, a kit is provided for cleaning which kit includes the improved cleaning composition of the present invention. The kit can have an assembly of one or more units, either packaged together or separately. For example, the kit can include cleaning pads and/or wipes, and a container of the improved cleaning composition. A second example is a kit with cleaning pads and/or wipes, implement and a container of the improved cleaning composition. A third example is a kit with a refill (concentrated or unconcentrated), a container of ready to use improved cleaning composition, and cleaning pads and/or wipes that include a superabsorbent material. In one embodiment, the implement that includes a cleaning pad and/or wipe that includes a superabsorbent material, and when used with the improved cleaning composition provides effective cleaning and good particulate soil removal. In one aspect of this embodiment, the cleaning pad and/or wipe is a disposable and/or does not require rinsing. In another and/or alternative embodiment, the cleaning pad and/or wipe is detachably mounted on the implement. In one aspect of this embodiment, the cleaning pad and/or wipe can be removed and replaced by another cleaning pad and/or wipe. This is especially useful, when the cleaning pad and/or wipe is excessively soiled. The cleaning pad and/or wipe can be removed and replaced with a fresh cleaning pad and/or wipe. In still another and/or alternative aspect of this embodiment, the implement includes a dosing device. The dosing device at least partially delivers the improved cleaning composition to the surface to be cleaned and/or applies at least a portion of the improved cleaning composition on the cleaning pad and/or wipe. The dosing device can be battery powered, electrically powered, or hand powered. In still yet another and/or alternative embodiment, a reservoir is provided that is designed to at least partially hold the improved cleaning composition. In one aspect of this embodiment, the reservoir is detachably mounted on the implement. In another and/or alternative aspect of this embodiment, the reservoir is used in combination with a dosing device.

In yet another and/or alternative aspect of the present invention, the improved cleaning composition can be at least partially loaded onto an absorbent and/or adsorbent material by a user prior to cleaning. The absorbent and/or adsorbent material can include cleaning wipes, sponges (e.g., cellulose, synthetic, etc.), paper towels, napkins, cleaning pads, cloths, towels, rags, mop heads, and/or the like. In such applications, the improved cleaning composition is not preloaded or fully preloaded onto an absorbent and/or adsorbent material, thus the cleaning composition is at least partially applied by the user just prior to and/or during the cleaning process. When the improved cleaning composition is used in such application, the improved cleaning composition is typically packaged in a separate container or receptacle from the absorbent and/or adsorbent material. During the cleaning process, the improved cleaning composition is applied to the absorbent and/or adsorbent material. Additionally or alternatively, the cleaning composition can be applied to the surface to be cleaned and the absorbent and/or adsorbent material is used to pickup cleaning composition off the surface to be cleaned and/or spread the cleaning composition on the surface to be cleaned. The improved cleaning composition can be applied automatically and/or manually applied to the absorbent and/or adsorbent material and/or onto the surface to be cleaned.

In still another and/or alternative aspect of the present invention, the improved cleaning composition can be applied to a surface to be cleaned prior to exposing the improved cleaning composition to an absorbent and/or adsorbent material. The absorbent and/or adsorbent material can include cleaning wipes, sponges (e.g., cellulose, synthetic, etc.), paper towels, napkins, cleaning pads, cloths, towels, rags, mop heads, and/or the like. In such applications, the improved cleaning composition is not preloaded onto an absorbent and/or adsorbent material, but applied by the user to a surface to be cleaned and then wiped up by the absorbent and/or adsorbent material. The improved cleaning composition can be applied automatically and/or manually applied to the surface to be cleaned.

In still yet another and/or alternative aspect of the present invention, the improved cleaning composition can be applied and/or added to a surface and/or environment to be cleaned without ever applying the cleaning composition to an absorbent and/or adsorbent material. Examples of such uses of the improved cleaning composition include, but are not limited to, air fresheners, shampoos, hand lotions/cleaners, cleaners for cleaning internal components of machinery and/or process lines, carpet fresheners, carpet cleaners, cat litter, drain cleaners, toilet cleaners, environment cleaners (e.g., fumigation gas and/or fluid, liquid spray, etc.), and/or the like.

In still another and/or alternative aspect of the present invention, the improved cleaning composition includes an effective amount of biocide to obtain the desired disinfecting, sanitizing, and/or sterilizing qualities of the improved cleaning composition. The improved cleaning composition includes one or more biocides to achieve the desired disinfecting, sanitizing, and/or sterilizing qualities of the improved cleaning composition. The improved cleaning composition is typically formulated to partially or completely kill microorganisms such as, but not limited to, bacteria, fungi, molds, mildew, and/or viruses. The antimicrobial efficacy of the improved cleaning composition can be tailored for a particular household, industrial and/or institutional application, and/or can be formulated to disinfect sanitize, and/or sterilize surfaces in household, industrial and/or institutional environments. In one embodiment, the biocide in the improved cleaning composition is a cationic biocide. Such cationic biocide includes, but not limited to, quats and/or biguanide compounds. In another and/or alternative embodiment, the biocide in the improved cleaning composition includes a cationic biocide and at least one other type of biocide.

In still yet another aspect of the present invention, the improved cleaning composition includes a cationic biocide that includes one or more biguanide compounds. Biguanide compounds are capable of imparting a broad spectrum antimicrobial and/or germicidal properties to the improved cleaning composition. Biguanide compounds have also been found to be less of an irritant to skin than other types of biocides. The use of biguanide compounds in the improved cleaning composition has further been found to form less residue and exhibit less streaking on a cleaned surface. In one aspect of this embodiment, the one or more biguanide compounds that can be included in the improved cleaning composition include, but are not limited to, compounds having the following general formula:

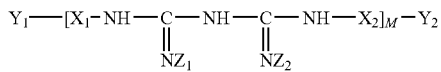

wherein $X_1$ and $X_2$ are either a hydrogen or any aliphatic, cycloaliphatic, aromatic, substituted aliphatic, substituted aromatic, heteroaliphatic, heterocyclic, and/or heteroaromatic compound. $X_1$ and $X_2$ can be the same or different. $Y_1$ and $Y_2$ are any aliphatic, cycloaliphatic, aromatic, substituted aliphatic, substituted aromatic, heteroaliphatic, heterocyclic, and/or heteroaromatic compound. $Y_1$ and $Y_2$ can be the same or different. M is an number equal to or greater than 1. Typically, M has an average value such that the molecular weight biguanide compounds is about 1000-1400; however, the molecular can be higher or lower. Generally M is about 2-20. $Z_1$ and $Z_2$ are either a hydrogen or a salt. $Z_1$ and $Z_2$ can be the same of different. In another and/or alternative aspect of this embodiment, the above-mentioned organic materials can be modified to include a thiol group in their structure so as to allow for the bonding of the compound to a metallic substrate, and/or may be derivatized with other functional groups to permit direct immobilization on a non-metallic substrate. In still another and/or alternative aspect of this embodiment, the above-mentioned organic materials may also be suitably functionalized to incorporate groups such as, but not limited to, hydroxy, amine, halogen, epoxy, alkyl and/or alkoxy silyl functionalities to enable direct immobilization to a surface. In yet another and/or alternative aspect of this embodiment, the salt can include, but is not limited to, salts with an inorganic acid such as, but not limited to, hydrochloride, hydrofluoride, nitrate, sulfate and/or phosphate, and/or salts with an organic acid such as, but not limited to, carboxylic acid, acetate, benzoate, tartrate, adipate, lactate, formate, maleate, glutamate, ascorbate, citrate, gluconate, oxalate, succinate, pamoate, salicylate, isethionate, succinamate, mono-diglycollate, dimethanesulfonate, di-isobutyrate, and/or glucoheptonate. Specific examples of these compounds include, but are not limited to, polyhexamethylene biguanide hydrochloride, p-chlorophenyl biguanide, and 4-chlorobenzhydryl biguanide. In still yet another and/or alternative aspect of this embodiment, the biguanide compound includes, but is not limited to, halogenated hexidine such as, but not limited to, chlorhexidine (1,1'-hexamethylene-bis-5-(4-chlorophenyl biguanide) and its salts. The salts include, but are not limited to, salts with an inorganic acid, such as hydrochloride, hydrofluoride, nitrate, sulfate and/or phosphate, and/or salts with an organic acid such as, but not limited to, carboxylic acid, acetate, benzoate, tartrate, adipate, lactate, formate, maleate, glutamate, ascorbate, citrate, gluconate, oxalate, succinate, pamoate, salicylate, isethionate, succinamate, mono-diglycollate, dimethanesulfonate, di-isobutyrate, and/or glucoheptonate. Examples of salts of chlorhexidine include, but are not limited to, chlorhexidine diphosphanilate, chlorhexidine digluconate, chlorhexidine diacetate, chlorhexidine dihydrochloride, chlorhexidine dichloride, chlorhexidine gluconate, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-valerate, chlorhexidine dicaproate, chlorhexidine malonate, chlorhexidine succinate, chlorhexidine malate, chlothexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Additional examples of biguanide compounds which can be used in the improved cleaning composition are disclosed in U.S. Pat. Nos. 2,684,924; 2,990,425; 3,468,898; 4,022,834; 4,053,636; 4,198,392; 6,143,244; 6,143,281; and 6,153,568; EPC 24,031; and DE 1,964,196; DE 2,212,259; and DE 2,627,548, which are incorporated herein by reference. In another and/or alternative embodiment, the biguanide compound content of the improved cleaning composition can be greater than about 0.02 weight percent of the improved cleaning composition when the biguanide compound functions as the primary biocide in the improved cleaning composition. As can be appreciated, when other biocides are included with the biguanide compound in the improved cleaning composition, the biguanide compound content can be lower than about 0.02 weight percent of the improved cleaning composition. A biguanide compound content of lower than about 0.02 weight percent, when the biguanide compound functions as the primary biocide in the improved cleaning composition, may not eliminate a majority of common microorganisms (e.g., bacteria, viruses, etc.) when exposed to the improved cleaning composition. The upper limit of the biguanide compound content of the improved cleaning composition can be significantly greater than about 0.02 weight percent; however, the biguanide compound content is typically limited by economic cost considerations, local, state and/or federal regulatory restrictions, formula solubility requirements, streaking and residue properties of the improved cleaning composition, skin irritation considerations, and/or the intended use of the improved cleaning composition. Typically, the biguanide compound content of the improved cleaning composition is no more than about 5 weight percent. A biguanide compound content that exceeds about 5 weight percent generally results in the final product having a prohibitive cost since the biguanide compound is typically one of the higher costing component of the improved cleaning composition. In addition, a biguanide compound content exceeding about 5 weight percent may be subject to strict local, state and/or federal regulations due to the toxicity of the improved cleaning composition. However, absent the cost and regulatory barriers, the biguanide compound content can exceed about 5 weight percent when the improved cleaning composition is used in applications which require a high biguanide compound content. In this respect, the biguanide compound content can be up to or exceed about 20 weight percent of the cleaning composition. The concentration of the biguanide compound in the improved cleaning composition may also exceed about 5 weight percent when the improved cleaning composition is in a concentrated form, thus intended to be diluted prior to use. In one aspect of this embodiment, the biguanide compound content of the improved cleaning composition is about 0.05-5 weight percent. In another aspect of this embodiment, the biguanide compound content of the improved cleaning composition is about 0.08-5 weight percent. In still another aspect of this embodiment, the biguanide compound content of the improved cleaning composition is about 0.1-2 weight percent. In yet another aspect of this embodiment, the biguanide compound content of the improved cleaning composition is about 0.1-1 weight percent. In still yet another aspect of this embodiment, the biguanide compound content of the improved cleaning composition is about 0.15-0.8 weight percent. In a further aspect of this embodiment, the biguanide compound content of the improved cleaning composition is about 0.175-0.6 weight percent. In yet a further aspect of this embodiment, the biguanide compound content of the improved cleaning composition is about 0.2-0.5 weight percent. In still a further aspect of this embodiment, the biguanide compound content of the improved cleaning composition is about 0.25-0.4 weight percent.

In yet another and/or alternative aspect of the present invention, the improved cleaning composition includes a cationic biocide that includes one or more quats. The cationic biocide in the improved cleaning composition can primarily include one or more quats, and/or include one or more other cationic biocides in combination with the one or more quats. Such other cationic biocides include, but are not limited to, biguanide compounds. Similar to biguanide compounds, quats are also capable of imparting a broad spectrum antimicrobial or germicidal properties to the improved cleaning composition. In another and/or alternative embodiment, the general structure for the one or more quats that can be included in the improved cleaning composition is:

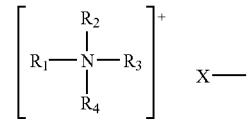

wherein X is an anion such as, but not limited to, a halide, acetate, nitrite, a lower alkosulfate, carbonate and/or an alkyl carboxylate; and $R_1$-$R_4$ are straight chain, branched chain and/or cyclic chain groups. $R_1$-$R_4$ can be the same or different. In one aspect of this embodiment, one or more of the quats included in the improved cleaning composition have at least one higher molecular weight group and at least one lower molecular weight group linked to a common, positively charged nitrogen atom. The one or more higher molecular weight groups include, but are not limited to, higher alkyl groups containing about 6-30 carbon atoms that are branched, unbranched, saturated and/or unsaturated. The one or more lower molecular weight groups include, but are not limited to, 1-12 carbon atoms that are branched, unbranched, saturated, and/or unsaturated. Specific lower molecular weight substituents include, but are not limited to, alkyls of 1 to 4 carbon atoms (e.g., methyl and ethyl), alkyl ethers, hydroxyalkyls, and/or benzyls. One or more of the higher and/or lower molecular weight substituents can include, or can be replaced by, an aryl moiety. Specific aryl moieties include, but are not limited to, benzyl, ethyl benzyl and/or phenyl. In another and/or alternative aspect of this embodiment, an electrically balancing anion (counterion) is linked to the positively charged nitrogen atom. Specific anions include, but are not limited to, bromide, sulfate, iodide, alkycarboxylate, methosulfate, ethosulfate, phosphate, carboxylic acid, or chloride. In still another and/or alternative aspect of this embodiment, specific quats that can be used in the cleaning formulation include, but are not limited to, alkyl ammonium halides such as lauryl trimethyl ammonium chloride and dilauryl dimethyl ammonium chloride; alkyl aryl ammonium halides such as octadecyl dimethyl benzyl ammonium bromide; ethyl dimethyl stearyl ammonium chloride, trimethyl stearyl ammonium chloride, trimethyl cetyl ammonium chloride, dimethyl ethyl lauryl ammonium chloride, dimethyl propyl myristyl ammonium chloride, dinonyl dimethyl ammonium chloride, didecyl dimethyl ammonium chloride, diundecyl dimethyl ammonium chloride, didecyl dimethyl ammonium chloride, dinonyly ethyl ammonium chloride, dimethyl ethyl benzyl ammonium chloride, 3-(trimethyxyosilyl) propyldidecylmethyl ammonium chloride, 3-(trimethoxysilyl) propyloctadecycdimethyl ammonium chloride, dimethyl dioctyl ammonium chloride, didecyl dimethyl ammonium chloride, didodecyl dimethyl ammonium chloride, dimethyl ditetradecyl ammonium chloride, dihexadecyl dimethyl ammonium chloride, dimethyl dioctadecyl ammonium chloride, decyl dimethyl octyl ammonium chloride, dimethyl dodecyloctyl ammonium chloride, benzyl decyl dimethyl ammonium chloride, benzyl dimethyl dodecyl ammonium chloride, benzyl dimethyl tetradecyl ammonium chloride, decyl dimethyl (ethyl benzyl) ammonium chloride, decyl dimethyl (dimethyl benzyl)-ammonium chloride, (chlorobenzyl)-decyl dimethyl ammonium chloride, decyl-(dichlorobenzyl)-dimethyl ammonium chloride, benzyl didecyl methyl ammonium chloride, benzyl didocyl methyl ammonium chloride, benzyl ditetradecyl methyl ammonium chloride, benzyl dodecyl ethyl methyl ammonium chloride, and/or the like. Some examples of commercially available quats that can be included in the improved cleaning composition include, but are not limited to, didecyl dimethyl ammonium chloride, available as BTC 1010 from Stepan Chemical Co.; di(C6-C14)alkyl di(C1-4 alkyl and/or hydroxyalkl) quaternary ammonium compounds such as BARDAC 2250 from Lonza, Inc.; FMB 210-15 from Huntington; Maquat 4450-E from Mason; dialkyl dimethyl ammonium chloride available as BTC 818 from Lonza, Inc.; FMB 302 and Maquat 40 from Mason; alkyl dimethyl benzyl ammonium chloride available as BTC 835 and BARQUAT MB-50 from Lonza, Inc.; FMB 451-5 and MC 1412 from Mason, alkyldimethylbenzyl ammonium chlorides such as the commercially available Barquat MB-50 from Lonza; N-(3-chloroallyl) hexaminium chlorides such as Dowicide and Dowicil available from Dow; benzethonium chloride such as Hyamine from Rohm & Haas; methylbenzethonium chloride represented by Hyamine IOX supplied by Rohm & Haas; and/or cetylpyridinium chloride such as Cepacol chloride available from of Merrell Labs. Examples of dialkyl quaternary compounds are di(C8-C12) dialkyl dimethyl ammonium chloride such as didecyldimethylammonium chloride, and dioctyldimethylammonium chloride (BARDAC 2050). Other cationic antimicrobial actives that can be used in the improved cleaning compositon include, but are not limited to, diisobutylphenoxyethoxyethyl dimethylbenzyl ammonium chloride, commercially available as Hyamine 1622 from Lonza. Some quats are sold as mixtures of two or more different quats. Examples of these commercially available quat mixtures include, but are not limited to, twin chain blend/alkyl benzyl ammonium chloride compounds available as BARDAC 205M, BARDAC 208M, BARQUAT 4250, and BARQUAT 4250Z from Lonza, Inc.; as BTC 885, BTC 888, BTC 2125M and BTC 2250 from Stepan Chemical Co.; as FMB 504 and FMB 504-8 from Huntington; and as MQ 615M and MQ 624M from Mason. In another and/or alternative embodiment, the quat content of the improved cleaning composition is greater than about 0.04 weight percent of the improved cleaning composition when the quat functions as the primary biocide in the improved cleaning composition. As can be appreciated, when other biocides are included with the one or more quats in the improved cleaning composition, the quat content can be lower than about 0.04 weight percent of the improved cleaning composition. A quat content of lower than about 0.04 weight percent, when the quat functions as the primary biocide in the improved cleaning composition, may not eliminate a majority of common microorganisms when exposed to the improved cleaning composition. The upper limit to the quat content of the improved cleaning composition can be significantly greater than about 0.04 weight percent; however, the quat content is typically limited by economic cost considerations, local, state and/or federal regulatory restrictions, formula solubility requirements, streaking properties of the improved cleaning composition, skin irritation considerations, and/or the intended use of the improved cleaning composition. Typically, the quat content of the improved cleaning composition is no more than about 5 weight percent. A quat content that exceeds about 5 weight percent generally results in the final product having a prohibitive cost since the quat is typically one of the higher costing components of the improved cleaning composition. In addition, a quat content exceeding about 5 weight percent may be subject to strict local, state and/or federal regulations due to the toxicity of the improved cleaning composition. However, absent the cost and regulatory barriers, the quat content can exceed about 5 weight percent when the improved cleaning composition is used in applications which require a high quat content. The concentration of the quat in the improved cleaning composition may also exceed about 5 weight percent when the improved cleaning composition is in a concentrated form, thus intended to be diluted prior to use. In one aspect of this embodiment, the quat content of the improved cleaning composition is about 0.05-5 weight percent. In another aspect of this embodiment, the quat content of the improved cleaning composition is about 0.08-5 weight percent. In still another aspect of this embodiment, the quat content of the improved cleaning composition is about 0.1-2 weight percent. In yet another aspect of this embodiment, the quat content of the improved cleaning composition is about 0.1-1 weight percent. In still yet another aspect of this embodiment, the quat content of the improved cleaning composition is about 0.15-0.8 weight percent. In a further aspect of this embodiment, the quat content of the improved cleaning composition is about 0.175-0.6 weight percent. In yet a further aspect of this embodiment, the quat content of the improved cleaning composition is about 0.2-0.5 weight percent. In still a further aspect of this embodiment, the quat content of the improved cleaning composition is about 0.25-0.4 weight percent. In still another embodiment, when one or more quats are combined with one or more biguanide compounds to function as the primary biocide in the improved cleaning composition, the quat content is about 0.001-5 weight percent of the improved cleaning composition and the biguanide compound content is also about 0.001-5 weight percent of the improved cleaning composition. The specific quantities of the quat and biguanide compounds in the improved cleaning composition is typically a function of economic cost considerations; local, state and/or federal regulatory restrictions; formula solubility requirements; streaking and residue properties of the improved cleaning composition; skin irritation considerations; and/or the intended use of the improved cleaning composition. In one specific aspect of this embodiment, the biguanide compound content is greater than the quat content in the improved cleaning composition. In another specific aspect of this embodiment, the biguanide compound content is less than the quat content in the improved cleaning composition. In yet anther specific aspect of this embodiment, the biguanide compound content is about equal to the quat content in the improved cleaning composition.

In yet another and/or alternative aspect of the present invention, the improved cleaning composition includes and/or is used in combination with one or more additional biocides used in combination with the biguanide compound and/or quat. Such biocides can include, but are not limited to, alcohols, peroxides, boric acid and borates, chlorinated hydrocarbons, organometallics, halogen-releasing compounds, mercury compounds, metallic salts, pine oil, organic sulfur compounds, iodine compounds, silver nitrate, quaternary phosphate compounds, and/or phenolics.

In still another and/or alternative aspect of the present invention, the improved cleaning composition includes and/or is used in combination with an effective amount of one or more surfactants. The inclusion of the surfactant in the improved cleaning composition and/or used in combination with the improved cleaning composition can improve the cleaning performance of the improved cleaning composition (e.g., improve wetting properties of the improved cleaning composition, stabilize components in the improved cleaning composition, function as an emulsifying agent, reduce filming and/or streaking, etc). A variety of surfactants can be used in and/or use in combination with the improved cleaning composition. Such surfactants include, but are not limited to, nonionic, semi-polar, anionic, cationic, zwitterionic, and/or amphoteric surfactants. Many of these surfactants are described in *McCutcheon's Emulsifiers and Detergents* (1997), *Kirk-Othmer, Encyclopedia of Chemical Technology*, 3rd Ed., Volume 22, pp. 332-432 (Marcel-Dekker, 1983), and *McCutcheon's Soaps and Detergents* (N. Amer. 1984), the contents of which are hereby incorporated by reference. Typically the surfactant is partially or fully soluble in water. In one embodiment, the surfactant includes, but is not limited to, glycoside, glycols, ethylene oxide and mixed ethylene oxide/propylene oxide adducts of alkylphenols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, sorbitan monooleates, alkanolamides, soaps, alkylbenzene sulfonates, olefin sulfonates, paraffin sulfonates, propionic acid derivatives, alcohol and alcohol ether sulfates, phosphate esters, amines, amine oxides, alkyl sulfates, alkyl ether sulfates, sarcosinates, sulfoacetates, sulfosuccinates, cocoamphocarboxy glycinate, salts of higher acyl esters of isethionic acid, salts of higher acyl derivatives of taurine or methyltaurine, phenol poly ether sulfates, higher acyl derivatives of glycine and methylglycine, alkyl aryl poly-ether alcohols, salts of higher alkyl substituted imadazolinium dicarboxylic acids, ferchorics, tannics, naphthosulfonates, monochloracetics anthraflavinics, hippurics, anthranilics, naphthoics, phthalics, carboxylic acid salts, acrylic acids, phosphates, alkylamine ethoxylates, ethylenediamine alkoxylates, betaines, sulfobetaines, and/or imidazolines. In one aspect of this embodiment, the surfactant includes, but is not limited to, lauryl sulfate, laurylether sulfate, cocamidopropylbetaine, alkyl polyglycosides, and/or amine oxides. In another and/or alternative aspect of this embodiment, the surfactant includes an amine oxide. In still another and/or alternative aspect of this embodiment, the surfactant includes an amine oxide having the general formula:

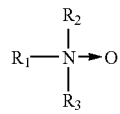

wherein $R_1$ is a $C_{6-30}$ alkyl, and $R_2$ and $R_3$ are $C_{1-6}$ alkyl or hydroxyalkyl. $R_2$ and $R_3$ can be the same of different. These amine oxides can be ethoxylated and/or propoxylated. One specific amine oxide includes, but is not limited to, alkyl di (hydroxy lower alkyl) amine oxides, alkylamidopropyl di (lower alkyl) amine oxides, alkyl di (lower alkyl) amine oxides, and/or alkylmorpholine oxides, wherein the alkyl group has 5-25 carbons and can be branched, unbranched, saturated, and/or unsaturated. Nonlimiting examples of amine oxides include, but are not limited to, lauryl amine oxide sold under the name Barlox 12 from Lonza. In yet another and/or alternative aspect of this embodiment, the surfactant includes alkyl polyglycosides. The alkyl polyglycosides in the improved cleaning composition at least partially functions as a cleaning surfactant. The alkyl polyglycosides has also been found to reduce the filming and/or streaking of the improved cleaning composition on a variety of surfaces. The alkyl polyglycosides is typically formed by reacting a sugar with a higher alcohol in the presence of an acid catalyst, or by reacting a sugar with a lower alcohol (e.g., methanol, ethanol, propanol, butanol, etc.) to thereby provide a lower alkyl glycoside, which is then reacted with a higher alcohol. The higher alcohol generally has the formulation $R_1O(R_2O)_xH$; wherein $R_1$ represents a straight or branched alkyl, alkenyl, or alkylphenyl group having from 2 to 30 carbon atoms; $R_2$ represents an alkylene group having from 2 to 20 carbon atoms; and X is a mean value that is 0 to 10. Specific nonlimiting examples of the higher alcohol having a straight or branched alkanol include, but are not limited to, hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and/or 2-octyldecanol; alkenol such as, but not limited to, hexenol, heptenol, octenol, nonenol, decenol, undecenol, dodecenol, tridecenol, tetradecenol, pentadecenol, hexadecenol, heptadecenol and/or octadecenol; and/or alkylphenols such as, but not limited to, octylphenol and/or nonylphenol. These alcohols or alkylphenols can be used either alone or in combination with one another. Further, an alkylene oxide adduct of these alcohols or alkylphenols can be used. The sugar used to form the alkyl glycoside includes, but is not limited to, monosaccharides, oligosaccharides, and/or polysaccharides. Nonlimiting examples of the monosaccharides include, but are not limited to, aldoses such as, but not limited to, allose, altrose, glucose, mannose, gulose, idose, galactose, talose, ribose, arabinose, xylose, and/or lyxose. Nonlimiting examples of the oligosaccharides include, but are not limited to, maltose, lactose, sucrose and/or maltotriose. Nonlimiting examples of the polysaccharides include, but are not limited to, hemicellulose, insulin, dextrin, dextran, xylan, starch and/or hydrolyzed starch. Specific alkyl glycosides that can be used, but are not limited to such formulation, are represented by the following formula: $R_1O(R_2O)_xH_y$ wherein $R_1$ is an alkyl, alkenyl, or alkylphenyl group having from 6 to 30 carbon atoms; $R_2$ is an alkylene group having from 2 to 20 carbon atoms; H is a residual group originating from a reducing sugar having 2 or 10 carbon atoms; X is a mean value that is 0 to 10; and Y is a mean value that is 1 to 10. The carbon groups can be saturated or unsaturated. In one specific aspect, the alkyl glycoside includes an alkyl group having 6-22 carbons. Typically, the alkly group is linear. As can be appreciated, the alkly groups can be branched. Nonlimiting examples of alkyl polyglycosides include, but are not limited to, the APG series alkyl polyglycosides from Cognis (e.g., Glucopon 325). In another and/or alternative embodiment, the surfactant includes, but is not limited to, an ethoxylated alcohol. One type of non-limiting ethoxylated alcohol that can be used is Surfonic L series surfactants by Huntsman. In still another and/or alternative embodiment, the surfactant includes, but is not limited to, a fluorosurfactant. Fluorosurfatants have been found to reduce the surface tension of the components in the improved cleaning composition. The lowered surface tension has been found to result in improved spreading and/or wetting of the improved cleaning composition on a variety of surfaces. In one aspect of this embodiment, the fluorosurfactant facilities in lowering the surface tension of the improved cleaning composition to less than about 40 dyne/cm, typically less than about 30 dyne/cm, more typically less than about 25 dyne/cm, and even more typically about 15-22 dyne/cm. In another and/or alternative aspect of this embodiment, the fluorosurfactant in the improved cleaning composition reduces the amount of filming and/or streaking of the improved cleaning composition. The reduced the amount of filming and/or streaking occurs with or without buffing of the cleaned surface. In still another and/or alternative aspect of this embodiment, the fluorosurfactant includes an ethoxylated nonionic fluorosurfactant. Typically, the surfactant is partially or fully soluble in water. One type of non-limiting ethoxylated nonionic fluorosurfactant that can be used is Zonyl surfactants by DuPont and/or Fluorads from 3M. In still yet another and/or alternative aspect of this embodiment, the fluorosurfactant is used in combination with a buffer to enhance the reduction of filming and/or streaking of the improved cleaning composition. Non-limiting examples of buffers that can be used in combination with the fluorosurfactant include MEA, $NH_4HCO_3$, $NH_4OH$, $NH_4Carbamate$, and/or SLS. In yet another and/or alternative embodiment, the surfactant, when included in and/or used in combination with the improved cleaning composition, is present in an amount of at least about 0.001 weight percent of the improved cleaning composition. The amount of surfactant present in and/or used in combination with the improved cleaning composition is at least partially controlled to reduce the raw material cost of the improved cleaning composition and/or to restrict the dissolved actives which can contribute to residues remaining when the improved cleaning composition is applied to a surface. In one aspect of this embodiment, the surfactant content in and/or used in combination with the improved cleaning composition is about 0.01-10 weight percent. The concentration of the surfactant in and/or used in combination with the improved cleaning composition may exceed 10 weight percent when the improved cleaning composition is in a concentrated form. In another aspect of this embodiment, the surfactant content in and/or used in combination with the improved cleaning composition is about 0.01-5 weight percent. In still another aspect of this embodiment, the surfactant content in and/or used in combination with the improved cleaning composition is about 0.05-5 weight percent. In yet another aspect of this embodiment, the surfactant content in and/or used in combination with the improved cleaning composition is about 0.075-5 weight percent. In still yet another aspect of this embodiment, the surfactant content in and/or used in combination with the improved cleaning composition is about 0.05-3 weight percent. In a further aspect of this embodiment, the surfactant content in and/or used in combination with the improved cleaning composition is about 0.075-2 weight percent. In still a further aspect of this embodiment, the surfactant content in and/or used in combination with the improved cleaning composition is about 0.1-2 weight percent. In yet a further aspect of this embodiment, the surfactant content in and/or used in combination with the improved cleaning composition is about 0.15-1.5 weight percent. In still yet a further aspect of this embodiment, the surfactant content in and/or used in combination with the improved cleaning composition is about 0.2-1.5 weight percent. In another aspect of this embodiment, the surfactant content in and/or used in combination with the improved cleaning composition is about 0.2-1.25 weight percent. In yet another aspect of this embodiment, the surfactant content in and/or used in combination with the improved cleaning composition is about 0.5-1.25 weight percent. In still another aspect of this embodiment, the surfactant content in and/or used in combination with the improved cleaning composition is about 0.1-1 weight percent. In still yet another aspect of this embodiment, the surfactant content in and/or used in combination with the improved cleaning composition is about 0.15-0.8 weight percent. In a further aspect of this embodiment, the surfactant content in and/or used in combination with the improved cleaning composition is about 0.2-0.4 weight percent. In yet a further aspect of this embodiment, the surfactant content in and/or used in combination with the improved cleaning composition is less than about 0.5 weight percent.

In yet another and/or alternative aspect of the present invention, the improved cleaning composition includes and/or is used in combination with an effective amount of biocide release agent. The biocide release agent is at least partially used to increase the amount of cationic biocide released from an absorbent and/or adsorbent material such as, but not limited to, wipes materials, sponges (e.g., cellulose, synthetic, etc.), paper towels, napkins, cleaning pads, cloths, towels, rags, mop heads, and/or the like. The biocide release agent is also and/or alternatively at least partially used to increase the amount of cationic biocide released from an absorbent and/or adsorbent material such as, but not limited to, fabric (e.g., clothing, sheets and/or pillow cases, blankets, quilts, stuffed animals, rugs, shoes, etc.), wood products (e.g., furniture, house structures, food utensils, bowls, serving platters, etc.). The biocide release agent can be included in the cleaning composition and/or combined at a later time with at least a portion of the improved cleaning composition. It has been found that a significant amount of cationic biocide such as, but not limited to, biguanide compounds and quats, are retained on an absorbent and/or adsorbent material during use of the absorbent and/or adsorbent material during cleaning. For instance, over about 60 percent of the biguanide compounds content in a cleaning composition and over about 50 percent of the quat content is typically retained on a cleaning wipe after use of the cleaning wipe. Similar retain levels of the cationic biocides occur on various other absorbent and adsorbent materials. As a result, the cationic biocide content of the prior cleaning solutions was typically increased to compensate for this high retention phenomena. Consequently, the cationic biocide content was typically at least doubled in prior cleaning solutions to ensure that the desired amount of cationic biocide was released from the cleaning wipe. In addition, when a cationic biocide containing cleaning solution was used in conjunction with sponges (e.g., cellulose, synthetic, etc.), paper towels, napkins, cloths, towels, rags, mop heads, and the like, the cationic biocide was also attracted to and retained by the sponges (e.g., cellulose, synthetic, etc.), paper towels, napkins, cloths, towels, rags, mop heads, and the like, thus removing the cationic biocide from the surface to be cleaned thereby reducing the effectiveness of prior cleaning solutions. It has been found that one source of this retention is at least partially related to the cationic properties of the cationic biocide and the anionic properties of the absorbent and/or adsorbent material. Absorbent and/or adsorbent materials such as, but not limited to, cleaning wipes, sponges (e.g., cellulose, synthetic, etc.), paper towels, napkins, cloths, towels, rags, mop heads, and/or the like that include wood pulp, a blend of wood pulp and/or synthetic fibers that are at least partially derived from wood pulp, include several anionic species such as carboxylate groups, ester groups and/or the like. These anionic species tend to bond to the cationic biocide thereby resulting in the cationic biocide being at least partially retained on the cleaning wipe, sponges (e.g., cellulose, synthetic, etc.), paper towels, napkins, cloths, towels, rags, mop heads, and the like. The biocide release agent is at least partially formulated to mitigate or prevent this bonding phenomena thereby enabling the improved cleaning composition to include a lower cationic biocide content without adversely affecting the cleaning properties and/or the disinfecting, sanitizing, and/or sterilizing efficacy of the improved cleaning composition when used in combination with an absorbent and/or adsorbent material. The biocide release agent is at least partially formulated to mitigate or prevent this bonding phenomena thereby enabling the improved cleaning composition to include a lower cationic biocide content without adversely affecting the cleaning properties, and/or the disinfecting, sanitizing, and/or sterilizing efficacy of the improved cleaning composition. In one embodiment, the biocide release agent used with and/or included in the improved cleaning composition includes a cationic compound designed to at least partially compete with the cationic biocide for the anionic species sites on an absorbent and/or adsorbent material thereby causing increased biocide release from the absorbent and/or adsorbent material during use of the absorbent and/or adsorbent material. The biocide release agent at least partially binds with the anionic species sites thereby freeing the cationic biocide from the absorbent and/or adsorbent material and allowing the cationic biocide to be freed from the absorbent and/or adsorbent material. In another and/or alternative embodiment, the biocide release agent is at least partially applied to an absorbent and/or adsorbent material after the cationic biocide has been applied to the absorbent and/or adsorbent material. In one aspect of this embodiment, the improved cleaning composition includes a biocide release agent to at least partially compete with the cationic biocide for the anionic species sites on an absorbent and/or adsorbent material to cause further cationic biocide release from the absorbent and/or adsorbent. At some time after the improved cleaning composition is applied to the absorbent and/or adsorbent material, additional biocide release agent can be applied to the absorbent and/or adsorbent material to cause further increased biocide release from the absorbent and/or adsorbent. In another and/or alternative aspect of this embodiment, the improved cleaning composition substantially does not include a biocide release agent, but such biocide release agent can be applied at the same or subsequent time as the application of the improved cleaning composition that includes cationic biocide. In still another and/or alternative embodiment, one or more biocide release agents used in and/or with the improved cleaning composition are formulated to have a higher affinity for the anionic species sites than the cationic biocide such that the site competition between the cationic biocide and such biocide release agent favors the biocide release agent. In one aspect of this embodiment, the affinity of one or more biocide release agents for the anionic species sites is significantly greater than the affinity of the cationic biocide for the anionic species sites thereby resulting in substantially irreversible bonding of the biocide release agent with the anionic species sites on the absorbent and/or adsorbent material. In yet another and/or alternative embodiment, one or more biocide release agents include a cationic salt. Salts are desirable biocide release agents in that such compounds are generally inexpensive when compared to many types of cationic biocides. A variety of different salts can be used such as, but not limited to, monovalent salts, divalent salts, organic salts, and the like. These salts include, but are not limited to, acetates, acetylides, ammonium salts (excluding quats), arsenates, astatides, azides, bihalide salts, bicarbonates, bisulfides, borides, borohydrides, borohalides, carconates, citrates, cyanates, cyanides, formates, germanates, glycinates, halates, halides, hydrides, hydroselenides, hydrosulphides, hydroxides, imides, metaniobates, metaantalates, metavanadates, nitrates, nitrides, nitrites, oxides, perchlorates, phosphates, phosphonium salts, selenides, selenites, selenates, sulphides, sulphates, ternary salts, tetraalkyl ammonium salts, tellurides, thiocyanates, and/or vanadates. In one aspect of this embodiment, the biocide release agent includes, but is not limited to, potassium citrate, sodium citrate, sodium tartrate, potassium tartrate, potassium lactate, sodium lactate, salicylate salts of sodium and/or potassium, magnesium sulphate, sodium chloride, ammonium chloride, and/or potassium chloride. In still yet another and/or alternative embodiment, a sufficient amount of biocide release agent is included in and/or used with the improved cleaning composition that includes the cationic biocide to reduce the cationic biocide retention on an absorbent and/or adsorbent material (e.g., cleaning wipes, sponges (e.g., cellulose, synthetic, etc.), paper towels, napkins, cloths, towels, rags, mop heads, etc.) to less than about 50%. In one aspect of this embodiment, the improved cleaning composition includes and/or is used with a sufficient amount of biocide release agent to reduce the cationic biocide retention on the absorbent and/or adsorbent material to less than about 45%. In another aspect of this embodiment, the improved cleaning composition includes and/or is used with a sufficient amount of biocide release agent to reduce the cationic biocide retention on the absorbent and/or adsorbent material to less than about 40%. In still another aspect of this embodiment, the improved cleaning composition includes and/or is used with a sufficient amount of biocide release agent to reduce the cationic biocide retention on the absorbent and/or adsorbent material to less than about 35%. In yet another aspect of this embodiment, the improved cleaning composition includes and/or is used with a sufficient amount of biocide release agent to reduce the cationic biocide retention on the absorbent and/or adsorbent material to less than about 30%. In still yet another aspect of this embodiment, the improved cleaning composition includes and/or is used with a sufficient amount of biocide release agent to reduce the cationic biocide retention on the absorbent and/or adsorbent material to less than about 25%. In a further aspect of this embodiment, the improved cleaning composition includes and/or is used with a sufficient amount of biocide release agent to reduce the cationic biocide retention on the absorbent and/or adsorbent material to less than about 20%. In still a further aspect of this embodiment, the improved cleaning composition includes and/or is used with a sufficient amount of biocide release agent to reduce the cationic biocide retention on the absorbent and/or adsorbent material to less than about 15%. In yet a further aspect of this embodiment, the improved cleaning composition includes and/or is used with a sufficient amount of biocide release agent to reduce the cationic biocide retention on the absorbent and/or adsorbent material to less than about 10%. In still yet a further aspect of this embodiment, the improved cleaning composition includes and/or is used with a sufficient amount of biocide release agent to reduce the cationic biocide retention on the absorbent and/or adsorbent material to less than about 5%. In another aspect of this embodiment, the improved cleaning composition includes and/or is used with a sufficient amount of biocide release agent to reduce the cationic biocide retention on the absorbent and/or adsorbent material to less than about 3%. In still another aspect of this embodiment, the improved cleaning composition includes and/or is used with a sufficient amount of biocide release agent to reduce the cationic biocide retention on the absorbent and/or adsorbent material to less than about 1%. In a further and/or alternative embodiment, the biocide release agent is used with and/or is present in the improved cleaning composition such that the biocide release agent has an effective ionic strength to cause a desired amount of cationic biocide to be released from the absorbent and/or adsorbent material (e.g., cleaning wipes, sponges (e.g., cellulose, synthetic, etc.), paper towels, napkins, cloths, towels, rags, mop heads, etc.). In one aspect of this embodiment, the effective ionic strength of the biocide release agent in the improved cleaning composition and/or used in combination with the improved cleaning composition is at least about $5 \times 10^{-3}$ mol/l. It has been found that an ionic strength of less than about $5 \times 10^{-3}$ mol/l does not result in an appreciable increase in cationic biocide release from the absorbent and/or adsorbent material. In another aspect of this embodiment, the effective ionic strength of the biocide release agent in the improved cleaning composition and/or used in combination with the improved cleaning composition is about $5 \times 10^{-3}$-18 mol/l. In still another aspect of this embodiment, the effective ionic strength of the biocide release agent in the improved cleaning composition and/or used in combination with the improved cleaning composition is at least about $1 \times 10^{-2}$ mol/l. In yet another aspect of this embodiment, the effective ionic strength of the biocide release agent in the improved cleaning composition and/or used in combination with the improved cleaning composition is about $1 \times 10^{-2}$-5 mol/l. In still yet another aspect of this embodiment, the effective ionic strength of the biocide release agent in the improved cleaning composition and/or used in combination with the improved cleaning composition is about $2 \times 10^{-2}$-1 mol/l. In a further aspect of this embodiment, the effective ionic strength of the biocide release agent in the improved cleaning composition and/or used in combination with the improved cleaning composition is about $3 \times 10^{-2}$-0.4 mol/l. In yet a further aspect of this embodiment, the effective ionic strength of the biocide release agent in the improved cleaning composition and/or used in combination with the improved cleaning composition is about $4 \times 10^{-2}$-0.2 mol/l. The weight percent of the biocide release agent in the improved cleaning composition and/or used in combination with the improved cleaning composition to achieve a particular ionic strength in the improved cleaning composition is at least partially a function of the molecular weight of the biocide release agent and the ionic strength of the biocide release agent. In yet a further and/or alternative embodiment, the biocide release agent content of the improved cleaning composition and/or the amount of biocide release agent used in combination with the improved cleaning composition is at least about 0.025 weight percent and can constitute up to about 90 weight percent. In one aspect of this embodiment, the biocide release agent content of the improved cleaning composition and/or amount of biocide release agent used in combination with the improved cleaning composition is about 0.03-10 weight percent. In another aspect of this embodiment, the biocide release agent content of the improved cleaning composition and/or amount of biocide release agent used in combination with the improved cleaning composition is about 0.04-5 weight percent. In still another aspect of this embodiment, the biocide release agent content of the improved cleaning composition and/or amount of biocide release agent used in combination with the improved cleaning composition is about 0.08-3 weight percent. In yet another aspect of this embodiment, the biocide release agent content of the improved cleaning composition and/or amount of biocide release agent used in combination with the improved cleaning-composition is about 0.1-2.5 weight percent. In still yet another aspect of this embodiment, the biocide release agent content of the improved cleaning composition and/or amount of biocide release agent used in combination with the improved cleaning composition is about 0.2-2.5 weight percent. In a further aspect of this embodiment, the biocide release agent content of the improved cleaning composition and/or amount of biocide release agent used in combination with the improved cleaning composition is about 0.5-2 weight percent. In still a further aspect of this embodiment, the biocide release agent content of the improved cleaning composition and/or amount of biocide release agent used in combination with the improved cleaning composition is about 0.75-1.8 weight percent.

In still another and/or alternative aspect of the present invention, the improved cleaning composition includes and/or is used in combination with one or more builder detergents. The builder detergent, when used, can increase the effectiveness of the surfactant that is used in and/or used in combination with the improved cleaning composition when a surfactant is included in and/or used in combination with the improved cleaning composition. The builder detergent can also function as a softener and/or a sequestering and buffering agent when used in and/or used in combination with the improved cleaning composition. A variety of builder detergents can be used in and/or used in combination with the improved cleaning composition. Such builder detergents include, but are not limited to, phosphate-silicate compounds, zeolites, alkali metal, ammonium and substituted ammonium polyacetates, mono-, di-, and tri-alkali salts of nitrilotriacetic acid, carboxylates, aluminosilicate materials, silicates, polycarboxylates, zeolites, carbonates, phosphates, bicarbonates, polyphosphates, amines, alkanolamines, aminopolycarboxylates, polyhydroxysulfonates, starch derivatives, ethylenediamine tetraacetate, and/or metal ion sequestrants (e.g., aminopolyphosphonates such as, but not limited to, ethylenediamine tetramethylene phosphonic acid and diethylene triamine pentamethylenephosphonic acid). In one embodiment, the builder detergent includes polyacetate and/or polycarboxylate compounds. In one aspect of this embodiment, the polyacetate and/or polycarboxylate compounds include, but are not limited to, sodium, potassium, lithium, ammonium, and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These builder detergents can also exist either partially or totally in the hydrogen ion form. In another and/or alternative aspect of this embodiment, the builder detergent includes EDTA and/or EDTA salts. When EDTA salts are included in the improved cleaning composition, the EDTA salts can contribute to the release of the cationic biocide from the absorbent and/or adsorbent material when the improved cleaning composition is loaded on and/or is used in combination with the absorbent and/or adsorbent material. The cationic properties of the EDTA salts compete for the anionic species sites on the absorbent and/or adsorbent material thereby causing some cationic biocide to be released from the absorbent and/or adsorbent material. Although the EDTA salts contribute to some cationic biocide release when sufficient amounts of EDTA salts are included in the improved cleaning composition, the amount of cationic biocide release attributable to the EDTA salts is very small due to the low ionic strength of the EDTA salts. Consequently, EDTA salts in the improved cleaning composition are not a substitute for the biocide release agent, and the absence of a biocide release agent from the improved cleaning composition results in little or no measurable reduction in cationic biocide retention from the absorbent and/or adsorbent material. In one specific aspect, the builder agent includes sodium and/or potassium salts of EDTA. In still another and/or alternative embodiment, the builder detergent includes substituted ammonium salts. In one aspect of this embodiment, the substituted ammonium salts include, but are not limited to, ammonium salts of methylamine, dimethylamine, butylamine, butylenediamine, propylamine, triethylamine, trimethylamine, monoethanolamine, diethanolamine, triethanolamine, isopropanolamine, ethylenediamine tetraacetic acid and/or propanolamine. In yet another and/or alternative embodiment, the improved cleaning composition includes and/or is used in combination with at least about 0.001 weight percent builder detergent. In one aspect of this embodiment, the builder detergent content in and/or used in combination with the improved cleaning composition is about 0.01-2 weight percent. The concentration of the builder detergent in and/or used in combination with the improved cleaning composition may exceed about 2 weight percent when the improved cleaning composition is in a concentrated form. In another aspect of this embodiment, the builder detergent content in and/or used in combination with the improved cleaning composition is about 0.01-1 weight percent. In still another aspect of this embodiment, the builder detergent content in and/or used in combination with the improved cleaning composition is about 0.01-0.8 weight percent. In yet another aspect of this embodiment, the builder detergent content in and/or used in combination with the improved cleaning composition is about 0.05-0.75 weight percent. In still yet another aspect of this embodiment, the builder detergent content in and/or used in combination with the improved cleaning composition is about 0.05-0.5 weight percent. In a further aspect of this embodiment, the builder detergent content in and/or used in combination with the improved cleaning composition is about 0.07-0.3 weight percent. In still a further aspect of this embodiment, the builder detergent content in and/or used in combination with the improved cleaning composition is about 0.09-0.25 weight percent.

In still another and/or alternative aspect of the present invention, the improved cleaning composition can include and/or be used in combination with one or more solvents. The solvent can be used to dissolve various components in the improved cleaning composition so as to form a substantially uniformly dispersed mixture. In addition to the dispersion and solubilizing functions of the solvent, the solvent can function as a cleaning agent to help loosen and solubilize compounds such as greasy or oily soils from surfaces, a residue inhibiting agent to help reduce residues left behind on a cleaned surface, a detergent agent to assist in the detergency of the improved cleaning composition, and/or a disinfecting, sanitizing, and/or a sterilizing agent to help eliminate various bacteria and/or viruses on a cleaned surface. The solvent, when used, can be premixed with the other components of the improved cleaning composition or be partially or fully added to the improved cleaning composition after or simultaneously with use. In one embodiment, the solvent is at least partially water soluble and/or a dispersable organic solvent. In another and/or alternative embodiment, the solvent rapidly volatilizes. In one aspect of this embodiment, the solvent has a vapor pressure of at least about 0.001 mm Hg at about 25° C. In another and/or alternative aspect of this embodiment, the solvent volatilizes in no more than about 5 minutes at ambient temperature (about 25° C.) after contact with a surface. In another and/or alternative embodiment, the solvent volatilizes from a surface substantially without leaving a residue. In still another and/or alternative embodiment, the solvent includes, but is not limited to, $C_{1-6}$ alkanols, $C_{1-6}$ diols, $C_{1-10}$ alkyl ethers of alkylene glycols, $C_{3-24}$ alkylene glycol ethers; and discrete amounts of polyalkylene glycols, short chain carboxylic acids, short chain esters, isoparafinic hydrocarbons, mineral spirits, alkylaromatics, terpenes, terpene derivatives, terpenoids, terpenoid derivatives, formaldehyde, and/or pyrrolidones. In one aspect of this embodiment, the alkanol includes, but is not limited to, methanol, ethanol, -propanol, isopropanol, butanol, pentanol, and/or hexanol, and their various positional isomers. In another and/or alternative aspect of this embodiment, the diols include, but are not limited to, methylene, ethylene, propylene and/or butylene glycols. In still another and/or alternative aspect of this embodiment, alkylene glycol ether solvents include, but are not limited to, ethylene glycol monopropyl ether, ethylene glycol monobutyl ether, propylene glycol-propyl ether, propylene glycol monobutyl ether, propylene glycol t-butyl ether, diethylene glycol monoethyl or monopropyl or monobutyl ether, di- or tri-polypropylene glycol methyl or ethyl or propyl or butyl ether, acetate and/or propionate esters of glycol ethers. In yet another and/or alternative aspect of this embodiment, the short chain carboxylic acids include, but are not limited to, acetic acid, glycolic acid, lactic acid and/or propionic acid. In still yet another and/or alternative aspect of this embodiment, the short chain esters include, but are not limited to, glycol acetate, and/or cyclic or linear volatile methylsiloxanes. In a further and/or alternative aspect of this embodiment, water insoluble solvents such as isoparafinic hydrocarbons, mineral spirits, alkylaromatics, terpenoids, terpenoid derivatives, terpenes, and/or terpenes derivatives are mixed with a water soluble solvent when included in the improved cleaning composition. When one or more water insoluble solvents are mixed with one or more water soluble solvents in and/or used in combination with the improved cleaning composition, the weight percentage of the water insoluble solvents in the improved cleaning composition is generally less than about 10 weight percent, typically less than about 5 weight percent, and more typically less than about 1 weight percent of the improved cleaning composition. As can be appreciated, the improved cleaning composition can be a non aqueous cleaner wherein little, if any, water is included in the improved cleaning composition. In such a formulation, weight percentage of the water insoluble solvent can be greater than about 10 weight percent. In one specific aspect, the water insoluble solvent includes, but is not limited to, tertiary alcohols, hydrocarbons (e.g., alkanes), pine-oil, terpinoids, turpentine, turpentine derivatives, terpenoid derivatives, terpinolenes, limonenes, pinenes, terpene derivatives, benzyl alcohols, phenols, and/or their homologues. Certain terpene derivatives that can be used include, but are not limited to, d-limonene, Terpene EX, dipentene and oc-pinene. In still a further and/or alternative aspect of this embodiment, the pyrrolidones include, but are not limited to, N-methyl-2-pyrrolidone, N-octyl-2-pyrrolidone and/or N-dodecyl-2-pyrrolidone. In one particular formulation for the improved cleaning composition, the one or more solvents include, but are not limited to, -propanol, isopropanol, butanol, Dowanol PnB, Dowanol DPnB, Dowanol PM, Dowanol PnP, Dowanol DB, acetone, and/or Hexyl Cellosolve. In one particular improved cleaning composition formulation, the one or more solvents include isopropanol and/or Dowanol PnB. In still another embodiment, the improved cleaning composition includes and/or is used in combination with at least about 0.5 weight percent solvent when solvent is included in the improved cleaning composition. Typically, the improved cleaning composition includes and/or is combined with at least about 0.5 weight percent solvent to avoid solubility problems which can result from the combination of various components of the improved cleaning composition. In one aspect of this embodiment, the solvent content in and/or is combined with the improved cleaning composition is about 0.5-70 weight percent. The concentration of the solvent in and/or is combined with the improved cleaning composition may exceed about 70 weight percent when the improved cleaning composition is in a concentrated form. In another aspect of this embodiment, the solvent content in and/or combined with the improved cleaning composition is about 0.5-30 weight percent. In still another aspect of this embodiment, the solvent content in and/or combined with the improved cleaning composition is about 0.5-10 weight percent. In yet another aspect of this embodiment, the solvent content in and/or combined with the improved cleaning composition is about 0.75-7 weight percent. In still yet another aspect of this embodiment, the solvent content in and/or combined with the improved cleaning composition is about 0.75-6 weight percent. In a further aspect of this embodiment, the solvent content in and/or combined with the improved cleaning composition is about 1-5 weight percent. In still a further aspect of this embodiment, the solvent content in and/or combined with the improved cleaning composition is about 2-4 weight percent. In yet a further aspect of this embodiment, the solvent content in and/or combined with the improved cleaning composition is about 2.5-4 weight percent.

In still yet another and/or alternative aspect of the present invention, the improved cleaning composition includes and/or is used in combination with a high and a low boiling point solvent. As defined herein, a high boiling point solvent is a solvent having a boiling point of at least about 150° C. (302° F.). As defined herein, a low boiling point solvent is a solvent having a boiling point of less than about 150° C. (302° F.). The high and low boiling point solvent is a compound other than water. Other solvents, in addition to one solvent from each category, may be included. In another and/or alternative embodiment, the solvents having a boiling point less than about 150° C. include, but are not limited to, methanol, ethanol, isopropanol, propanol, butyl alcohol, sec-butyl alcohol, isobutyl alcohol, tert-butyl alcohol, pentyl alcohol, tert-pentyl alcohol, 2-pentanol, 3-pentanol, neopentyl alcohol, ethyleneglycol methylether, ethyleneglycol ethylether, ethyleneglycol propylether, propyleneglycol methylether, propyleneglycol ethylether, ethyleneglycol methyletheracetate, and/or propyleneglycol methyletheracetate. In still another and/or alternative embodiment, the solvents having a boiling point greater than or equal to about 150° C. include, but are not limited to, ethylene glycol, propylene glycol, butanediol, methylpropanediol, ethyleneglycol butylether, ethyleneglycol hexylether, ethyleneglycol ethylhexylether, diethyleneglycol methylether, diethyleneglycol ethylether, diethyleneglycol propylether, diethyleneglycol butylether, propyleneglycol propylether, propyleneglycol t-butylether, propyleneglycol butylether, dipropyleneglycol methylether, dipropyleneglycol ethylether, dipropyleneglycol propylether, dipropyleneglycol t-butylether, dipropyleneglycol butylether, tripropyleneglycol methylether, tripropyleneglycol butylether, ethyleneglycol ethyletheracetate, propyleneglycol ethyletheracetate, ethyleneglycol butyletheracetate, propyleneglycol butyletheracetate, diethyleneglycol methyletheracetate, dipropyleneglycol methyletheracetate, diethyleneglycol ethyletheracetate, dipropyleneglycol ethyletheracetate, diethyleneglycol butyletheracetate, dipropyleneglycol butyletheracetate, and/or N-methyl-2-pyrrolidone. In yet another and/or alternative embodiment, the amount of solvent in the dual boiling point solvents used in and/or in combination with the improved cleaning composition that have a boiling point of less than about 150° C. is generally equal to or greater than the amount of solvent having a boiling point greater than or equal to about 150° C. In one aspect of this embodiment, the amount of solvent having a boiling point less than about 150° C. is about equal to the amount of solvent having a boiling point greater than or equal to about 150° C. In another and/or alternative aspect of this embodiment, the ratio of solvent having a boiling point less than about 150° C. to the amount of solvent having a boiling point greater than or equal to about 150° C. is about 10-1:1, typically about 5-1:1, more typically about 2-1:1, and even more typically about 1.5-1:1.

In still yet another and/or alternative aspect of the present invention, the improved cleaning composition includes and/or is used in combination with water. The water, when used, can be premixed with the other components of the improved cleaning composition or be partially or fully added to the improved cleaning composition at the time of or prior to use. The water can include tap water, filtered water, bottled water, spring water, distilled water, deionized water, and/or industrial soft water. The amount of water in and/or combined with the improved cleaning composition depends on whether the improved cleaning composition is an aqueous or nonaqueous composition. In one embodiment, the water used in and/or used in combination with the improved cleaning composition is deionized water and/or industrial soft water. The use of deionized water and/or industrial soft water can reduce the amount of residue formation and can limit the amount of undesirable metal ions in and/or used in combination with the improved cleaning composition. In another and/or alternative embodiment, the improved cleaning composition is an aqueous composition, and the water constitutes at least a majority weight percent of the improved cleaning composition. The amount of water in the improved cleaning composition is typically less when the improved cleaning composition is in a concentrated liquid or semi-liquid form, or in a solid form. In one aspect of this embodiment, the water content in the ready to use improved liquid cleaning composition is at least about 70 weight percent. The term "ready to use" means the improved cleaning composition does not need to be diluted or mixed with water and/or other solvents prior to use, or the concentrated improved cleaning composition has been diluted with water and/or other solvents. In another and/or alternative aspect of this embodiment, the water content in the ready to use improved liquid cleaning composition is at least about 80 weight percent. In still another and/or alternative aspect of this embodiment, the water content in the ready to use improved liquid cleaning composition is at least about 90 weight percent. In yet another and/or alternative aspect of this embodiment, the water content in the ready to use improved cleaning composition is at least about 95 weight percent.

In a further and/or alternative aspect of the present invention, the improved cleaning composition includes and/or is used in combination with one or more anti-dye transfer agents. When the improved cleaning composition is used to clean and/or is used in combination with other cleaners to clean fabrics that include dyes (e.g., clothing, rugs, carpets, curtains, pillows, sheets and/or pillowcases, blankets, etc.), the one or more anti-dye transfer agents in the improved cleaning composition inhibit dry transfer during the cleaning operation. One way of overcoming the dye transfer problem is to at least partially complex or adsorb the fugitive dyes before such dyes have the opportunity to become attached to other articles. The anti-dry transfer agent is formulated to provide anti-dye transfer and color protection properties to the improved cleaning composition without adversely affecting stain or soil removal properties and/or soil redeposition properties of the improved cleaning composition. In one embodiment, the anti-dye transfer agent can include, but is not limited to, polyvinylpyrrolidone; quaternary polyvinylpyrridinium derivatives; polyvinylimidazole; polyvinylpyridine oxide; copolymers of polyvinylpyridine and polyvinylimidazole; vinyl imidazole homo- or copolymer; polyamine oxide; vinylimidazole; vinylpyrrolidone; vinylimidazole; vinylpyridine; dimethylaminoethyl methacrylate; dimethylaminopropylmethacrylamide; poly(4-vinylpyridine-N-oxide); copolymers of vinylpyrrolidone and vinylimidazole; copolymers of polyvinylpyrrolidone and vinylimidazole; copolymers of vinylpyrrolidone and polyvinylimidazole; copolymers vinylimidazole, vinyloxazolidone and/or -vinylpyrrolidone; polymeric compounds based on -vinylpyrrolidone and/or -vinylimidazole and/or -vinyloxazolidone; vinyloxazolidone; and/or poly(vinylpyridine betaines). Several of these anti-dye transfer agents which can be included in and/or used in combination with the improved cleaning composition are disclosed in U.S. Pat. Nos. 6,306,815 and 6,313,086, which are incorporated herein by reference.

In a further and/or alternative aspect of the present invention, the improved cleaning composition includes and/or is used in combination with one or more adjuncts. The adjuncts include, but are not limited to, buffering and pH adjusting agents, fragrances or perfumes, waxes, dyes and/or colorants, solubilizing materials, stabilizers, thickeners, defoamers, hydrotropes, lotions and/or mineral oils, enzymes, bleaching agents, cloud point modifiers, preservatives, ion exchangers, alkalies, anticorrosion materials, antiredeposition materials, optical brighteners, chelating agents, enzymes, whiteners, brighteners, antistatic agents, sudsing control agents, hydrotropes, bleach precursors, soil removal agents, soil release agents, softening agents, opacifiers, inert diluents, graying inhibitors, stabilizers, and/or polymers. In one embodiment, the buffering and pH adjusting agents, when used, include, but are not limited to, organic acids, mineral acids, alkali metal and alkaline earth salts of silicate, metasilicate, polysilicate, borate, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and/or 2-amino-2methylpropanol. The buffering agent can be an active detergent in its own right, and/or can be a low molecular weight, organic or inorganic material used for maintaining the desired pH. The buffer can be alkaline, acidic or neutral. Non-limiting examples of buffering agents include nitrogen-containing materials (e.g., lysine; lower alcohol amines like mono-, di-, and tri-ethanolamine; tri(hydroxymethyl) amino methane; 2-amino-2-ethyl-1,3-propanediol; 2-amino-2-methyl-propanol; 2-amino-2-methyl-1,3-propanol; disodium glutamate; methyl diethanolamide; 2-dimethylamino-2-methylpropanol; 1,3-bis(methylamine)-cyclohexane; 1,3-diamino-propanol N,N'-tetra-methyl-1,3-diamino-2-propanol; N,N-bis(2-hydroxyethyl)glycine; tris (hydroxymethyl)methyl glycine; ammonium carbamate; citric acid; acetic acid; ammonia; alkali metal carbonates; and/or alkali metal phosphates). For additional buffers that can be used, see McCutcheon's EMULSIFIERS AND DETERGENTS, North American Edition, 1997, McCutcheon Division, MC Publishing Company which is incorporated herein by reference. In another and/or alternative embodiment, the waxes, when used, include, but are not limited to, carnauba, beeswax, spermaceti, candelilla, paraffin, lanolin, shellac, esparto, ouricuri, polyethylene wax, chlorinated naphthalene wax, petrolatum, microcrystalline wax, ceresine wax, ozokerite wax, and/or rezowax. In yet another and/or alternative embodiment, the solubilizing materials, when used, include, but are not limited to, hydrotropes (e.g., water soluble salts of low molecular weight organic acids such as the sodium and/or potassium salts of xylene sulfonic acid). In another and/or alternative embodiment, the acids, when used, include, but are not limited to, organic hydroxy acids, citric acids, keto acid, and the like. In still another and/or alternative embodiment, thickeners, when used, include, but are not limited to, polyacrylic acid, xanthan gum, calcium carbonate, aluminum oxide, alginates, guar gum, methyl, ethyl, clays, and/or propylhydroxycelluloses. In yet another and/or alternative embodiment, defoamers, when used, include, but are not limited to, silicones, aminosilicones, silicone blends, and/or silicone/hydrocarbon blends. In still yet another and/or alternative embodiment, lotions, when used, include, but are not limited to, achlorophene and/or lanolin. In a further and/or alternative embodiment, enzymes, when used, include, but are not limited to, lipases, proteases, amylases, cellulases, and/or -peroxidases, and/or hydrotropes such as xylene sulfonates and/or toluene sulfonates. In yet a further and/or alternative embodiment, bleaching agents, when used, include, but are not limited to, peracids, perborates, percarbonates, chlorine-generating substances (e.g., chloroisocyanurates hypohalite sources), hydrogen peroxide, and/or sources of hydrogen peroxide. In still a further and/or alternative embodiment, preservatives, when used, include, but are not limited to, mildewstat of bacteriostat, methyl, ethyl and propyl parabens, short chain organic acids (e.g., acetic, lactic and/or glycolic acids), bisguanidine compounds (e.g., Dantagard and/or Glydant) and/or short chain alcohols (e.g., ethanol and/or IPA). In one aspect of this embodiment, the mildewstat of bacteriostat includes, but is not limited to, mildewstats (including non-isothiazolone compounds) include Kathon GC, a 5-chloro-2- methyl-4-isothiazolin-3-one, Kathon ICP, a 2-methyl-4-isothiazolin-3-one, and a blend thereof, and Kathon 886, a 5-chloro-2-methyl-4-isothiazolin-3-one, all available from Rohm and Haas Company; Bronopol, a 2-bromo-2-nitropropane 1,3diol, from Boots Company Ltd.; Proxel CRL, a propyl-p-hydroxybenzoate, from ICI PLC; Nipasol M, an o-phenyl-phenol, Na+ salt, from Nipa Laboratories Ltd.; Dowicide A, a 1,2-Benzoisothiazolin-3-one, from Dow Chemical Co.; and Irgasan DP 200, a 2,4,4'-trichloro-2-hydroxydiphenylether, from Ciba-Geigy A.G. In still yet a further and/or alternative embodiment, polymers, when used, include, but are not limited to, polysaccharides, polycarboxylates, polystyrenesulfonates, acrylate polymers, polyethyleneimines, polyvinylpyrrolidones, methylvinyl ether, polyvinyl alcohols, silicones, and/or polyethylene glycols. In one aspect of this embodiment, the polymer, when used, is generally a water soluble or dispersable polymer having a molecular weight of generally below 2,000,000 daltons. In another and/or alternative aspect of this embodiment, polysaccharide polymers include, but are not limited to, substituted cellulose materials like carboxymethylcellulose, ethyl cellulose, hydroxyethylcellulose, hydroxypropylcellulose, hydroxymethylcellulose, succinoglycan and naturally occurring polysaccharide polymers like xanthan gum, guar gum, locust bean gum, tragacanth gum or derivatives thereof, sodium casceinate, gelatin, cationic cellulose ether, and/or Polymer JR. In still another and/or alternative aspect of this embodiment, polycarboxylates include, but are not limited to, ethylene, simple olefin, styrene, alphamethylstyrene, methyl, ethyl and $C_{3-8}$ alkyl acrylates and methacrylates, isobornyl methacrylate, acrylamide, hydroxyethyl acrylate and methacrylate, hydroxypropyl acrylate and methacrylate, vinyl pyrrolidone, butadiene, isoprene, vinyl halides such as vinyl chloride and vinylidine chloride, alkyl maleates, alkyl fumarates, acrylic acid, methacrylic acid, polycarboxylic acids, sulfonic acids, phosphoric acids, maleic anhydride, ethylene and/or propylene. In yet another and/or alternative aspect of this embodiment, polystyrenesulfonates include, but are not limited to, Flexan 130, Versa TL-4, and/or Versa TL501 from ALCO Corporation. In still another and/or alternative aspect of this embodiment, acrylate polymers include, but are not limited to, cationic acrylic water soluble polymers that are copolymers of cationic quaternized acrylates, methacrylates, acrylamides, and methacrylamides; and/or copolymers of one or more acidic monomers such as acrylic acid, methacrylic acid or maleic anhydride with at least one other ethylenically unsaturated monomer selected from a group of ethylene and other simple olefin, styrene, alpha-methylstyrene, methyl, ethyl and $C_3$ to $C_8$ alkyl acrylates and methacrylates, isobornyl methacrylate, acrylamide, hydroxyethyl acrylate and methacrylate, hydroxypropyl acrylate and methacrylate, vinyl pyrrolidone, butadiene, isoprene, vinyl halides such as vinyl chloride and vinylidine chloride, alkyl maleates, alkyl fumarates, fumaric acid, maleic acid, itaconic acid, acetoacetoxy methacrylate or other acetoacetate monomers, and/or divinyl or polyvinyl monomers, such as glycol polyacrylates, allyl methacrylate, and divinyl benzene. In a further and/or alternative aspect of this embodiment, polyvinylpyrrolidone includes, but is not limited to, copolymers of vinylpyrrolidone with one or more aklylenically unsaturated monomers such as unsaturated dicarboxylic acids such as maleic acid, chloromaleic acid, fumaric acid, itaconic acid, citraconic acid, phenylmaleic acid, aconitic acid, acrylic acid, methacrylic acid, vinylimidazole, vinylcaprolactam, butene, hexadecene, and vinyl acetate. In addition, any of the esters and amides of the unsaturated acids can be employed, for example, methyl acrylate, ethylacrylate, acrylamide, methacryamide, dimethylaminoethylmethactylate, dimethylaminopropylmethacrylamide, trimethylammoniumethylmethacrylate, and/or trimethylammoniumpropylmethacrylamide. Other suitable alkylencially unsaturated monomers include, but are not limited to, aromatic monomers such as, but not limited to, styrene, sulphonated styrene, alpha-methylstyrene, vinyltoluene, t-butylstyrene and others. In one particular example, the polyvinylpyrrolidone includes a copolymer of vinylpyrrolidone and dimethylaminoethylmethacrylate quaternized with diethylsulfate (e.g., Gafquat HSi, HS-100, 440, 734, 755, 755N, and/or 755N-P by ISP Corp.). The inclusion of polyvinylpyrrolidone enhances the cleaning effectiveness of the cleaning surfactant in the improved cleaning composition without adversely affecting the filming and streaking properties of the improved cleaning composition. Typically, the polyvinylpyrrolidone is a cationic polymer that is combined with a non-ionic surfactant; however, other types of surfactants can be used in combination with the polyvinylpyrrolidone. In yet a further and/or alternative aspect of this embodiment, the silicones include, but are not limited to, polysicoxanes. The inclusion of silicones in the improved cleaning composition can facilitate in enhancing the ease in which the improved cleaning composition can be spread over a surface such as, but not limited to, a hard surface. The increase in ease of spreading can result in the ease in which the improved cleaning composition applied over a surface to be cleaned. The silicone can decrease the static coefficient of friction, thereby resulting in the improved cleaning composition being spread easer by a cleaning pad, wipe, mop, etc. In one particular example, the silicone is a volatile silicone that evaporates upon drying without leaving surface residue and/or a slippery surface. In another and/or alternative particular example, a suspension polymer is used in combination with the silicone in the improved cleaning composition to suspend the silicone in the improved cleaning composition. The suspension polymer typically has a high enough yield stress to at least partially suspend the silicone in the fluid improved cleaning composition. Non-limiting examples of suspension polymers include polyacrylates (e.g., Carbopols from B.F. Goodrich), hydrophobically modifies polyacrylates (e.g., Carbopol and/or Acrysols from Rohn & Haas), polyurethanes, xanthan gum, and/or carboxymethyl cellulose (e.g., Methocels from Dow Chemical). In still a further and/or alternative aspect of this embodiment, the corrosion inhibitors include, but are not limited to, sodium silicate, sodium disilicate, and/or sodium metasilicate. In still a further and/or alternative aspect of this embodiment, the graying inhibitors include, but are not limited to, carboxymethylcellulose, methylcellulose, hydroxypropylmethyl-cellulose, polyacrylic acid, and/or copolymers of acrylic and/or maleic acid. In another and/or alternative aspect of this embodiment, the chelant includes, but are not limited to, ethylenediamine-N, N'-disuccinic acid (EDDS) or the alkali metal, alkaline earth metal, ammonium, and/or substituted ammonium salts thereof. In yet another and/or alternative aspect of this embodiment, the suds suppressors include, but are not limited to, silicones (e.g., alkylated polysiloxane) and/or silica-silicone mixtures (e.g., silica aerogels, xerogels, hydrophobic silicas of various types, etc.). In still another and/or alternative aspect of this embodiment, the antiredeposition and soil suspension agents include, but are not limited to, cellulose derivatives (e.g., methylcellulose, carboxymethylcellulose, hydroxyethylcellulose, homopolymers of acrylic acid, copolymers of maleic acid and acrylic acid, etc.). In still yet another and/or alternative aspect of this embodiment, the optical brighteners include, but are not limited to, disodium 4,4$^1$-bis-(2-diethanolamino-4-anilino-s-triazin-6-ylamino) stilbene-2:2$^1$ disulphonate, disodium 4,-4$^1$-bis-(2-morpholino-4-anilino-s-triazin-6-ylaminostilbene-2:2$^1$-disulphonate, disodium 4,4$^1$-bis-(2,4-dianilino-s-triazin-6-ylamino)stilbene-2:2$^1$-disulphonate, monosodium 4$^1$,4$^{11}$-bis-(2,4-dianilino-s-triazin-6ylamino)stilbene-2-sulphonate, disodium 4,4$^1$-bis-(2-anilino-4-(N-methyl-N-2-hydroxyethylamino)-s-triazin-6-ylamino)stilbene-2,2$^1$-disulphonate disodium 4,4$^1$-bis-(4-phenyl-2,1,3-triazol-2-yl)-stilbene-2, 2$^1$ disulphonate, disodium 4,4$^1$-bis(2-anilino-4-(1-methyl-2-hydroxyethylamino)-s-triazin-6-ylamino)stilbene-2,2$^1$ disulphonate, and/or sodium 2(stilbyl-4$^{11}$-(naphtho-1$^1$,2$^1$:4,5)-1,2,3-triazole-2$^{11}$-sulphonate. In a further and/or alternative aspect of this embodiment, the soil release agents include, but are not limited to, copolymers or terpolymers of terephthalic acid with ethylene glycol and/or propylene glycol, ethoxylated/propoxylated polyamines, modified polyesters (e.g., dimethyl terephtalate, dimethyl sulfoisophtalate, ethylene glycol and 1-2 propane diol, etc.). In still a further and/or alternative aspect of this embodiment, the polymer includes vinylpyrrolidone homo- and copolymers, acrylamide homo- and copolymers, polyvinylalcohol and polyvinylacetate homo- and copolymers, quaternary acrylate and methacrylate copolymers, and/or amphoteric acrylate and methacrylate homo- and copolymers. In one specific example, the polmyer includes polyvinylpyrrolidone compound, and/or quaternary acrylic copolymer. Other various adjuncts that can be included in and/or used in combination with the improved cleaning composition are disclosed in U.S. Pat. Nos. 6,306, 815 and 6,313,086, which are incorporated herein by reference.

In still a further and/or alternative aspect of the present invention, the improved cleaning composition has a neutral or alkaline pH. Various compounds (e.g., adjuncts, biocides, etc.) can be added to and/or used in combination with the improved cleaning composition to control the pH of the improved cleaning composition. In one embodiment, the pH of the cleaning composition is alkaline. In one aspect of this embodiment, the pH of the improved cleaning composition is between about 7-12. In another aspect of this embodiment, the pH of the improved cleaning composition is between about 7.2-10.5.

The principal object of the present invention is to provide an improved cleaning composition having improved cleaning attributes.

Another and/or alternative object of the present invention is to provide an improved cleaning composition having improved disinfecting, sanitizing, and/or sterilizing properties.

Yet another and/or alternative object of the present invention is to provide an improved cleaning composition that can be pre-loaded or post-loaded on an absorbent or absorbent material.

Still another and/or alternative object of the present invention is to provide an improved cleaning composition that exhibits improved cationic biocidal release from an absorbent or absorbent material.

Yet another and/or alternative object of the present invention is to provide an improved cleaning composition that includes a biguanide compound and/or quat as one of the principal disinfecting, sanitizing, and/or sterilizing agents.

Still yet another and/or alternative object of the present invention is to provide an improved cleaning composition having a reduced solvent content.

Another and/or alternative object of the present invention is to provide an improved cleaning composition having a reduced toxicity without impairing the disinfecting, sanitizing, and/or sterilizing attributes of the improved cleaning composition.

Yet another and/or alternative object of the present invention is to provide an improved cleaning composition having a reduced raw material cost.

Still another and/or alternative object of the present invention is to provide an improved cleaning composition that exhibits reduced streaking and/or filming.

A further and/or alternative object of the present invention is to provide an improved cleaning composition that can be used to disinfect, sanitize, and/or sterilize a variety of surfaces.

Still a further and/or alternative object of the present invention is to provide an improved cleaning composition that can to formulated in a concentrated or ready to use form.

Still yet a further and/or alternative object of the present invention is to provide an improved cleaning composition that can be used in conjunction with or separately from an absorbent or adsorbent material.

Another and/or alternative object of the present invention is to provide an improved cleaning composition that can be formed as an aerosol, liquid, semi-liquid or solid form.

Still another and/or alternative object of the present invention is to provide an improved cleaning composition that can be used on hard surfaces.

Another and/or alternative object of the present invention is to provide an improved cleaning composition can be used to clean diningware.

Still yet another and/or alternative object of the present invention is to provide an improved cleaning composition can be used in pet litter.

Another and/or alternative object of the present invention is to provide an improved cleaning composition can be used in soaps, lotions, and/or shampoos.

Still another and/or alternative object of the present invention is to provide an improved cleaning composition that is alkaline.

These and other objects and advantages will become apparent to those skilled in the art upon reading and following the description of the invention taken together with the accompanied drawings.

BRIEF DESCRIPTION OF THE DRAWINGS

Reference may now be made to the drawings, which illustrates various attributes of the invention wherein.

DETAILED DESCRIPTION OF THE PREFERRED EMBODIMENTS

Figure 1:
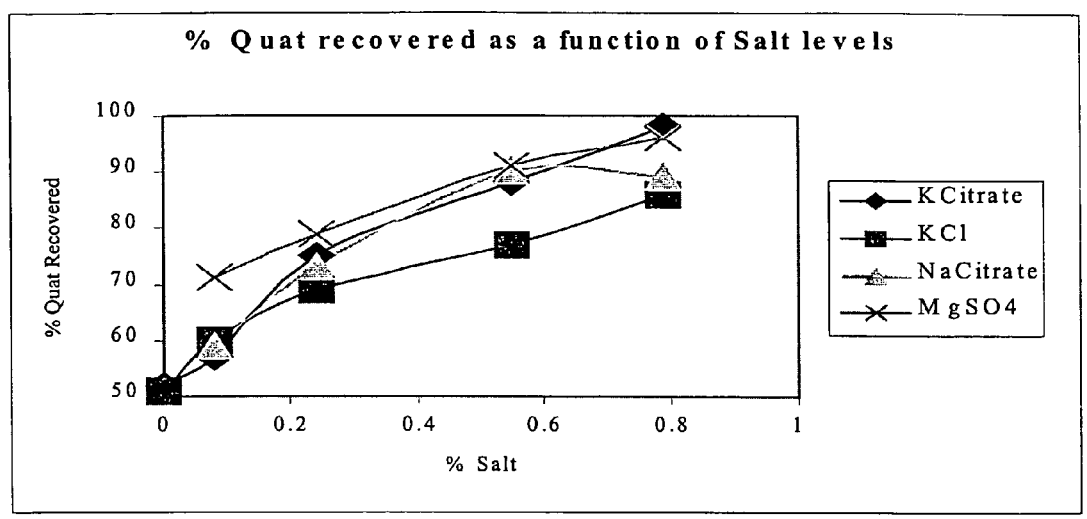
FIG. 1 is a graphical illustration of the percentage of quat recovered from the cleaning wipe as a function of the weight percentage of several different type of salts in the improved cleaning composition.

The improved cleaning composition of the present invention can be used independently from or in conjunction with an absorbent and/or adsorbent material. For instance, the improved cleaning composition is formulated to be used in conjunction with a cleaning wipe, sponge (e.g., cellulose, synthetic, etc.), cleaning pad, paper towel, napkin, cloth, towel, rag, mop head, squeegee, and/or other cleaning device that includes an absorbent and/or adsorbent material. The improved cleaning composition can be formulated to be loaded onto and/or used in combination with an absorbent and/or adsorbent material (e.g., cleaning wipe, cleaning pad, mop head, cloth, towel, etc.) to clean hard surfaces. The improved cleaning composition can also or alternatively be formulated to clean fabrics (e.g., clothing, carpet, curtains, rugs, etc.). The improved cleaning composition can also or alternatively be formulated to disinfect and/or sanitize various areas and things (e.g., rooms, pet litter, medical equipment, etc.) The improved cleaning composition can also or alternatively be formulated for use in personal hygiene products (e.g., hand cleaners, body lotions, shampoos, hair conditioners, etc.).

I. Hard Surface Cleaners

The improved cleaning composition is particular applicable for use with hard surfaces. Such surfaces include, but are not limited to, windows, doors, counter tops, floor, sinks, toilets, showers, kitchen appliances, and the like. When cleaning hard surfaces, an important goal is to not only clean, disinfect, sanitize, and/or sterilize the hard surface, but to also reduce filming and streaking on the hard surface. It is also desirable for the cleaned hard surface to not be sticky. The improved cleaning composition is formulated to clean, disinfect, sanitize, and/or sterilize hard surfaces, and to reduce filming and streaking on the hard surface without leaving a sticky surface on the cleaned hard surface.

The improved cleaning composition can be in concentrated form or ready-to-use form. The improved cleaning composition can be in gas, liquid, paste, gel, or solid form. The improved cleaning composition can be dispensed from a liquid container, an aerosol container, a container for holding crystals or a paste, and the like. The improved cleaning composition can be preloaded onto an absorbent and/or adsorbent material, and/or used in combination with an absorbent and/or adsorbent material.

The basic components of the improved cleaning composition for hard surfaces include:

(I) cationic biocide;

(ii) solvent and/or surfactant.

Additional components can be included in and/or used in combination with the improved cleaning composition to add one or more attributes to the improved cleaning composition and/or to enhance the attributes of the improved cleaning composition.

A. The Cationic Biocide

The biocide in the improved cleaning composition includes a cationic compound. The cationic biocide typically includes one or more biguanide compounds and/or quats. Biguanide compounds are desirable in that such compounds have abroad spectrum antimicrobial or germicidal properties. The biguanide compounds are also less irritating to skin, and produce less streaking and residue when applied to a hard surface. As a result, the improved cleaning composition feels drier after being applied resulting in higher consumer satisfaction. A variety of different biguanide compounds can be used in the improved cleaning composition. The biguanide compounds that can be used in the improved cleaning composition include, but are not limited to, compounds have the following general formula:

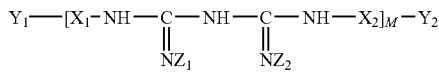

where $X_1$ and $X_2$ are either a hydrogen or any aliphatic, cycloaliphatic, aromatic, substituted aliphatic, substituted aromatic, heteroaliphatic, heterocyclic, and/or heteroaromatic compound. $X_1$ and $X_2$ can be the same or different. $Y_1$ and $Y_2$ are any aliphatic, cycloaliphatic, aromatic, substituted aliphatic, substituted aromatic, heteroaliphatic, heterocyclic, and/or heteroaromatic compound. $Y_1$ and $Y_2$ can be the same or different. M is an number equal to or greater than 1. Typically, M has an average value such that the molecular weight biguanide compounds is about 1000-1400; however, the molecular can be higher or lower. Generally M is about 2-20. $Z_1$ and $Z_2$ are either a hydrogen or a salt. $Z_1$ and $Z_2$ can be the same of different. In addition or alternatively, the biguanide compounds include, but are not limited to, halogenated hexidine and its salts. One particular nonlimiting biguanide compound that can be used in the improved cleaning composition is Vantocil P. The biguanide compound content of the improved cleaning composition is generally maintained at least above 0.0005 weight percent, and more generally above about 0.02 weight percent and less than about 20 weight percent; however, higher or lower biguanide compound contents can be used. Typically, the biguanide compound content of the improved cleaning composition is about 0.1-0.5 weight percent. The weight percentage range for the biguanide compound in the improved cleaning composition is selected to disinfect, sanitize, and/or sterilize most common household, institutional, and industrial hard surfaces. Common types of bacteria that are at least partially destroyed by biguanide compounds in the improved cleaning composition include, but are not limited to, *Staphylococcus aureus* (*Staph*), Kleb, *Salmonella choleraesuis* (*Salmonella*), *Pseudomonas aeruginosa, Pserratia marcescens*, Influenza A2, *Candida albicans, Fusarium solani*, common viruses and/or fungi.

Quats, like biguanide compounds, have a broad spectrum antimicrobial or germicidal properties. A variety of different quats can be used in the improved cleaning composition. The general structure for the one or more quats that can be included in the improved cleaning composition is:

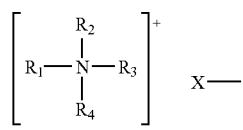

wherein X is an anion such as, but not limited to, a halide, acetate, nitrite, a lower alkosulfate, carbonate and/or an alkyl carboxylate; and $R_1$-$R_4$ are straight chain, branched chain and/or cyclic chain groups. $R_1$-$R_4$ can be the same or different. Nonlimiting types of quat that can be used in the improved cleaning composition include an alkyldimethylbenzylammonium quat, an alkyldimethylethylbenzylammonium quat and/or an alkyldimethylammonium quat. Nonlimiting specific quat that can be used in the improved cleaning composition is a combination of alkyldimethylbenzylammonium chloride ($C_{14}$—60%, $C_{16}$—30%, $C_{12}$—5%, $C_{18}$—5%) and alkyldimethylethylbenzylammonium chloride ($C_{12}$—68%, $C_{14}$—32%); alkyldimethylbenzyl ammonium chlorides such as the commercially available Barquat MB-50 from Lonza; di(C6-C14)alkyl di(C1-4 alkyl and/or hydroxyalkyl) quaternary ammonium compounds such as Bardac 2050 and/or 2250 from Lonza, (3-chloroallyl) hexaminium chlorides such as Dowicide and Dowicil available from Dow; benzethonium chloride such as Hyamine from Rohm & Haas, methylbenzethonium chloride represented by Hyamine IOX supplied by Rohm & Haas, cetylpyridinium chloride such as Cepacol chloride available from of Merrell Labs. This quat combination is commercially available as Barquat 4250 and Barquat 4250Z by Lonza. When one or more quats are included in the improved cleaning composition, the quat content of the improved cleaning composition is typically maintained above about 0.0005 weight percent and less than about 20 weight percent; however, higher or lower quat contents can be used. Generally, the quat content of the improved cleaning composition is less than or equal to the content of the biguanide compound in the improved cleaning composition, when biguanide compounds are included in the improved cleaning composition; however, the quat content can be greater than the biguanide compound content. The weight percentage range for the quat in the improved cleaning composition is selected to disinfect, sanitize, and/or sterilize most common household, institutional, and industrial hard surfaces. Common types of bacteria that are at least partially destroyed by the quat in the improved cleaning composition include, but are not limited to, *Staphylococcus aureus* (*Staph*), Kleb, *Salmonella choleraesuis* (*Salmonella*), *Pseudomonas aeruginosa*, *Pserratia marcescens*, Influenza A2, *Candida albicans*, *Fusarium solani*, common viruses and/or fingi.

B. The Solvent

The solvent used in and/or in combination with the improved cleaning composition is selected to at least partially dissolve into solution the biguanide compound, quat, and/or other organic compounds in the improved cleaning composition. The use of certain solvents can also improve the cleaning, biocidal and/or detergency properties of the improved cleaning composition. Typically, the solvent is water soluble and rapidly volatilizes substantially without leaving a residue, causing streaking, and/or leaving a sticky surface. The solvent also typically has a vapor pressure of at least about 0.001 mm Hg at about 25° C., and volatilizes in no more than about 5 minutes at ambient temperature (about 25° C.) after contact with a surface.

Generally, the one or more solvents include in and/or used in combination with the improved cleaning composition include, but are not limited to, $C_{1-6}$ alkanols, $C_{1-6}$ diols, $C_{1-10}$ alkyl ethers of alkylene glycols, $C_{3-24}$ alkylene glycol ethers, and/or polyalkylene glycols. The solvent content of the improved cleaning composition is generally maintained above about 0.1 weight percent and generally less than about 10 weight percent; however, higher or lower solvent contents can be used. Typically, the solvent content of the improved cleaning composition is about 0.5-5 weight percent. The lower solvent weight percentages are especially desirable in jurisdictions wherein regulations require solvent concentrations of less than about 4-10 weight percent in the improved cleaning composition.

Various solvent combinations in the improved cleaning composition can also facilitate in the reduction of filming and/or streaking. One particular solvent combination that results in reduced filming and/or streaking is a solvent combination that includes a high and a low boiling point solvent combination. As can be appreciated, the improved cleaning composition does not require the use of such a solvent combination. In addition, when two of more solvents are included in the improved cleaning composition, all the solvents can be high or low boiling point solvents. However, the present invention contemplates the added improvement of using a high and a low boiling point solvent in the improved cleaning composition. Solvents having a boiling point of less than about 150° C. that can be used in the improved cleaning composition include, but are not limited to, methanol, ethanol, isopropanol, propanol, butl alcohol, sec-butyl alcohol, isobutyl alcohol, tert-butyl alcohol, pentyl alcohol, tert-pentyl alcohol, 2-pentanol, 3-pentanol, neopentyl alcohol, allyl, crotyl, methylvinyl-carbinol, ethyl ether, -propyl ether, isopropyl ether, -butyl ether, vinyl ether, allyl ether, ethyleneglycol methylether, ethyleneglycol ethylether, ethyleneglycol propylether, propyleneglycol methylether, propyleneglycol ethylether, ethyleneglycol methyletheracetate, and/or propyleneglycol methyletheracetate. Solvents having a boiling point greater than or equal to about 150° C. that can be used in the improved cleaning composition include, but are not limited to, ethylene glycol, propylene glycol, butanediol, methylpropanediol, ethyleneglycol butylether, ethyleneglycol hexylether, ethyleneglycol ethylhexylether, diethyleneglycol methylether, diethyleneglycol ethylether, diethyleneglycol propylether, diethyleneglycol butylether, propyleneglycol-propylether, propyleneglycol t-butylether, propyleneglycol-butylether, dipropyleneglycol methylether, dipropyleneglycol ethylether, dipropyleneglycol-propylether, dipropyleneglycol t-butylether, dipropyleneglycol-butylether, tripropyleneglycol methylether, tripropyleneglycol-butylether, ethyleneglycol ethyletheracetate, propyleneglycol ethyletheracetate, ethyleneglycol butyletheracetate, propyleneglycol butyletheracetate, diethyleneglycol methyletheracetate, dipropyleneglycol methyletheracetate, diethyleneglycol ethyletheracetate, dipropyleneglycol ethyletheracetate, diethyleneglycol butyletheracetate, dipropyleneglycol butyletheracetate, and/or N-methyl-2-pyrrolidone.

The amount of solvent in the dual boiling point solvents having a boiling point less than about 150° C. is generally equal to or greater than the solvent having a boiling point greater than or equal to about 150° C.

C. The Surfactant

The surfactant used in and/or in combination with the improved cleaning composition is selected to improve the cleaning performance of the improved cleaning composition. The surfactant can also reduce the amount of perceived filming and/or streaking of the improved cleaning composition. The surfactant also can provide detergency to the improved cleaning composition to facilitate in the removal of soil from the hard surface. The surfactant also can reduce the amount of redeposition of soils onto the hard surface.

Generally the surfactant includes, but is not limited to, at least one lauryl sulfate, laurylether sulfate, cocamidopropylbetaine, alkyl polyglycoside, ethoxylated alcohol, fluorosurfactant, and/or amine oxide. In one particular formulation, the surfactant in and/or used in combination with the improved cleaning composition includes alkyl polyglycosides, ethoxylated alcohol, fluorosurfactant and/or amine oxides. One particular not limiting example of alkyl polyglycosides, ethoxylated alcohol, fluorosurfactant and/or amine oxides that can be included in the improved cleaning composition are amine oxides sold under the brand Barlox by Lonza, alkyl polyglycosides sold under the brand APG by Cognis, ethoxylated alcohol sold under the Surfonic by Huntsman, and/or fluorosurfactant sold under the brand Zonyl by DuPont. The surfactant content in and/or used in combination with the improved cleaning composition is generally at least about 0.001 weight percent of the improved cleaning composition, typically at least about 0.05 weight percent and less than about 10 weight percent of the improved cleaning composition, and more typically about 0.06-2 weight percent of the improved cleaning composition.

D. The Absorbent and/or Adsorbent Material

The improved cleaning composition, when used to clean hard surfaces, is generally used in conjunction with one or more absorbent and/or adsorbent materials. The improved cleaning composition can be sprayed and/or poured onto a hard surface to be cleaned and an absorbent and/or adsorbent material such as, but not limited to, a sponge, mop head, cloth, towel, and the like is then used to spread the improved cleaning composition on the hard surface and/or clean the hard surface. Additionally or alternatively, the improved cleaning composition is at least partially loaded on the absorbent and/or adsorbent material prior to the absorbent and/or adsorbent material at least partially applying the improved cleaning composition onto the hard surface and/or cleaning the hard surface.

The present invention also contemplates the pre-loading of the improved cleaning composition on a cleaning pad and/or cleaning wipe. The cleaning pad or cleaning wipe typically includes wood pulp and/or wood pulp derivatives; however, this is not required. The improved cleaning composition on the cleaning pad or cleaning wipe is typically in a ready to use liquid form; however, the improved cleaning composition can be in a concentrate in liquid, semi-liquid or solid form on the cleaning pad or cleaning wipe. Typically, the cleaning wipe has at least one layer of nonwoven material. The cleaning pad can also included one or more layers of nonwoven material. Nonlimiting examples of commercially available cleaning wipes that can be used include DuPont 8838, Dexter ZA, Dexter 10180, Dexter M10201, Dexter 8589, Ft. James 836, and Concert STD60LN. All of these cleaning wipes include a blend of polyester and wood pulp. Dexter M10201 also includes rayon, a wood pulp derivative. The cleaning pad or cleaning wipe can be used by-itself and/or in combination with another device such as, but not limited to, a mop. The cleaning pad typically has an absorbent capacity, when measured under a confining pressure of 0.09 psi after 20 minutes, of at least about 1 g deionized water per g of the cleaning pad. The cleaning pad will also typically have a total fluid capacity (of deionized water) of at least about 100 g. However, the absorbency and/or fluid capacity of the cleaning pad can vary depending on the desired use of the cleaning pad. The cleaning wipe can have the same or different amount of absorbency.

The cleaning wipe or pad can contain a superabsorbent material to enhance the absorbency and/or fluid capacity of the cleaning pad or cleaning wipe. When superabsorbent material is included in the cleaning pad or cleaning wipe, the cleaning pad or cleaning wipe will typically comprise at least about 1% by weight of the cleaning pad or cleaning wipe, and more typically at least about 5%.

The cleaning pad or cleaning wipe can also include materials to stiffen the cleaning pad or cleaning wipe. Such materials include, but are not limited to, chemically stiffened cellulosic fibers.

The cleaning pad or cleaning wipe can also include a thermoplastic material to at least partially bind together the adsorbent and/or adsorbent fibers in the cleaning pad or cleaning wipe. The thermoplastic material can also enhance the integrity of the cleaning pad or cleaning wipe.

The loading ratio of the improved cleaning composition onto the cleaning wipe or cleaning pad can be about 2-5:1, and typically about 3-4:1; however, other loading rations can be used. The improved cleaning composition can be loaded onto the cleaning wipe and/or cleaning pad in any number of manufacturing methods. Typically, the cleaning wipe or cleaning pad is soaked in the improved cleaning composition for a period of time until the desired amount of loading is achieved.

The cleaning pad or cleaning wipe can also have an attachment layer that allows the cleaning pad or cleaning wipe to be connected to and/or disconnected from an implement's handle or the support head or an implement (e.g., mop, broom, etc.). The attachment layer can also function to prevent fluid flow through the top surface (e.g., the handle-contacting surface) of the cleaning pad or cleaning wipe, and/or can further provide enhanced integrity for the cleaning pad or cleaning wipe.

The cleaning pad or cleaning wipe can also be part of a cleaning kit. The kit can have an assembly of one or more units, either packaged together or separately. The kit can comprise an implement containing a cleaning pad or cleaning wipe that may or may not include a superabsorbent material, and the improved cleaning composition. The cleaning pad or cleaning wipe can be detachably mounted on the implement so that the cleaning pad or cleaning wipe can be removed and/or replaced with a fresh clean pad or cleaning wipe. The implement can also include a dosing device that delivers the improved cleaning composition on the cleaning pad or cleaning wipe and/or on the hard surface to be cleaned. The dosing device can be battery powered, electrically powered, or hand powered. The implement can also have a reservoir that contains the improved cleaning composition. The reservoir can be refillable or contain a non-refillable amount of improved cleaning composition. The reservoir can also be detachably mounted on the implement to allow for easy refilling or replacing with a filled reservoir.

E. Water

The improved cleaning composition typically includes water. When the improved cleaning composition is a liquid, water based, ready-to-use cleaner, the water content of the improved cleaning composition is generally over 50 weight percent of the improved cleaning composition. Typically, the liquid ready-to-use improved cleaning composition includes at least about 80 weight percent water; however, higher or lower water contents can be used. When the improved cleaning composition is a liquid, non-water based, ready-to-use cleaner, the water content of the improved cleaning composition is generally less than about 30 weight percent of the improved cleaning composition, and typically less than about 15 weight percent of the improved cleaning composition. The water used in the improved cleaning composition is typically deionized water and/or industrial soft water so as to reduce residue formation and limit the amount of undesirable metal ions in the improved cleaning composition; however, other types of water can be used (e.g., tap water, spring water, filtered water, etc.).

F. Biocide Release Agent

When the improved cleaning composition is loaded onto an absorbent or adsorbent material, and/or is to be used with an absorbent or adsorbent material, a biocide release agent is typically included in and/or used with the improved cleaning composition to improve the release of the biguanide compound, quat, and/or other cationic biocides in the improved cleaning composition from the absorbent and/or adsorbent material. The biocide release agent used in the improved cleaning composition typically includes a cationic compound designed to compete with the cationic biocide (e.g., biguanide compound, quat, etc.) for anionic species sites on the absorbent and/or adsorbent material (e.g., sponges (e.g., cellulose, synthetic, etc.), paper towels, cleaning pads, cleaning wipes, napkins, cloths, towels, rags, mop heads, squeegee). The cationic biocide release agent typically includes a cationic salt. Generally, a commonly available salt is used so as to minimize the raw material cost of the improved cleaning composition. In addition, a salt having a relatively high ionic strength per mole of salt is selected to minimize the amount of salt needed in the improved cleaning composition so as to also minimizing the raw material cost of the improved cleaning composition. Nonlimiting examples of salts that can be used as a biocide release agent in and/or in combination with the improved cleaning composition include potassium citrate, sodium citrate, magnesium sulphate, sodium chloride, ammonium chloride, and/or potassium chloride. Generally, the one or more salts are added to and/or used in combination with the improved cleaning composition in an amount to cause over about 50% of the cationic biocide to be released from the an absorbent or adsorbent material when used to clean a hard surface. Generally, the ionic strength of the one or more salts that make up the biocide release agent used in and/or used in combination with the improved cleaning composition is about $1\times10^{-2}$-2 mol/l, and the weight percent of the salt used in and/or in combination with the improved cleaning composition is about 0.04-5 weight percent.

G. Additional Anti-Microbial Compound

One or more additional anti-microbial compounds can be included in and/or used in combination with the improved cleaning composition to enhance the biocidal efficacy of the improved cleaning composition. Such anti-microbial compounds include, but are not limited to, diisobutylphenoxyethoxyethyl dimethylbenzyl ammonium chloride, commercially available as Hyamine 1622 from Lonza. Other anti-microbial compounds include, but are not limited to, alcohols, peroxides, boric acid and borates, chlorinated hydrocarbons, organometallics, halogen-releasing compounds, mercury compounds, metallic salts, pine oil, essential oils, organic sulfur compounds, iodine compounds, silver nitrate and other silver compounds, quaternary phosphate compounds, and/or phenolics.

H. Polymer

Various types of polymers can also be included in and/or used in combination with the improved cleaning composition. These polymers are typically added to the improved cleaning composition to enhance the detergency of the improved cleaning composition, improved wetting of the improved cleaning composition, and/or reduce filming and/or streaking of the improved cleaning composition. The polymers, when used, include, but are not limited to, polysaccharides, polycarboxylates, polystyrenesulfonates, acrylate polymers, polyethyleneimines, polyvinylpyrrolidones, polymethylvinyl ether, polyvinyl alcohols, silicones, polyethylene glycols, and/or copolymers thereof. Polymers that have improved the detergency of the improved cleaning composition include, but are not limited to a copolymer of vinylpyrrolidone and dimethylaminoethylmethacrylate quaternized with diethylsulfate (e.g., Gafquat HSi, HS-100, 440, 734, 755, 755N, and/or 755N-P by ISP Corp.), and/or quaternary acrylic copolymer (e.g., Syntran HX52-1-1 (Interpolymer)). The inclusion of these polymers has been found to enhance the cleaning effectiveness of the cleaning surfactant (e.g., alkylpolyglucosides, etc.) in the improved cleaning composition without significantly adversely affecting the filming and streaking properties of the improved cleaning composition.

I. Buffer/Builder

A builder detergent can be included in and/or be used in combination with the improved cleaning composition. The builder detergent, when used, typically increases the detergency effectiveness of the surfactant in the improved cleaning composition. The builder detergent can also or alternatively function as a softener, a sequestering, and/or buffering agent in the improved cleaning composition. A variety of builder detergents can be used in the improved cleaning composition.

J. Additional Adjuvants

The improved cleaning composition can includes and/or be used in combination with one or more additional adjuncts. The adjuncts include, but are not limited to, fragrances or perfumes, waxes, dyes and/or colorants, solubilizing materials, stabilizers, thickeners, defoamers, hydrotropes, lotions and/or mineral oils, enzymes, bleaching agents, cloud point modifiers, and/or preservatives.

A general formulation of the improved cleaning composition in weight percent for hard surface cleaning is as follows:

| | |
|---|---|
| Cationic Biocide | 0.02-20% |
| Surfactant | at least about 0.01% |
| Water | less than about 99.95% |

Several specific, nonlimiting, examples of the improved cleaning composition in weight percent are as follows:

Example 1

| | |
|---|---|
| Cationic Biocide | 0.02-10% |
| Solvent | 0-99% |
| Surfactant | 0.001-10% |
| Builder detergent | 0-10% |
| Polymer | 0-20% |
| Biocide release agent | 0-10% |
| Water | 0-99.95% |

Example 2

| | |
|---|---|
| Cationic Biocide | 0.02-5% |
| Solvent | 0-20% |
| Surfactant | 0.001-5% |
| Builder detergent | 0-2% |
| Polymer | 0-10% |
| Biocide release agent | 0-5% |
| Water | at least 68% |

Example 3

| | |
|---|---|
| Cationic Biocide | 0.05-5% |
| Solvent | 0.5-70% |
| Surfactant | 0.001-5% |
| Builder detergent | 0.001-2% |
| Polymer | 0-5% |
| Biocide release agent | 0.03-10% |
| Water | at least 10% |

Example 4

| | |
|---|---|
| Cationic Biocide | 0.04-2% |
| Solvent | 0.04-10% |
| Surfactant | 0.01-5% |
| Builder detergent | 0-2% |
| Polymer | 0.01-2% |
| Biocide release agent | 0-2.5% |
| Water | at least 78.5% |

Example 5

| | |
|---|---|
| Cationic Biocide | 0.1-2% |
| Solvent | 2-30% |
| Surfactant | 0.05-3% |
| Builder detergent | 0.01-2% |
| Polymer | 0.1-1% |
| Biocide release agent | 0.08-3% |
| Water | at least 60% |

Example 6

| | |
|---|---|
| Cationic Biocide | 0.1-2% |
| Solvent | 0.1-5% |
| Surfactant | 0.1-4% |
| Builder detergent | 0-1% |
| Polymer | 0.1-1% |
| Biocide release agent | 0-2% |
| Water | at least 86% |

Example 7

| | |
|---|---|
| Cationic Biocide | 0.3-0.4% |
| Solvent | 3.5-5% |
| Surfactant | 0.2-0.4% |
| Builder detergent | 0.09-0.15% |
| Polymer | 0.1-1% |
| Biocide release agent | 0.09-1.1% |
| Fragrance | 0-1% |
| Water | at least 90% |

Example 8

| | |
|---|---|
| Cationic Biocide | 0.15-0.8% |
| Solvent | 2-10% |
| Surfactant | 0.075-2% |
| Builder detergent | 0.01-0.8% |
| Polymer | 0.1-1% |
| Biocide release agent | 0.1-2.5% |
| Water | at least 80% |

Example 9

| | |
|---|---|
| Cationic Biocide | 0.1-1% |
| Solvent | 0.1-5% |
| Surfactant | 0.1-4% |
| Builder detergent | 0-1% |
| Polymer | 0.1-1% |
| Biocide release agent | 0-2% |
| Water | at least 87% |

Example 10

| | |
|---|---|
| Cationic Biocide | 0.2-0.5% |
| Solvent | 2.75-8% |
| Surfactant | 0.15-0.8% |
| Builder detergent | 0.05-0.5% |
| Polymer | 0.1-1% |
| Biocide release agent | 0.5-2% |
| Water | at least 85% |

Example 11

| | |
|---|---|
| Vantocil P | 0.1-0.5% |
| Isopropanol | 1.5-5% |
| PnB (glycol ether) | 0.5-2% |
| APG 325 | 0.25-1.5% |
| Ammonium Chloride | 0-1% |
| Dipotassium EDTA | 0-0.5% |
| Gafquat 440 | 0-0.8% |
| Fragrance | 0-1% |
| Water | at least 89.5% |

Example 12

| | |
|---|---|
| Vantocil P | 0.15-0.4% |
| Isopropanol | 1.75-4% |
| PnB (glycol ether) | 0.5-1.5% |
| APG 325 | 0.25-1% |
| Ammonium Chloride | 0.05-1% |
| Dipotassium EDTA | 0-0.3% |
| Gafquat 440 | 0.1-0.8% |
| Fragrance Oil | 0-1% |
| Water | at least 90.8% |

Example 13

| | |
|---|---|
| Cationic Biocide | 0.25-0.4% |
| Solvent | 2.75-5% |
| Surfactant | 0.2-0.4% |
| Builder detergent | 0.075-0.25% |
| Gafquat 440 | 0.1-0.8% |
| Biocide release agent | 0.75-1.8% |
| Water | at least 85% |

Example 14

| | |
|---|---|
| Vantocil P | 0.3-0.5% |
| Isopropanol | 3-5% |
| Lauryl Dimethyl Amine Oxide | 0.2-0.4% |
| Sodium Citrate | 0.9-1.1% |
| DiPotassium EDTA | 0.09-0.15% |
| Gafquat 440 | 0.1-0.8% |
| Fragrance | 0-1% |
| Water | at least 90% |

Example 15

| | |
|---|---|
| Barquat 4250Z/Vantocil P | 0.3-0.4% |
| Isopropanol | 3.5-5% |
| Lauryl Dimethyl Amine Oxide | 0.2-0.4% |
| Disodium EDTA | 0.09-0.15% |
| Gafquat 440 | 0-0.8% |
| Potassium Citrate | 0.9-1.1% |
| Water | at least 90% |

Example 16

| | |
|---|---|
| BTC 2250/Vantocil P | 0.3-0.4% |
| Isopropanol | 3.5-5% |
| Lauryl Dimethyl Amine Oxide | 0.2-0.4% |
| DiPotassium EDTA | 0.09-0.15% |
| Gafquat 440 | 0-0.8% |
| Sodium Citrate | 0.9-1.1% |
| Water | at least 90% |

Example 17

| | |
|---|---|
| BTC 2250 | 0.05-0.4% |
| Vantocil P | 0.05-0.4% |
| Isopropanol | 0.1-5% |
| PnB (glycol ether) | 0-2% |
| APG 325 | 0-2% |
| Lauryl Dimethyl Amine Oxide | 0-1% |
| DiPotassium EDTA | 0-0.5% |
| Gafquat 440 | 0-0.8% |
| Sodium Citrate | 0.2-2% |
| Water | at least 90% |

Example 18

| | |
|---|---|
| Vantocil P | 0.1-0.4% |
| Isopropanol | 1.5-4% |
| Lauryl Dimethyl Amine Oxide | 0-1% |
| PnB (glycol ether) | 1-2% |
| Ammonium Chloride | 0.05-0.4% |
| DiPotassium EDTA | 0.3-0.5% |
| Gafquat 440 | 0-0.8% |
| Fragrance | 0-1% |
| Water | at least 90% |

Example 19

| | |
|---|---|
| Vantocil P | 0.05-0.6% |
| Isopropanol | 1-3% |
| Dowanol PnP | 0.5-2% |
| Lauryl Dimethyl Amine Oxide | 0-1% |
| PnB (glycol ether) | 0-2% |
| APG 325 | 0.05-1% |
| DiPotassium EDTA | 0-0.5% |
| Gafquat 440 | 0.05-0.5% |
| Ammonium Chloride | 0-0.4% |
| Fragrance | 0-0.5% |
| Water | at least 92% |

Example 20

| | |
|---|---|
| Vantocil P | 0.05-0.5% |
| Isopropanol | 1-3% |
| Dowanol PnP | 0.75-1.5% |
| Lauryl Dimethyl Amine Oxide | 0-1% |
| PnB (glycol ether) | 0-1% |
| APG 325 | 0.1-0.5% |
| DiPotassium EDTA | 0-0.5% |
| Gafquat 440 | 0.05-0.4% |
| Ammonium Chloride | 0-0.4% |
| Fragrance | 0-0.5% |
| Water | at least 94% |

Several specific, nonlimiting examples of the improved cleaning composition loaded onto a cleaning wipe in weight percentage of the loaded cleaning wipe are as follows:

Example 21

| | |
|---|---|
| Cationic Biocide | 0.01-4.167% |
| Solvent | 0.01-16.67% |
| Surfactant | 0-4.167% |
| Builder detergent | 0-1.67% |
| Polymer | 0-8.33% |
| Biocide release agent | up to 4.167% |
| Water | at least 34% |
| Dry cleaning wipe | 16.7-50% |
| Loading ratio | 1-5:1 | wherein the ionic strength of the biocide release agent is at least about $5 \times 10^{-3}$ mol/l.

Example 22

| | |
|---|---|
| Cationic Biocide | 0.025-4.167% |
| Solvent | 0.25-58.3% |
| Surfactant | 0.0005-4.167% |
| Builder detergent | 0.0005-1.67% |
| Polymer | 0-4.167% |
| Biocide release agent | 0.015-8.33% |
| Water | at least 5% |
| Dry cleaning wipe | 16.7-50% |
| Loading ratio | 1-5:1 | wherein the ionic strength of the biocide release agent is at least about $5\times10^{-3}$ mol/l.

Example 23

| | |
|---|---|
| Cationic Biocide | 0.067-0.8% |
| Solvent | 0.067-4% |
| Surfactant | 0-3.2% |
| Builder detergent | 0-0.8% |
| Polymer | 0-2.083% |
| Biocide release agent | up to 1.6% |
| Water | at least 58% |
| Dry cleaning wipe | 20-33% |
| Loading ratio | 2-4:1 | wherein the ionic strength of the biocide release agent is at least about $2\times10^{-2}$ mol/l.

Example 24

| | |
|---|---|
| Cationic Biocide | 0.1-0.64% |
| Solvent | 1.3-8% |
| Surfactant | 0.05-1.6% |
| Builder detergent | 0.0067-0.64% |
| Polymer | 0.01-2.083% |
| Biocide release agent | 0.067-2% |
| Water | at least 53% |
| Dry cleaning wipe | 20-33% |
| Loading ratio | 2-4:1 | wherein the ionic strength of the biocide release agent is at least about $2\times10^{-2}$-1 mol/l.

Example 25

| | |
|---|---|
| Vantocil P | 0.117-0.4% |
| Isopropanol | 1.36-4% |
| PnB (glycol ether) | 0.389-1.5% |
| APG 325 | 0.194-1% |
| Ammonium Chloride | 0.0389-1% |
| Dipotassium EDTA | 0-0.3% |
| Gafquat 440 | 0-2.083% |
| Fragrance Oil | 0-1% |
| Water | at least 70.6% |
| DuPont 8838 (wipe) | 20-22.2% |
| Loading ratio | 3.5-4:1 | wherein the ionic strength of the salts in the improved cleaning composition is about $3.5\times10^{-2}$-$5\times10^{-2}$ mol/l.

Example 26

| | |
|---|---|
| Vantocil P | 0.23-0.32% |
| Isopropanol | 2.7-4% |
| Barlox 12 | 0.155-0.32% |
| Potassium Citrate | 0.7-0.88% |
| Disodium EDTA | 0.07-0.12% |
| Gafquat 440 | 0.02-1.042% |
| Fragrance | 0-1% |
| Water | at least 70% |
| DuPont 8838 | 20-22.2% |
| Loading ratio | 3.5-4:1 | wherein the ionic strength of the salts in the improved cleaning composition is about $3.5\times10^{-2}$-$5\times10^{-2}$ mol/l.

Example 27

| | |
|---|---|
| Vantocil P | 0.25-0.45% |
| Isopropanol | 2.7-5% |
| Barlox 12 | 0.15-0.35% |
| Potassium Citrate | 0.05-0.9% |
| Disodium EDTA | 0.05-0.15% |
| Gafquat 440 | 0.02-1.042% |
| Fragrance | 0.01-0.5% |
| Water | at least 70% |
| DuPont 8838 | 20-22.2% |
| Loading ratio | 3.5-4:1 |
| pH | Alkaline | wherein the ionic strength of the salts in the improved cleaning composition is about $3.5\times10^{-2}$-$5\times10^{-2}$ mol/l.

Example 28

| | |
|---|---|
| Vantocil P | 0.15-0.4% |
| Isopropanol | 2.5-4% |
| PnB (glycol ether) | 0.05-2% |
| Surfonic L108 | 0.2-0.5% |
| Zonyl FSO | 0-1% |
| Ammonium Chloride | 0.05-0.8% |
| Dipotassium EDTA | 0.07-0.12% |
| Gafquat 440 | 0.02-1.042% |
| Fragrance | 0-2% |
| Water | at least 70% |
| DuPont 8838 | 20-22.2% |
| Loading ratio | 3.5-4:1 |
| pH | Alkaline | wherein the ionic strength of the salts in the improved cleaning composition is about $3.5\times10^{-2}$-$5\times10^{-2}$ mol/l.

Example 29

| | |
|---|---|
| Vantocil P | 0.1-0.5% |
| Isopropanol | 1.3-4% |
| PnB (glycol ether) | 0.35-1.5% |
| Surfactant | 0.15-1% |
| Ammonium Chloride | 0.03-1% |
| Dipotassium EDTA | 0-0.3% |
| Gafquat 440 | 0-1.042% |
| Fragrance | 0-1% |
| Water | at least 70.6% |
| DuPont 8838 (wipe) | 15-30% |
| Loading ratio | 3-5:1 |
| pH | Alkaline | wherein the ionic strength of the salts in the improved cleaning composition is about $3.5 \times 10^{-2}$-$5 \times 10^{-2}$ mol/l.

Example 30

| | |
|---|---|
| Barquat 4250 Z/Vantocil P | 0.23-0.32% |
| Isopropanol | 2.7-4% |
| Barlox 12 | 0.155-0.32% |
| Disodium EDTA | 0.07-0.12% |
| Gafquat 440 | 0-1.042% |
| Potassium Citrate | 0.1-0.88% |
| Water | at least 70% |
| DuPont 8838 | 20-22.2% |
| Loading ratio | 3.5-4:1 |
| pH | Alkaline | wherein the ionic strength of the salts in the improved cleaning composition is about $3.5 \times 10^{-2}$-$5 \times 10^{-2}$ mol/l.

Example 31

| | |
|---|---|
| Vantocil P | 0.038-0.48% |
| Isopropanol | 0.77-2.4% |
| Dowanol PnP | 0.38-1.6% |
| Lauryl Dimethyl Amine Oxide | 0-0.8% |
| PnB (glycol ether) | 0-1.6% |
| APG 325 | 0.038-0.8% |
| DiPotassium EDTA | 0-0.4% |
| Gafquat 440 | 0.038-0.4% |
| Ammonium Chloride | 0-0.32% |
| Fragrance | 0-0.4% |
| Water | at least 70% |
| DuPont 8838 | 20-22.2% |
| Loading ratio | 3.5-4:1 |
| pH | Alkaline | wherein the ionic strength of the salts in the improved cleaning composition is about $3.5 \times 10^{-2}$-$5 \times 10^{-2}$ mol/l.

Example 32

| | |
|---|---|
| Vantocil P | 0.038-0.4% |
| Isopropanol | 0.77-2.4% |
| Dowanol PnP | 0.577-1.2% |
| Lauryl Dimethyl Amine Oxide | 0-0.8% |
| PnB (glycol ether) | 0-0.8% |
| APG 325 | 0.077-0.4% |
| DiPotassium EDTA | 0-0.4% |
| Gafquat 440 | 0.038-0.32% |
| Ammonium Chloride | 0-0.32% |
| Fragrance | 0-0.4% |
| Water | at least 70% |
| DuPont 8838 | 20-22.2% |
| Loading ratio | 3.5-4:1 |
| pH | Alkaline | wherein the ionic strength of the salts in the improved cleaning composition is about $3.5 \times 10^{-2}$-$5 \times 10^{-2}$ mol/l.

When a biocide release agent is used in and/or is used in combination with the improved cleaning composition, the biocide release agent positively affects the release of cationic biocide from an absorbent and/or adsorbent material. As illustrated in Table 1, and in FIG. 1, the increase in salt content (e.g., biocide release agent) in the improved cleaning composition results in a decreased quat retention on the absorbent and/or adsorbent material (e.g. cleaning wipe) and an increase in quat recovery. Similar results were obtained when biguanide compounds were included in the improved cleaning composition as illustrated in Table 2 and in FIG. 2.

In obtaining the results set forth in Table 2, the improved cleaning composition that included quat and was loaded on a cleaning wipe, and several trials were conducted using two types of cleaning wipes and five different types of biocide release agent. The quat used in the improved cleaning composition was BARQUAT 4250Z by Lonza. The improved cleaning composition included about 0.29 weight percent biocide, about 0.3 weight percent amine oxide, about 0.1 weight percent sodium EDTA, 4.9 weight percent isopropanol, and the balance water. Each cleaning wipe had a loading ratio of improved cleaning composition to cleaning wipe of about 3.75:1.

TABLE 1

Quat Bactericidal Wipe Effective of Salts on Quat Released
(Quat level = 0.29%)

| % Salt | % Quat Recovery with K-Citrate (DuPont 8838) | % Quat Recovery with KCl (DuPont 8838) | % Quat Recovery with Na-Citrate (DuPont 8838) | % Quat Recovery with MgSO$_4$ (DuPont 8838) | % Quat Recovery with NH$_4$Cl (Dexter ZA) |
|---|---|---|---|---|---|
| 0 | 52 | 51 | | | |
| 0.00304 | | | | | 67.4 |
| 0.00595 | | | | | 73.1 |
| 0.1013 | 57 | 60 | 59 | 71 | 75.9 |
| 0.304 | 75 | 69 | 73 | 79 | 82.1 |
| 0.697 | 88 | 77 | 90 | 91 | 82.4 |
| 1.0 | 98 | 86 | 89 | 96 | 96.3 |

The improved cleaning composition that included biguanide compounds and was also loaded on a cleaning wipe, and a single trial was conducted using Dexter 8589 for the cleaning wipe and Vantocil P(PHMB) by Avecia for the biguanide compound. The improved cleaning composition included about 0.3 weight percent biguanide compound, about 0.5 weight percent APG, 2.6 weight percent isopropanol, about 1 weight percent Dowanol PnB, and the balance water. The cleaning wipe had a loading ratio of improved cleaning composition to cleaning wipe of about 3.75:1. The results of the test are illustrated in Table 2.

TABLE 2

Biguanide Bactericidal Wipe Effective of Salts on Biguanide Compound Released (Biguanide Compound level = 0.3%)

| % Salt | % Biguanide Compound Release with $NH_4Cl$ (Dexter 8589) |
|---|---|
| 0 | 35.9 |
| 0.1 | 42.7 |
| 0.3 | 46 |
| 0.4 | 59.1 |
| 0.5 | 62 |
| 0.6 | 68 |
| 0.7 | 77 |
| 0.8 | 88 |
| 0.9 | 92 |

Figure 2:
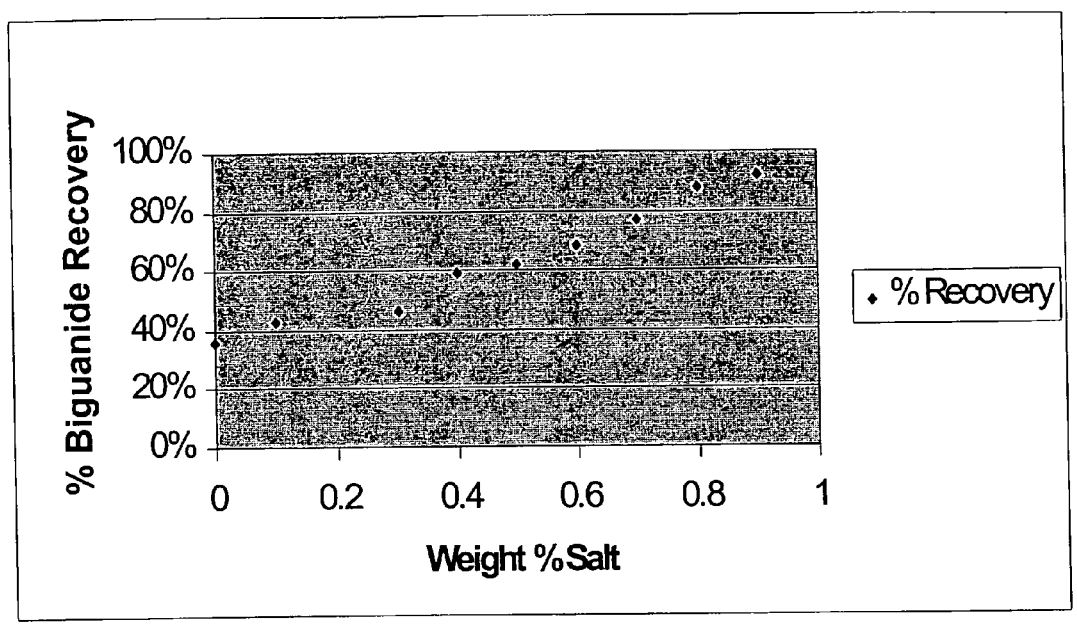
FIG. 2 is a graphical illustration of the percentage of biguanide compound recovered from the cleaning wipe as a function of the weight percentage of salt in the improved cleaning composition.

As illustrated in Tables 1 and 2, the quat and biguanide compound retention on the cleaning wipe is about 50% and 64% respectively when the biocide release agent was not included in the improved cleaning composition. The results in Tables 1 and 2 illustrate that the quat and biguanide compound retention is substantially reduced by increasing the concentration of biocide release agent in the improved cleaning composition. The variances in measured quat and biguanide compound retention are believed to be due to the type of cleaning wipe used, the ionic strength of the biocide release agent, and/or the chemical structure of the quat or biguanide compound. In every test, the inclusion of the biocide release agent in the improved cleaning composition resulted in an increased quat and biguanide compound release from the cleaning wipe. FIG. 1 graphically illustrates the quat retention on a DuPont 8838 cleaning wipe as a function of the biocide release agent content of the improved cleaning composition. FIG. 2 graphically illustrates the biguanide compound retention on a Dexter 8589 cleaning wipe as a function of the biocide release agent content of the improved cleaning composition.

Another set of tests were conducted to determine if there was any effect on the quat release levels from the cleaning wipe as a function of the type of cleaning wipe. The results of these tests are illustrated in Table 3. The cationic biocide used in the improved cleaning composition illustrated in Table 3 was BARQUAT 4250Z by Lonza. The improved cleaning composition included about 0.29 weight percent cationic biocide, about 0.3 weight percent amine oxide, about 0.1 weight percent sodium EDTA, about 4.9 weight percent isopropanol, and the balance water. The biocide release agent used was potassium citrate. Two concentrations of potassium citrate were used in the improved cleaning composition. The cleaning wipe was DuPont 8838 having a loading ratio of improved cleaning composition to cleaning wipe of about 3.75:1.

TABLE 3

Effect of Different Cleaning Wipes on Quat Released using K Citrate

| Cleaning Wipe | % Quat Released |
|---|---|
| Dexter 10180 (0.24% K Citrate) | 78 |
| Dexter M10201 (0.24% K Citrate) | 93 |
| Dexter ZA (0.24% K Citrate) | 83 |
| Dexter 10180 (0.79% K Citrate) | 100 |
| Dexter M10201 (0.79% K Citrate) | 100 |
| Dexter ZA (0.79% K Citrate) | 100 |

The test results in Table 3 reveal that an increase in quat release from the cleaning wipe occurred regardless of the type of wood pulp containing cleaning wipe. Similar results were observed from cleaning compositions containing biguanide compounds. In addition, the test results confirmed that increased biocide release agent concentrations in the improved cleaning composition resulted in decreased quat and biguanide compound retention on the wipe.

Another set of tests were conducted to determine if there was any affect on the amount of quat or biguanide compound release as a function of the amount of quat or biguanide compound in the improved cleaning composition. The results of these tests are illustrated in Table 4. The cationic biocide used in the improved cleaning composition illustrated in Table 4 was BARQUAT 4250Z by Lonza. The improved cleaning composition included about 0.3 weight percent amine oxide, about 1 weight percent potassium citrate, about 0.1 weight percent sodium EDTA, about 4.9 weight percent isopropanol, and the balance water. The cleaning wipe was DuPont 8838 having a loading ratio of improved cleaning composition to cleaning wipe of about 3.75:1.

TABLE 4

Effect of different quat levels on quat released (K citrate = 1.0%)

| % Quat in Improved cleaning composition | % K-citrate = 1.0% |
|---|---|
| 0 | N/A |
| 0.507 | 100% |
| 0.101 | 99.6% |
| 0.203 | 95.8% |
| 0.279 | 94.2% |
| 0.367 | 95.2% |

The results in Table 4 indicate that the amount of quat compound released from the cleaning wipe is not adversely affected by the amount of quat in the improved cleaning composition. Similar results were observed from cleaning compositions containing biguanide compounds.

Several tests were also conducted to determine whether the biocide release agent in the cleaning agent adversely affected the bactericidal efficacy of the improved cleaning composition containing quat and/or biguanide compound. In each test conducted, the biocide release agent did not adversely affect the bactericidal efficacy of the improved cleaning composition. In addition, it was found that the biocide release agent alone had little or no bactericidal efficacy.

Micro efficacy data was also obtained for an improved cleaning composition containing a quat and an improved cleaning composition containing a biguanide compound. These two formulations were compared to Lysol cleaner and Mr. Clean, both commercially available products. The results are set forth in Table 5.

TABLE 5

MICRO EFFICACY DATA

|  | 30 Seconds Sanitizer Log Reduction | | 4 Minutes Disinfection Log Reduction | | | |
|---|---|---|---|---|---|---|
|  | Staph | Kleb | Staph | Pseudomonas | Salmonella | Influenza A2 |
| Clorox B | 99.9% | 99.9% | 99.999% | 99.999% | 99.999% | 99.999% |
| Clorox Q | 99.9% | 99.9% | 99.999% | 99.999% | 99.999% | 99.999% |
| Mr. Clean* | — | — | — | — | 99.999% | — |
| Lysol* | 99.9% | 99.9% | 99.999% | 99.999% | 99.999% | 99.999% |

*The time period for Mr. Clean and Lysol was tested at 10 minutes.

The Clorox B formula is an improved cleaning composition that includes about 0.3 weight percent Vantocil P. The Clorox Q formula is an improved cleaning composition that includes about 0.4 weight percent BARQUAT 4250Z. The general formulations of Clorox B' and Clorox Q' and the specific formulations of Clorox B and Clorox Q are set forth below:

| Clorox B' | | Clorox Q' | |
|---|---|---|---|
| Vantocil P | 0.25-0.35% | Bardac 4250 | 0.3-0.5% |
| APG | 0.4-0.6% | Barlox 12 | 0.2-0.4% |
| Isopropanol | 2-3% | Isopropanol | 4.2-5.5% |
| PnB | 0.8-1.2% | DiNa EDTA | 0.05-0.2% |
| Ammonium Chloride | 0.1-0.5% | Potassium Citrate | 0.08-0.5% |
| Fragrance | 0.1-0.2% | Fragrance | 0.1-0.2% |
| Water | Balance | Water | Balance |
| DuPont 8838 | 20-22.2% | DuPont 8838 | 20-22.2% |
| Loading ratio | 3.5-4:1 | Loading ratio | 3.5-4:1 |

| Clorox B | | Clorox Q | |
|---|---|---|---|
| Vantocil P | 0.3% | Bardac 4250 | 0.37% |
| APG | 0.5% | Barlox 12 | 0.29% |
| Isopropanol | 2.6% | Isopropanol | 4.8% |
| PnB | 1% | DiNa EDTA | 0.1% |
| Ammonium Chloride | 0.1% | Potassium Citrate | 0.1% |
| Fragrance | 0.15% | Fragrance | 0.15% |
| Water | Balance | Water | Balance |
| DuPont 8838 | 21.05% | DuPont 8838 | 21.05% |
| Loading ratio | 3.75:1 | Loading ratio | 3.75:1 |

As illustrated in Table 5, both Clorox formulas exhibit excellent micro efficacy properties. The micro efficacy properties where as good as or better than the tested commercially available products.

Tests were also conducted to determine the cleaning effectiveness of the improved cleaning composition. Two different sets of data were collected for determining the cleaning effectiveness of the improved cleaning composition, namely filming and streaking data, and soil removal data. Two different Clorox formulations were used when testing the soil removal effectiveness of the formulations, and three Clorox formulations were used when testing the filming and streaking properties of the formulations. These formulations were also successfully used on a variety of absorbent and/or adsorbent materials (e.g. wipes, mop heads, sponges, towels, etc.). Clorox Q and Q1 are quat containing formulations. Clorox B is a biguanide compound containing formulation. In each test, the Clorox formulations were compared to Mr. Clean and Lysol cleaners. The test results of these data sets are shown in Tables 6 and 7.

TABLE 6

SOIL REMOVAL DATA

| Formula | Sanders & Lambert | Bathroom Soil | Kitchen Grease |
|---|---|---|---|
| Clorox Q | 2306.7 | 56 | 551.6 |
| Clorox B | 2391.3 | 120 | 692.5 |
| Mr. Clean | 2615 | 314.5 | 607.2 |
| Lysol | 1845.4 | 27.9 | 527.4 |

Sanders & Lambert (Industry based soil)
Bathroom Soil (Industry based soil ASTM D5343-93)
Kitchen Grease (Industry CSMA Based soil DCC-12)

TABLE 7

FILMING AND STREAKING DATA

| Formula | F&S Score |
|---|---|
| Clorox Q | 5.09 |
| Lysol | 5.14 |
| Clorox B | 2.8 |
| Mr. Clean | 7.17 |
| Clorox Q1 | 5.16 |

* Lower is better, less perceivable residue.

As illustrated in Table 6, both Clorox formulations effectively removed a variety of different soils from a hard surface. The number values in Table 6 represent the area under a curve. The larger the area under the curve, the cleaner the surface that was cleaned. In other words, the higher the number, the better the cleaning. Both Clorox formulations out performed the Lysol cleaner in each soil test. Both Clorox formulations also cleaned the Sanders & Lambert soil and kitchen grease soil as well as or better than Mr. Clean. Mr. Clean had better cleaning results for the bathroom soil. In each test, Clorox B slightly outperformed Clorox Q except in the bathroom soil test where Clorox B was significantly better than Clorox Q. Although Mr. Clean performed slightly better than the Clorox formulations in certain soil tests, Mr. Clean did not effectively sanitize or sterilize the cleaned surface as illustrated in Table 5. Therefore, the results in Table 6 illustrate that the Clorox formulations are a significant improvement over prior cleaning compositions in that the Clorox formulations effective clean a variety of soils and also sanitize or sterilize such cleaned surface. Neither Mr. Clean or Lysol exhibit such properties.

The Clorox formulations also exhibited excellent filming and streaking characteristics. Clorox B had the best filming and streaking characteristics. Clorox Q and Q1 had filming and streaking characteristics that were similar to Lysol. Mr. Clean exhibited by far the most filming and streaking of the cleaners tested. The significantly reduced filming and streaking of Clorox B is believed to be the result of the special combination of biguanide compound and surfactant, or biguanide compound, surfactant and solvent in the improved cleaning composition. The specific biguanide compound used in Clorox B was Vantocil P; however, it is believed that other biguanide compounds will produce similar results. The surfactant used in Clorox B was a polyglucoside, specifically an aklypolyglucoside. The solvent included a lower alcohol and PnB. The combination of a quat with a polyglucoside, lower alcohol and PnB was also tested in Clorox Q1, but did not yield a F&S score that was nearly as low as the biguanide compound formulation of Clorox B. The general formulation for Clorox Q1 is set forth as follows:

| Clorox Q1 | |
| --- | --- |
| BarQuat 205M | 0.15-0.3% |
| APG | 0.4-0.6% |
| Isopropanol | 2-3% |
| PnB | 0.8-1.2% |
| Ammonium Chloride | 0.1-0.5% |
| Fragrance | 0.1-0.2% |
| Water | Balance |
| DuPont 8838 | 20-22.2% |
| Loading ratio | 3.5-4:1 |

Another set of tests were conducted to ascertain the dermal irritancy of the improved cleaning compositions. Three Clorox formations were used. These formulations were also successfully used on a variety of absorbent and/or adsorbent materials (e.g. wipes, mop heads, sponges, towels, etc.). Clorox Q and Q2 include about 0.2 weight percent quat and Clorox B included about 0.3 weight percent biguanide compound. The general formulation for Clorox Q2' and the specific formulation of Clorox Q2 are set forth as follows:

| Clorox Q2' | | Clorox Q2 | |
| --- | --- | --- | --- |
| BarQuat 205M | 0.15-0.3% | BarQuat 205M | 0.2% |
| Surfonic L108 | 0.3-0.5% | Surfonic L108 | 0.35% |
| Zonyl FSO | 0.01-0.5% | Zonyl FSO | 0.04% |
| Isopropanol | 2-3.5% | Isopropanol | 2.6% |
| PnB | 0.8-1.4% | PnB | 1% |
| DiK EDTA | 0.06-1.5% | DiK EDTA | 0.1% |
| Ammonium Chloride | 0.08-0.5% | Ammonium Chloride | 0.1% |
| Fragrance | 0.1-0.2% | Fragrance | 0.15% |
| Water | Balance | Water | Balance |
| DuPont 8838 | 20-22.2% | DuPont 8838 | 21.05% |
| Loading ratio | 3.5-4:1 | Loading ratio | 3.75:1 |

Figure 3:
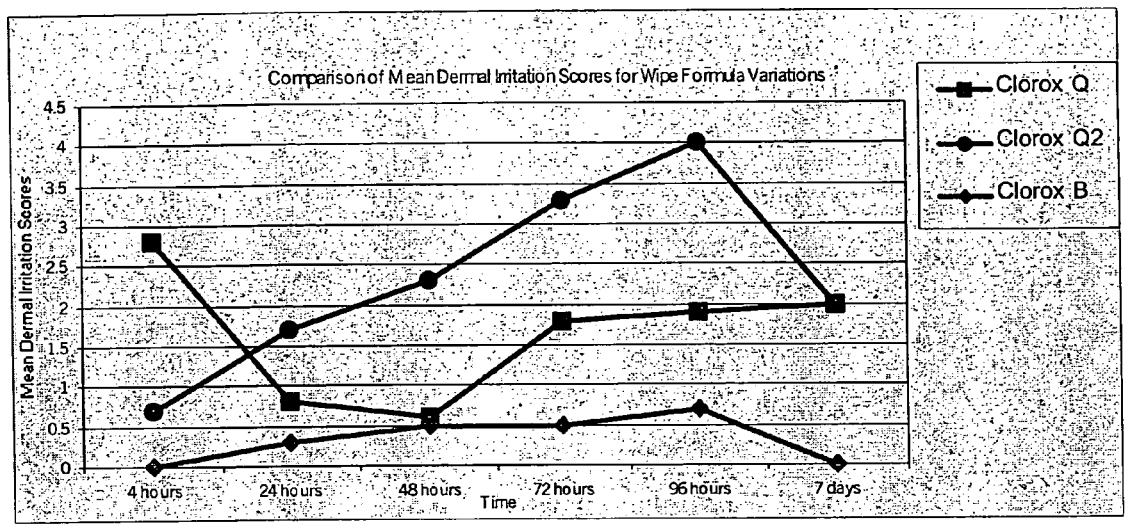
FIG. 3 is a graphical illustration of dermal irritation scores of several improved cleaning compositions of the present invention.

The results of these tests are tabulated in Table 8 and illustrated in FIG. 3.

TABLE 8

MEAN DERMAL IRRITATION

| Formula | 4 hours | 24 hours | 48 hours | 72 hours | 96 hours | 7 days |
| --- | --- | --- | --- | --- | --- | --- |
| Clorox Q | 2.8 | 0.8 | 0.6 | 1.8 | 1.9 | 2.0 |
| Clorox Q2 | 0.7 | 1.7 | 2.3 | 3.3 | 4.0 | 2.0 |
| Clorox B | 0 | 0.3 | 0.5 | 0.5 | 0.7 | 0 |

The test results reveal that Clorox B, which included a higher concentration of biguanide compound than the concentration of quat in Clorox Q and Q2, exhibited lower mean dermal irritation scores that the two quat containing formulations. These unanticipated results reveal that the biguanide compound containing formulations induce significantly less dermal irritation without compromising the cleaning and sanitizing or sterilizing properties of the improved cleaning composition. As a result, the biguanide compound containing formulations can be used in a wider range of applications, especially where skin irritation is of concern.

Several formulations for the improved cleaning composition were tested to determine the benefit of adding a polymer to the improved cleaning composition. These formulations were successfully used on a variety of absorbent and/or adsorbent materials (e.g. wipes, mop heads, sponges, towels, etc.). The polymer used in this series of tests was Gafquat 440. The tests revealed that the improved cleaning composition that included a polymer resulted in improved detergency. The formulations of the improved cleaning composition and the Sanders & Lambert scores are set forth in Table 9.

TABLE 9

GAFQUAT ADDITION

| Clorox Composition | A | B | C | D | E | F |
| --- | --- | --- | --- | --- | --- | --- |
| Glucopon 325 | 0.15 | 0.15 | 0.15 | 0.15 | 0.15 | 0.15 |
| Isopropanol | 2.00 | 2.00 | 2.00 | 2.00 | 2.00 | 2.00 |
| Dowanol PnP | 1.00 | 1.00 | 1.00 | 1.00 | 1.00 | 1.00 |
| Gafquat 440 | 0.20 | 0.20 | 0.20 | 0.20 | 0.20 | 0 |
| Zonyl FSO | 0.04 | 0.04 | 0.04 | 0.04 | 0.04 | 0.04 |
| Barquat 205M | 0 | 0.02 | 0.02 | 0.035 | 0.035 | 0.035 |
| Vantocil P | 0.10 | 0.05 | 0.10 | 0.10 | 0.05 | 0.05 |
| Fragrance | 0.03 | 0.03 | 0.03 | 0.03 | 0.03 | 0.03 |
| Balance water | | | | | | |
| Score | 2160 | 2165 | 2166 | 2155 | 2152 | 1790 |

Glucopon 325 (Cognis) - alkylpolyglucoside
Dowanol PnP (Dow Chemical) - propyleneglycol - propylether
Gafquat 440 (ISP Corp.) - copolymer of vinylpyrrolidone and dimethylaminoethyl methacrylate quaternized with diethylsulfate.
Zonyl FSO (DuPont) - fluorochemical
Barquat 205M (Lonza) - alkyldimethylbenzylammonium chloride
Vantocil P (Avecia) - poly(hexamethylene biguanide) hydrochloride
*Higher scores mean better cleaning The results of the Sanders & Lambert test reveal that the addition of Gafquat 440 to the improved cleaning composition significantly improved the cleaning performance of the improved cleaning composition. Further testing revealed a noticeable detergency performance increase in the improved cleaning composition when the improved cleaning composition included at least about 0.02 weight percent Gafquat. Gafquat contents as high as 10 weight percent also produced improved the cleaning performance of the improved cleaning composition. Concentrations that exceeded about 10 weight percent resulted in increased filming and streaking of the improved cleaning composition. Testing also revealed that the combination of Gafquat and APG resulted in improved detergency. APG, a surfactant, provided detergency to the improved cleaning composition without the inclusion of the Gafquat. However, the detergency of the improved cleaning composition was significantly enhanced when Gafquat was added in combination with APG to the improved cleaning composition. Similar improvements in detergency were also realized by the inclusion of other polymers in the improved cleaning composition. Several of these polymers are identified in Tables 10 and 11. Generally, the weight percent of APG in the improved cleaning composition is about 0.02-5%.

Additional tests were conducted to compare the use of various types of polymers in combination with detergency surfactants such as APG. These formulations were also successfully used on a variety of absorbent and/or adsorbent materials (e.g. wipes, mop heads, sponges, towels, etc.). The test results are set forth in Table 10.

The results from Table 10 reveal that polymers other than Gafquat effectively work in combination with detergency surfactants to significantly improved the detergency of the improved cleaning composition. The results in Table 10 also reveal that the addition of a fluorosurfactant such as Zonyl FSO can also improve the detergency of the improved cleaning composition. As shown in Formulation L, the improved cleaning composition is absent polymer and fluorosurfactant. The Sanders & Lambert score for Formulation L was the lowest of the test formulations. An increase in the Sanders & Lambert score was obtained by adding a polymer to the improved cleaning composition as shown in Formulation M. The inclusion of fluorosurfactant in several of the formulations resulted in a significant increase in the Sanders & Lambert score.

Table 11 illustrates several formulations for the improved cleaning composition that were used in combination with a cleaning wipe and other types of absorbent and/or adsorbent materials, and which provided effective contact disinfection on hard surfaces such as tiles. These formulations also

TABLE 10

VARIOUS POLYMER ADDITIONS

| Clorox Composition | G | H | I | J | K | L | M |
|---|---|---|---|---|---|---|---|
| Glucopon 325 | 0.15 | 0.15 | 0.15 | 0.15 | 0.15 | 0.15 | 0.15 |
| Isopropanol | 2.00 | 2.00 | 2.00 | 2.00 | 2.00 | 2.00 | 2.00 |
| Dowanol PnP | 1.00 | 1.00 | 1.00 | 1.00 | 1.00 | 1.00 | 1.00 |
| Zonyl FSO | 0.04 | 0.04 | 0.04 | 0.04 | 0.04 | | |
| Barquat 205M | 0.04 | 0.04 | 0.04 | 0.04 | 0.04 | | |
| Vantocil P | 0.05 | 0.05 | 0.05 | 0.05 | 0.05 | 0.02 | 0.10 |
| Fragrance | 0.03 | 0.03 | 0.03 | 0.03 | 0.03 | 0.03 | 0.03 |
| Gafquat 440 | 0.10 | 0.05 | | | | | 0.06 |
| Gafquat 755 | | | 0.20 | | | | |
| Mirapol 550 | | | | 0.20 | | | |
| Mirapol A-15 | | | | | | 0.20 | |
| Balance water | | | | | | | |
| Score | 2075 | 1926 | 2166 | 1938 | 2037 | 1842 | 1979 |

Glucopon 325 (Cognis) - alkylpolyglucoside
Dowanol PnP (Dow Chemical) - propyleneglycol - propylether
Zonyl FSO (DuPont) - fluorochemical
Barquat 205M (Lonza) - alkyldimethylbenzylammonium chloride
Vantocil P (Avecia) - poly(hexamethylene biguanide) hydrochloride
Gafquat 440 (ISP Corp.) - copolymer of vinylpyrrolidone and dimethylaminoethyl methacrylate quaternized with diethylsulfate.
Gafquat 755 (ISP Corp.)
Mirapol 550 (Rhone-Poulenc)
Mirapol A-15 (Rhone-Poluenc)

resulted in effective detergency of the improved cleaning composition.

TABLE 11

MORE POLYMER ADDITIONS

| Clorox Composition | N | O | P | Q | R | S | T | U | V |
|---|---|---|---|---|---|---|---|---|---|
| Glucopon 325 | 0.50 | 0.50 | 0.50 | 0.50 | 0.50 | 0.50 | 0.50 | 0.50 | 0.50 |
| Isopropanol | 2.60 | 2.60 | 2.60 | 2.60 | 2.60 | 2.60 | 2.60 | 2.60 | 2.60 |
| Dowanol PnP | 1.00 | 1.00 | 1.00 | 1.00 | 1.00 | 1.00 | 1.00 | 1.00 | 1.00 |

TABLE 11-continued

MORE POLYMER ADDITIONS

| Clorox Composition | N | O | P | Q | R | S | T | U | V |
|---|---|---|---|---|---|---|---|---|---|
| Vantocil P | 0.30 | 0.30 | 0.30 | 0.30 | 0.30 | 0.30 | 0.30 | 0.30 | 0.30 |
| Ammonium chloride | 0.10 | 0.10 | 0.10 | 0.10 | 0.10 | 0.10 | 0.10 | 0.10 | 0.10 |
| Defoamer | 0.05 | 0.05 | 0.05 | 0.05 | 0.05 | 0.05 | 0.05 | 0.05 | 0.05 |
| Fragrance | 0.15 | 0.15 | 0.15 | 0.15 | 0.15 | 0.15 | 0.15 | 0.15 | 0.15 |
| Airvol 24-203 | 1.00 | | | | | | | | |
| Aquamere H-1212 | | 1.00 | | | | | | | |
| Cyanamer —100L | | | 1.00 | | | | | | |
| Diaformer Z-712 | | | | 1.00 | | | 0.50 | 1.00 | 1.50 |
| PVP-K90 | | | | | 1.00 | | | | |
| Syntran HX52-1-1 | | | | | | 1.00 | | | |
| Balance water | | | | | | | | | |

Glucopon 325 (Cognis) - alkylpolyglucoside
Dowanol PnP (Dow Chemical) - propyleneglycol - propylether
Vantocil P (Avecia) - poly(hexamethylene biguanide) hydrochloride
Airvol 24-203 (Air Products) - polyvinylalcohol
Aquamere H-1212 (Hydromer) - PVP/Polyurethane
Cyanamer N-100L (Cytec Industries) - polyacrylamide
Diaformer Z-712 (Clariant) - methacryloylethyl-oxide/methacrylates copolymer
PVP-K90 (VWR Scientific) - polyvinylpyrrolidone
Syntran HX52-1-1 (Interpolymer) - quaternary acrylic copolymer The test results from Table 11 reveal that various types of polymers can be effectively used in the improved cleaning composition without adversely affecting the biocidal efficacy of the improved cleaning composition. The formulations in Table 11 also resulted in an improved cleaning composition that had improved detergency and/or reduced filming and streaking.

The improved cleaning composition can include a variety of surfactants and/or builders. Several formulations which incorporate the use of a few of these surfactants and/or builders are set forth in Table 12.

TABLE 12

VARIOUS SURFACTANTS/BUILDERS

| Clorox Composition | W | X | Y | Z | A1 |
|---|---|---|---|---|---|
| Glucopon 325 | 0.02 | | | | |
| Neodol 91-8 | | 0.02 | | | |
| Barlox 12 | | | 0.02 | | |
| Dowanol PM | 2.00 | 2.00 | 2.00 | 2.00 | 2.00 |
| Dowanol DB | 5.00 | 5.00 | 5.00 | 5.00 | 5.00 |
| Gafquat 440 | 0.02 | 0.02 | 0.02 | | |
| Chlorhexidine | 0.02 | 0.02 | 0.02 | | |
| Vantocil P | | | | 0.02 | 0.02 |
| DMAMP 80 | | | | 0.05 | |
| Diammonium EDTA | | | | | 1.00 |
| Balance water | | | | | |

Glucopon 325 (Cognis) - alkylpolyglucoside
Neodol 91-8 (Shell Chemical) - alkylethoxylate
Barlox 12 (Lonza) - amineoxide
Dowanol PM (Dow Chemical) - propyleneglycol methylether
Dowanol DB (Dow Chemical) - diethyleneglycol butylether
Gafquat 440 (ISP Corp.) - copolymer of vinylpyrrolidone and dimethylaminoethyl methacrylate quaternized with diethylsulfate.
Chlorhexidine (Aldrich Chemical)
Vantocil P (Avecia) - poly(hexamethylene biguanide) hydrochloride
DMAMP-80 (Angus Company) - 2-dimethylamino-2-methyl-1-propanol
Diammonium EDTA (Aldrich Chemical)

The formulations of the improved cleaning composition set forth in Table 12 produced compositions stable compositions which had effective detergency and reduced filming and streaking. These formulations were successfully used on a variety of absorbent and/or adsorbent materials (e.g. wipes, mop heads, sponges, towels, etc.).

Several formulations of the improved cleaning composition were tested to illustrate the improved cleaning performance when using a dual boiling point solvent system in the improved cleaning composition. These formulations were successfully used on a variety of absorbent and/or adsorbent materials (e.g. wipes, mop heads, sponges, towels, etc.). The results of these tests are set forth in Tables 13 and 14.

TABLE 13

DUAL SOLVENT CLEANING PERFORMANCE

| Clorox Composition | B1 | C1 | D1 | E1 | F1 | G1 |
|---|---|---|---|---|---|---|
| Glucopon 325 | 1.50 | 1.50 | 1.50 | 1.50 | 1.50 | 1.50 |
| Isopropanol | 1.00 | 0.50 | | | | |
| Ethanol | | | | | | 0.50 |
| Dowanol PM | | | | 0.50 | | |
| Dowanol PnP | | 0.50 | | | | |
| Dowanol DPnB | | | | | 0.50 | 0.50 |
| Dowanol DB | | | 0.50 | 0.50 | | |
| Gafquat 440 | 0.20 | 0.20 | 0.20 | 0.20 | 0.20 | 0.20 |
| Vantocil P | 0.10 | 0.10 | 0.10 | 0.10 | 0.10 | 0.10 |
| Balance water | | | | | | |
| Relative Performance on Sanders & Lambert | 1 | 1 | 4 | 2 | 4 | 3 |

Glucopon 325 (Cognis) - alkylpolyglucoside
Dowanol PM (Dow Chemical) - propyleneglycol methylether
Dowanol PnP (Dow Chemical) - propyleneglycol n-propylether
Dowanol DPnB (Dow Chemical) - dipropyleneglycol n-butylether
Dowanol DB (Dow Chemical) - diethyleneglycol butylether
Gafquat 440 (ISP Corp.) - copolymer of vinylpyrrolidone and dimethylaminoethyl methacrylate quaternized with diethylsulfate.
Vantocil P (Avecia) - poly(hexamethylene biguanide) hydrochloride
*Performance - 1 indicates best performance and 4 indicates worst performance.

The formulations of the improved cleaning composition set forth Table 13 illustrate the improved cleaning performance of the improved cleaning composition when a dual boiling point solvent system is included in the improved cleaning composition. The formulations set forth in Table 14 illustrate the reduced filming and streaking of the improved cleaning composition when a dual boiling point solvent system is included in the improved cleaning composition.

TABLE 14

DUAL SOLVENT FILMING/STREAKING PERFORMANCE

| Composition | H1 | I1 | J1 | K1 | L1 | Lemon Scent Lysol Disinfectant All Purpose Cleaner | Citrus Scent Lysol Disinfectant Antibacterial Kitchen Cleaner |
|---|---|---|---|---|---|---|---|
| Glucopon 325 | 1.50 | 1.50 | 1.50 | 1.50 | 1.50 | | |
| Isopropanol | 0.50 | 0.50 | | 1.00 | | | |
| Dowanol PM | | | 0.50 | | | | |
| Dowanol PnP | 0.50 | 0.50 | | | | | |
| Dowanol DB | | | 0.50 | | 0.50 | | |
| Gafquat 440 | 0.20 | 0 | 0.20 | 0.20 | 0.20 | | |
| Vantocil P | 0.10 | 0.10 | 0.10 | 0.10 | 0.10 | | |
| Balance water | | | | | | | |
| Filming/Streaking | 5 | 5 | 5 | 10 | 10 | 10 | 7 |

Glucopon 325 (Cognis) - alkylpolyglucoside
Dowanol PM (Dow Chemical) - propyleneglycol methylether
Dowanol PnP (Dow Chemical) - propyleneglycol n-propylether
Dowanol DB (Dow Chemical) - diethyleneglycol butylether
Gafquat 440 (ISP Corp.) - copolymer of vinylpyrrolidone and dimethylaminoethyl methacrylate quaternized with diethylsulfate.
Vantocil P (Avecia) - poly(hexamethylene biguanide) hydrochloride
*Filming/streaking scores of 10 indicate worse filming/streaking than lower scores.

The formulations of the improved cleaning composition illustrated in Table 14 were compared to two different Lysol products. All of the tested formulations were applied to black tile, and tested for filming/streaking using an absorbent pad. These formulations were successfully used on a variety of absorbent and/or adsorbent materials (e.g. wipes, mop heads, sponges, towels, etc.). The results of the test reveal the benefit of using a dual solvent system in the improved cleaning composition, with or without polymer.

II. Other Types of Cleaners

The improved cleaning composition is particularly applicable for use with hard surfaces; however, the improved cleaning composition can be formulated for use in other types of cleaners. As can be appreciated, the various applications for the improved cleaning composition include, but are not limited to, domestic and industrial applications. Several applications include, but are not limited to, power wash solutions, deck cleaners; vehicle cleaners, house siding cleaners; fire arm cleaners; and the like. Depending on the particular application for the improved cleaning composition, the cleaning composition can be formulated to disinfect, sanitize, and/or sterilize. As can be appreciated, the improved cleaning composition can be used in many other types of applications that require cleaning, and disinfecting, sanitizing, and/or sterilizing of a surface.

As with hard surface formulations, the improved cleaning composition can be in concentrated form or ready-to-use form. The improved cleaning composition can be in gas, liquid, paste, gel, or solid form. The improved cleaning composition can be dispensed from a liquid container, an aerosol container, a container for holding crystals or a paste, and the like. The improved cleaning composition can be preloaded onto an absorbent and/or adsorbent material.

The basic components of the improved cleaning composition when used other applications include:

(I) cationic biocide; and, (ii) surfactant and/or biocide release agent.

The cationic biocide, surfactant, and/or biocide release agent used in the improved cleaning composition can be the same or similar compounds used in the improved cleaning composition for hard surfaces. The cationic biocide (e.g., biguanide compound, quat, etc.) in the improved cleaning composition is used at least in part to enhance the disinfecting, sanitizing, and/or sterilizing attributes of the improved cleaning composition. The biocide release agent in the improved cleaning composition is used at least in part to reduce or prevent the retention of the cationic biocide on an absorbent and/or adsorbent surface.

The improved cleaning composition can also include buffering and pH adjusting agents, fragrances or perfumes, waxes, dyes and/or colorants, solubilizing materials, stabilizers, thickeners, defoamers, hydrotropes, lotions and/or mineral oils, enzymes, bleaching agents, cloud point modifiers, preservatives, ion exchangers, alkalies, anticorrosion materials, antiredeposition materials, optical brighteners, chelating agents, enzymes, whiteners, brighteners, antistatic agents, sudsing control agents, hydrotropes, bleach precursors, soil removal agents, anti-dye transfer agents, soil release agents, softening agents, opacifiers, inert diluents, graying inhibitors, stabilizers, and/or polymers.

A one general formulation of the improved cleaning composition in weight percent is as follows:

| | |
|---|---|
| Cationic Biocide | 0.02-20% |
| Biocide Release Agent | 0.025-90% |
| Water | less than about 99.95% | wherein the ionic strength of the biocide release agent is at least about $5 \times 10^{-3}$ mol/l.

Another general formulation of the improved cleaning composition in weight percent is as follows:

| | |
|---|---|
| Cationic Biocide | 0.02-20% |
| Surfactant | 0.05-99% |
| Water | less than about 99.95% |

Several specific, nonlimiting, examples of the improved cleaning composition in weight percent are as follows.

Example 33

| | |
|---|---|
| Biocide | 0.02-10% |
| Biocide release agent | 0.03-10% |
| Builder/solvent/Surfactant | 0-99% |
| Water | 0-99.95% | wherein the ionic strength of the biocide release agent is at least about $5\times10^{-3}$ mol/l.

Example 34

| | |
|---|---|
| Biocide | 0.05-5% |
| Biocide release agent | 0.03-10% |
| Builder/solvent/Surfactant | 0.001-75% |
| Water | at least 10% | wherein the ionic strength of the biocide release agent is at least about $5\times10^{-3}$ mol/l.

Example 35

| | |
|---|---|
| Biocide | 0.02-5% |
| Biocide release agent | 0.03-5% |
| Builder/solvent/Surfactant | 0-27% |
| Water | at least 60% | wherein the ionic strength of the biocide release agent is at least about $5\times10^{-3}$ mol/l.

Example 36

| | |
|---|---|
| Biocide | 0.1-2% |
| Biocide release agent | 0.08-3% |
| Builder/solvent/Surfactant | 0.015-35% |
| Water | at least 60% | wherein the ionic strength of the biocide release agent is at least about $1\times10^{-2}$ mol/l.

Example 37

| | |
|---|---|
| Biocide | 0.04-2% |
| Biocide release agent | 0.05-2.5% |
| Builder/solvent/Surfactant | 0.05-17% |
| Water | at least 78.5% | wherein the ionic strength of the biocide release agent is at least about $1\times10^{-2}$ mol/l.

Example 38

| | |
|---|---|
| Biocide | 0.15-0.8% |
| Biocide release agent | 0.1-2.5% |
| Builder/solvent/Surfactant | 0.085-12.8% |
| Water | at least 80% | wherein the ionic strength of the biocide release agent is about $2\times10^{-2}$-1 mol/l.

Example 39

| | |
|---|---|
| Biocide | 0.1-2% |
| Biocide release agent | 0.1-2% |
| Builder/solvent/Surfactant | 0.2-10% |
| Water | at least 86% | wherein the ionic strength of the biocide release agent is about $2\times10^{-2}$-1 mol/l.

Example 40

| | |
|---|---|
| Biocide | 0.2-0.5% |
| Biocide release agent | 0.5-2% |
| Builder/solvent/Surfactant | 2.95-9.3% |
| Water | at least 85% | wherein the ionic strength of the biocide release agent is about $3\times10^{-2}$-0.4 mol/l.

Example 41

| | |
|---|---|
| Biocide | 0.1-1% |
| Biocide release agent | 0.1-2% |
| Builder/solvent/Surfactant | 2-10% |
| Water | at least 87% | wherein the ionic strength of the biocide release agent is about $3\times10^{-2}$-0.4 mol/l.

Example 42

| | |
|---|---|
| Biocide | 0.25-0.4% |
| Biocide release agent | 0.75-1.8% |
| Builder/solvent/Surfactant | 3.07-5.65% |
| Water | at least 85% | wherein the ionic strength of the biocide release agent is about $4\times10^{-2}$-0.2 mol/l.

Example 43

| | |
|---|---|
| Biocide | 0.02-10% |
| Builder/solvent/Surfactant/biocide release agent | 0-99% |
| Water | 0-99.95% |

Example 44

| | |
|---|---|
| Biocide | 0.05-5% |
| Builder/solvent/Surfactant/biocide release agent | 0.001-75% |
| Water | at least 10% |

Example 45

| | |
|---|---|
| Biocide | 0.02-5% |
| Builder/solvent/Surfactant/biocide release agent | 0-27% |
| Water | at least 60% |

Example 46

| | |
|---|---|
| Biocide | 0.1-2% |
| Builder/solvent/Surfactant/biocide release agent | 0.015-35% |
| Water | at least 60% |

Example 47

| | |
|---|---|
| Biocide | 0.04-2% |
| Builder/solvent/Surfactant/biocide release agent | 0.05-17% |
| Water | at least 78.5% |

Example 48

| | |
|---|---|
| BARQUAT 4250Z | 0.3-0.4% |
| Potassium Citrate | 0.09-1.1% |
| Disodium EDTA | 0.09-0.15% |
| Isopropanol | 0-5% |
| Lauryl Dimethyl Amine Oxide | 0.2-0.4% |
| Fragrance | 0-1% |
| Water | at least 90% | wherein the ionic strength of the salts in the improved cleaning composition is about $3.5 \times 10^{-2}$-$5 \times 10^{-2}$ mol/l.

Example 49

| | |
|---|---|
| Vantocil P | 0.1-0.5% |
| Isopropanol | 0-5% |
| PnB (glycol ether) | 0.5-2% |
| Surfactant | 0-1.5% |
| Ammonium Chloride | 0.05-1% |
| Dipotassium EDTA | 0-0.5% |
| Fragrance | 0-1% |
| Water | at least 89.5% | wherein the ionic strength of the salts in the improved cleaning composition is about $3.5 \times 10^{-2}$-$5 \times 10^{-2}$ mol/l.

Example 50

| | |
|---|---|
| BTC 2250 | 0.3-0.4% |
| Sodium Citrate | 0.9-1.1% |
| DiPotassium EDTA | 0-0.15% |
| Isopropanol | 0-5% |
| Lauryl Dimethyl Amine Oxide | 0.2-0.4% |
| Water | at least 90% | wherein the ionic strength of the salts in the improved cleaning composition is about $3.75 \times 10^{-2}$-$5.4 \times 10^{-2}$ mol/l.

Example 51

| | |
|---|---|
| Vantocil P | 0.15-0.5% |
| Isopropanol | 0.1-4% |
| PnB (glycol ether) | 0.5-1.5% |
| Surfactant | 0-1.5% |
| Ammonium Chloride | 0.05-1% |
| Dipotassium EDTA | 0-0.3% |
| Fragrance | 0-1% |
| Water | at least 90% | wherein the ionic strength of the salts in the improved cleaning composition is about $3.75 \times 10^{-2}$-$5.4 \times 10^{-2}$ mol/l.

Example 52

| | |
|---|---|
| BTC 2250 | 0.05-0.4% |
| Vantocil P | 0.05-0.4% |
| Sodium Citrate | 0.2-2% |
| DiPotassium EDTA | 0-0.5% |
| PnB (glycol ether) | 0-2% |
| Surfactant | 0-2% |
| Isopropanol | 0-5% |
| Lauryl Dimethyl Amine Oxide | 0-1% |
| Water | at least 90% | wherein the ionic strength of the salts in the improved cleaning composition is about $3.75 \times 10^{-2}$-$5.4 \times 10^{-2}$ mol/l.

Example 53

| | |
|---|---|
| BARQUAT 205M | 0.1-0.3% |
| Ammonium Chloride | 0.05-0.4% |
| DiPotassium EDTA | 0.3-0.5% |
| PnB (glycol ether) | 1-2% |
| Surfactant | 0.2-1% |
| Isopropanol | 0-4% |
| Lauryl Dimethyl Amine Oxide | 0-1% |
| Fragrance | 0-1% |
| Water | at least 90% | wherein the ionic strength of the salts in the improved cleaning composition is about $3.75 \times 10^{-2}$-$5.4 \times 10^{-2}$ mol/l.

The invention has been described with reference to a preferred embodiment and alternates thereof. It is believed that many modifications and alterations to the embodiments disclosed will readily suggest itself to those skilled in the art upon reading and understanding the detailed description of the invention. It is intended to include all such modifications and alterations insofar as they come within the scope of the present invention.

We claim:

1. A method for cleaning a surface comprising:
   a. providing an absorbent or adsorbent material, said absorbent or adsorbent material including a material selected from the group consisting of wood pulp, wood pulp derivative, synthetic fibers, and mixtures thereof;
   b. at least partially exposing said absorbent or adsorbent material with an improved cleaning composition, said improved cleaning composition including a cationic biocide and a surfactant, said cationic biocide including a compound selected from the group consisting of biguanide compound, quaternary ammonium compound or mixtures thereof, said improved cleaning composition including 0.25-2 weight percent quaternary ammonium compound, biguanide or combinations thereof, 0.1-5 weight percent alcohol containing solvent, 0-2 weight percent non-alcohol containing solvent, 0.1-3 weight percent surfactant containing alkyl polyglycoside, amine oxide, or combinations thereof, 0-0.5 weight percent builder detergent, 0.05-5 weight percent copolymer of vinylpyrrolidone and dimethylaminoethylmethacrylate quaternized with diethylsulfate, 0.1-2 weight percent biocide release agent, and at least 10 weight percent water, and;
   c. contacting said surface with said absorbent or adsorbent material and said improved cleaning composition to cause over 50% of the cationic biocide to be released from said absorbent or adsorbent material.

2. The method as defined in claim 1, wherein said step of contacting at least partially disinfects said surface, sanitizes said surface, sterilizes said surface or combinations thereof.

3. The method as defined in claim 1, wherein said absorbent or adsorbent material is at least partially impregnated with said improved cleaning composition prior to said absorbent or adsorbent material contacting said surface.

4. The method as defined in claim 1, wherein said absorbent or adsorbent material is selected from the group consisting of a cleaning wipe, a cleaning pad, a mop head or combinations thereof.

5. The method as defined in claim 2, wherein said absorbent or adsorbent material is selected from the group consisting of a cleaning wipe, a cleaning pad, a mop head or combinations thereof.

6. The method as defined in claim 1, said alcohol containing solvent has a boiling point of less than about 150° C. and said non-alcohol containing solvent has a boiling point of at least about 150° C., a weight ratio of said alcohol containing solvent to said non-alcohol containing solvent is about 10-1:1.

7. The method as defined in claim 5, said alcohol containing solvent has a boiling point of less than about 150° C. and said non-alcohol containing solvent has a boiling point of at least about 150° C., a weight ratio of said alcohol containing solvent to said non-alcohol containing solvent is about 10-1:1.

8. The method as defined in claim 1, said biocide release agent having an ionic strength in said improved cleaning composition of about $5 \times 10^{-3}$-18 mol/l.

9. The method as defined in claim 7, said biocide release agent having an ionic strength in said improved cleaning composition of about $5 \times 10^{-3}$-18 mol/l.

10. The method as defined in claim 1, wherein said cationic biocide includes a biguanide compound.

11. The method as defined in claim 1, wherein said cationic biocide includes a quaternary ammonium compound.

12. A method for cleaning a surface comprising:
    a. providing an absorbent or adsorbent material, said absorbent or adsorbent material including a material selected from the group consisting of wood pulp, wood pulp derivative, synthetic fibers, and mixtures thereof;
    b. at least partially exposing said absorbent or adsorbent material with an improved cleaning composition, said improved cleaning composition including 0.25-2 weight percent quaternary ammonium compound, biguanide or combinations thereof, 0.1-5 weight percent alcohol containing solvent, 0-2 weight percent non-alcohol containing solvent, 0.1-3 weight percent surfactant containing alkyl polyglycoside, amine oxide, or combinations thereof, 0-0.5 weight percent builder detergent, 0.05-5 weight percent copolymer of vinylpyrrolidone and dimethylaminoethylmethacrylate quaternized with diethylsulfate, 0.1-2 weight percent biocide release agent, and at least 10 weight percent water; c. and contacting said hard surface with said absorbent or adsorbent material and said improved cleaning composition.

13. The method as defined in claim 12, wherein said step of contacting at least partially disinfects said surface, sanitizes said surface, sterilizes said surface or combinations thereof.

14. The method as defined in claim 12, wherein said absorbent or adsorbent material is at least partially impregnated with said improved cleaning composition prior to said absorbent or adsorbent material contacting said surface.

15. The method as defined in claim 12, wherein said absorbent or adsorbent material is selected from the group consisting of a cleaning wipe, a cleaning pad, a mop head or combinations thereof.

16. The method as defined in claim 13, wherein said absorbent or adsorbent material is selected from the group consisting of a cleaning wipe, a cleaning pad, a mop head or combinations thereof.

17. The method as defined in claim 12, said biocide release agent having an ionic strength in said improved cleaning composition of about $5 \times 10^{-3}$-18 mol/l.

18. The method as defined in claim 16, said biocide release agent having an ionic strength in said improved cleaning composition of about $5 \times 10^{-3}$-18 mol/l.

19. The method as defined in claim 12, wherein said cationic biocide includes a biguanide compound.

20. The method as defined in claim 12, wherein said cationic biocide includes a quaternary ammonium compound.

21. A method for cleaning a surface comprising:
    a. providing an absorbent or adsorbent material, said absorbent or adsorbent material including a material selected from the group consisting of wood pulp, wood pulp derivative, synthetic fibers, and mixtures thereof;
    b. at least partially exposing said absorbent or adsorbent material with an improved cleaning composition, said improved cleaning composition including 0.25-2 weight percent quaternary ammonium compound, biguanide or combinations thereof, 0.1-5 weight percent alcohol containing solvent, 0-2 weight percent non-alcohol containing solvent, 0.1-3 weight percent surfactant containing alkyl polyglycoside, amine oxide, or combinations thereof, 0-0.5 weight percent builder detergent, 0.05-5 weight percent copolymer of vinylpyrrolidone and dimethylaminoethylmethacrylate quaternized with diethylsulfate, 0.1-2 weight percent biocide release agent, and at least 10 weight percent water, said alcohol containing solvent has a boiling point of less than about 150° C. and said non-alcohol containing solvent has a boiling point of at least about 150° C. a weight ratio of said alcohol containing solvent to said non-alcohol containing solvent is about 10-1:1 c. and contacting said hard surface with said absorbent or adsorbent material and said improved cleaning composition.

22. The method as defined in claim 21, wherein said step of contacting at least partially disinfects said surface, sanitizes said surface, sterilizes said surface or combinations thereof.

23. The method as defined in claim 21, wherein said absorbent or adsorbent material is at least partially impregnated with said improved cleaning composition prior to said absorbent or adsorbent material contacting said surface.

24. The method as defined in claim 21, wherein said absorbent or adsorbent material is selected from the group consisting of a cleaning wipe, a cleaning pad, a mop head or combinations thereof.

25. The method as defined in claim 22, wherein said absorbent or adsorbent material is selected from the group consisting of a cleaning wipe, a cleaning pad, a mop head or combinations thereof.

26. The method as defined in claim 21, wherein said alcohol containing solvent includes a compound selected from the group consisting of methanol, ethanol, isopropanol, propanol, butyl alcohol, sec-butyl alcohol, isobutyl alcohol, tert-butyl alcohol, pentyl alcohol, tert-pentyl alcohol, 2-pentanol, 3-pentanol, neopentyl alcohol, ethyleneglycol methylether, ethyleneglycol ethylether, ethyleneglycol propylether, propyleneglycol methylether, propyleneglycol ethylether, ethyleneglycol methyletheracetate, propyleneglycol methyletheracetate or combinations thereof, and said non-alcohol solvent includes a compound selected from the group consisting of ethylene glycol, propylene glycol, butanediol, methylpropanediol, ethyleneglycol butylether, ethyleneglycol hexylether, ethyleneglycol ethylhexylether, diethyleneglycol methylether, diethyleneglycol ethylether, diethyleneglycol propylether, diethyleneglycol butylether, propyleneglycol propylether, propyleneglycol t-butylether, propyleneglycol butylether, dipropyleneglycol methylether, dipropyleneglycol ethylether, dipropyleneglycol propylether, dipropyleneglycol t-butylether, dipropyleneglycol butylether, tripropyleneglycol methylether, tripropyleneglycol butylether, ethyleneglycol ethyletheracetate, propyleneglycol ethyletheracetate, ethyleneglycol butyletheracetate, propyleneglycol butyletheracetate, diethyleneglycol methyletheracetate, dipropyleneglycol methyletheracetate, diethyleneglycol ethyletheracetate, dipropyleneglycol ethyletheracetate, diethyleneglycol butyletheracetate, dipropyleneglycol butyletheracetate, N-methyl-2-pyrrolidone or combinations thereof.

27. The method as defined in claim 25, wherein said alcohol containing solvent includes a compound selected from the group consisting of methanol, ethanol, isopropanol, propanol, butyl alcohol, sec-butyl alcohol, isobutyl alcohol, tert-butyl alcohol, pentyl alcohol, tert-pentyl alcohol, 2-pentanol, 3-pentanol, neopentyl alcohol, ethyleneglycol methylether, ethyleneglycol ethylether, ethyleneglycol propylether, propyleneglycol methylether, propyleneglycol ethylether, ethyleneglycol methyletheracetate, propyleneglycol methyletheracetate or combinations thereof, and said non-alcohol solvent includes a compound selected from the group consisting of ethylene glycol, propylene glycol, butanediol, methylpropanediol, ethyleneglycol butylether, ethyleneglycol hexylether, ethyleneglycol ethylhexylether, diethyleneglycol methylether, diethyleneglycol ethylether, diethyleneglycol propylether, diethyleneglycol butylether, propyleneglycol propylether, propyleneglycol t-butylether, propyleneglycol butylether, dipropyleneglycol methylether, dipropyleneglycol ethylether, dipropyleneglycol propylether, dipropyleneglycol t-butylether, dipropyleneglycol butylether, tripropyleneglycol methylether, tripropyleneglycol butylether, ethyleneglycol ethyletheracetate, propyleneglycol ethyletheracetate, ethyleneglycol butyletheracetate, propyleneglycol butyletheracetate, diethyleneglycol methyletheracetate, dipropyleneglycol methyletheracetate, diethyleneglycol ethyletheracetate, dipropyleneglycol ethyletheracetate, diethyleneglycol butyletheracetate, dipropyleneglycol butyletheracetate, N-methyl-2-pyrrolidone or combinations thereof.

28. The method as defined in claim 21, said biocide release agent having an ionic strength in said improved cleaning composition of about $5\times10^{-3}$-18 mol/l.

29. The method as defined in claim 27, said biocide release agent having an ionic strength in said improved cleaning composition of about $5\times10^{-3}$-18 mol/l.

30. The method as defined in claim 21, wherein said cationic biocide includes a biguanide compound.

31. The method as defined in claim 21, wherein said cationic biocide includes a quaternary ammonium compound.

32. The method as defined in claim 1, wherein said improved cleaning composition includes at least two different surfactants, at least one of said surfactants including a fluorosurfactant.

33. The method as defined in claim 9, wherein said improved cleaning composition includes at least two different surfactants, at least one of said surfactants including a fluorosurfactant.

34. The method as defined in claim 12, wherein said improved cleaning composition includes at least two different surfactants, at least one of said surfactants including a fluorosurfactant.

35. The method as defined in claim 18, wherein said improved cleaning composition includes at least two different surfactants, at least one of said surfactants including a fluorosurfactant.

36. The method as defined in claim 21, wherein said improved cleaning composition includes at least two different surfactants, at least one of said surfactants including a fluorosurfactant.

37. The method as defined in claim 29, wherein said improved cleaning composition includes at least two different surfactants, at least one of said surfactants including a fluorosurfactant.

* * * * *